(12) United States Patent
Pesiridis et al.

(10) Patent No.: US 12,178,851 B2
(45) Date of Patent: *Dec. 31, 2024

(54) METHODS FOR ADMINISTERING STING AGONISTS

(71) Applicant: GlaxoSmithKline Intellectual Property Development Limited, Brentford (GB)

(72) Inventors: George Scott Pesiridis, Collegeville, PA (US); Jean-Luc Tran, Collegeville, PA (US); Jingsong Yang, Collegeville, PA (US); Joshi M Ramanjulu, Collegeville, PA (US)

(73) Assignee: GlaxoSmithKline Intellectual Property Development Limited (GB)

( * ) Notice: Subject to any disclaimer, the term of this patent is extended or adjusted under 35 U.S.C. 154(b) by 895 days.

This patent is subject to a terminal disclaimer.

(21) Appl. No.: 16/753,365

(22) PCT Filed: Oct. 4, 2018

(86) PCT No.: PCT/IB2018/057738
§ 371 (c)(1),
(2) Date: Apr. 3, 2020

(87) PCT Pub. No.: WO2019/069275
PCT Pub. Date: Nov. 4, 2019

(65) Prior Publication Data
US 2020/0330556 A1    Oct. 22, 2020

Related U.S. Application Data

(60) Provisional application No. 62/568,392, filed on Oct. 5, 2017.

(51) Int. Cl.
| | | |
|---|---|---|
| *A61K 31/4184* | (2006.01) |
| *A61K 31/496* | (2006.01) |
| *A61K 31/5377* | (2006.01) |
| *A61K 38/19* | (2006.01) |
| *A61K 38/20* | (2006.01) |
| *A61K 38/21* | (2006.01) |
| *A61P 35/00* | (2006.01) |
| *A61K 9/00* | (2006.01) |

(52) U.S. Cl.
CPC ........ *A61K 38/204* (2013.01); *A61K 31/4184* (2013.01); *A61K 31/496* (2013.01); *A61K 31/5377* (2013.01); *A61K 38/191* (2013.01); *A61K 38/215* (2013.01); *A61K 38/217* (2013.01); *A61P 35/00* (2018.01); *A61K 9/0019* (2013.01)

(58) Field of Classification Search
CPC .............. A61K 31/4184; A61K 31/496; A61K 31/5377; C07D 403/14
See application file for complete search history.

(56) References Cited

U.S. PATENT DOCUMENTS

| | | | |
|---|---|---|---|
| 10,189,820 B2 * | 1/2019 | Mehlmann | A61P 37/04 |
| 10,981,901 B1 * | 4/2021 | Romano | C07D 413/14 |
| 11,365,190 B2 * | 6/2022 | Charley | C07D 403/14 |
| 11,970,480 B2 * | 4/2024 | Charley | A61P 31/08 |
| 2016/0220652 A1 | 8/2016 | Petit et al. | |
| 2017/0044206 A1 * | 2/2017 | Altman | C07H 21/00 |
| 2018/0093964 A1 * | 4/2018 | Altman | C07D 333/60 |
| 2018/0105514 A1 * | 4/2018 | Mehlmann | A61P 37/00 |
| 2021/0139473 A1 * | 5/2021 | Charnley | C07D 413/14 |
| 2023/0071675 A1 * | 3/2023 | Charnley | A61P 31/12 |

FOREIGN PATENT DOCUMENTS

| | | | |
|---|---|---|---|
| CN | 106552265 | 6/2016 | |
| WO | WO-2017175147 A1 * | 10/2017 | ......... A61K 31/4178 |

OTHER PUBLICATIONS

Curran et al. Cell Reports 2016, 15, 2357-2366 (Year: 2016).*
Liu et al. Antiviral Res. 2017, 147, 37-46 (Year: 2017).*
Barber, Nature Reviews: Immunology 2015, 15, 760-770 (Year: 2015).*
Sokolowoska et al. Arch. Immunol. Ther. Exp. 2018, 66, 125-132 (Year: 2017).*
Luo et al. Cell, 2009, 136, pp. 823-837 (Year: 2009).*

* cited by examiner

*Primary Examiner* — Matthew P Coughlin
(74) *Attorney, Agent, or Firm* — J. Scott Young

(57) ABSTRACT

The present invention relates to methods of treating disease states, including cancer, in a human comprising systemically administering a STING agonist, or a pharmaceutically acceptable salt thereof, to said human.

24 Claims, 12 Drawing Sheets

METHODS FOR ADMINISTERING STING AGONISTS

FIELD OF THE INVENTION

The present invention relates to methods of delivering STING (Stimulator of Interferon Genes) agonists. The invention also relates to the use of said compounds, combinations, compositions and medicaments, in the treatment of diseases in which modulation of STING (Stimulator of Interferon Genes) is beneficial, for example inflammation, allergic and autoimmune diseases, infectious diseases, hepatitis C virus (HCV), hepatitis B virus (HBV), influenza, skin warts, multiple sclerosis, human immunodeficiency virus (HIV) infection, AIDS, cancer, pre-cancerous syndromes and as immunogenic composition or vaccine adjuvants.

BACKGROUND TO THE INVENTION

Vertebrates are constantly threatened by the invasion of microorganisms and have evolved mechanisms of immune defence to eliminate infective pathogens. In mammals, this immune system comprises two branches; innate immunity and adaptive immunity. The innate immune system is the first line of defence which is initiated by Pattern Recognition Receptors (PRRs) which detect ligands from the pathogens as well as damage associated molecular patterns (Takeuchi O. et al, Cell, 2010: 140, 805-820). A growing number of these receptors have been identified including Toll-like receptors (TLRs), C-type lectin receptors, retinoic acid inducible gene I (RIG-I)-like receptors and NOD-like receptors (NLRs) and also double stranded DNA sensors. Activation of PRRs leads to up-regulation of genes involved in the inflammatory response including type 1 interferons, pro-inflammatory cytokines and chemokines which suppress pathogen replication and facilitate adaptive immunity.

The adaptor protein STING (Stimulator of Interferon Genes), also known as TMEM 173, MPYS, MITA and ERIS, has been identified as a central signalling molecule in the innate immune response to cytosolic nucleic acids (Ishikawa H and Barber G N, Nature, 2008: 455, 674-678; WO2013/1666000). Activation of STING results in up-regulation of IRF3 and NFκB pathways leading to induction of Interferon-β and other cytokines. STING is critical for responses to cytosolic DNA of pathogen or host origin, and to unusual nucleic acids called Cyclic Dinucleotides (CDNs)

CDNs were first identified as bacterial secondary messengers responsible for controlling numerous responses in the prokaryotic cell. Bacterial CDNs, such as c-di-GMP are symmetrical molecules characterised by two 3',5' phosphodiester linkages.

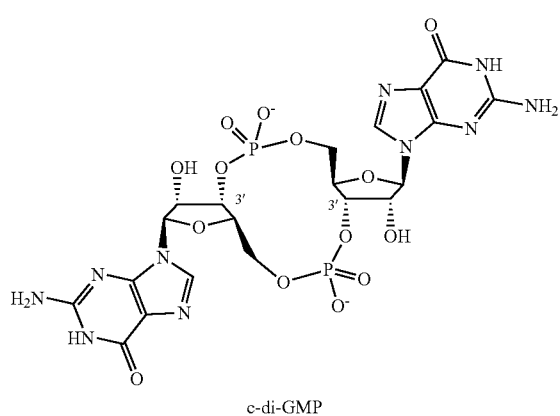

c-di-GMP

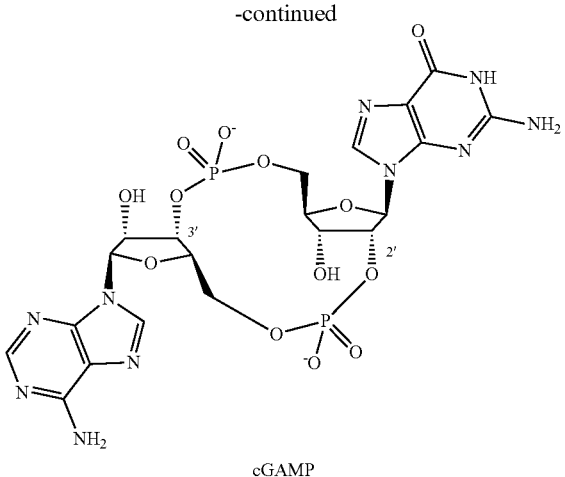

cGAMP

Direct activation of STING by bacterial CDNs has recently been confirmed through X-ray crystallography (Burdette D L and Vance R E, Nature Immunology, 2013: 14, 19-26). Bacterial CDNs and their analogues have consequently attracted interest as potential vaccine adjuvants (Libanova R. et al, Microbial Biotechnology 2012: 5, 168-176; WO2007/054279, WO2005/087238).

More recently, the response to cytosolic DNA has been elucidated and shown to involve generation, by an enzyme called cyclic GMP-AMP synthase (cGAS, previously known as C6orf150 or MB21D1), of a novel mammalian CDN signalling molecule identified as cGAMP, which then activates STING. Unlike bacterial CDNs, cGAMP is an unsymmetrical molecule characterised by its mixed 2',5' and 3',5' phosphodiester linkages. (Gao P et al, Cell, 2013: 153, 1-14). Interaction of cGAMP with STING has also been demonstrated by X-ray crystallography (Cai X et al, Molecular Cell, 2014: 54, 289-296).

Interferon was first described as a substance which could protect cells from viral infection (Isaacs & Lindemann, J. Virus Interference. Proc. R. Soc. Lon. Ser. B. Biol. Sci. 1957: 147, 258-267). In man, the type I interferons are a family of related proteins encoded by genes on chromosome 9 and encoding at least 13 isoforms of interferon alpha (IFNα) and one isoform of interferon beta (IFNβ). Recombinant IFNα was the first approved biological therapeutic and has become an important therapy in viral infections and in cancer. As well as direct antiviral activity on cells, interferons are known to be potent modulators of the immune response, acting on cells of the immune system.

Administration of a small molecule compound which could stimulate the innate immune response, including the activation of type I interferons and other cytokines, could become an important strategy for the treatment or prevention of human diseases including viral infections. This type of immunomodulatory strategy has the potential to identify compounds which may be useful not only in infectious diseases but also in cancer (Zitvogel, L., et al., Nature Reviews Immunology, 2015 15(7), p 405-414), allergic diseases (Moisan J. et al, Am. J Physiol. Lung Cell Mol. Physiol., 2006: 290, L987-995), other inflammatory conditions such as irritable bowel disease (Rakoff-Nahoum S., Cell., 2004, 23, 118(2): 229-41), and as vaccine adjuvants (Persing et al. Trends Microbiol. 2002: 10(10 Suppl), S32-7 and Dubensky et al., Therapeutic Advances in Vaccines, published on line Sep. 5, 2013).

Allergic diseases are associated with a Th2-biased immune-response to allergens. Th2 responses are associated with raised levels of IgE, which, via its effects on mast cells, promotes a hypersensitivity to allergens, resulting in the symptoms seen, for example, in allergic rhinitis and asthma. In healthy individuals, the immune-response to allergens is more balanced with a mixed Th2/Th1 and regulatory T cell response. Induction of Type 1 interferons have been shown to result in reduction of Th2-type cytokines in the local environment and promote Th1/Treg responses. In this context, induction of type 1 interferons by, for example, activation of STING, may offer benefit in treatment of allergic diseases such as asthma and allergic rhinitis (Huber J. P. et al *J Immunol* 2010: 185, 813-817).

In contrast, increased and prolonged type I IFN production is associated with a variety of chronic infections, including Mycobacteria (Collins et al, *CHM* 2015; Wassermann et al., *CHM* 2015; Watson et al., *CHM* 2015), Franciscella (Storek et al., *JI* 2015; Jin et al., *JI* 2011), Chlamydia (Prantner et al., *JI* 2010; Barker et al., *Mbio* 2013; Zhang et al., *JI* 2014), Plasmodium (Sharma et al., *Immunity* 2011) and HIV (Herzner et al., *Nat Immunol* 2015; Nissen et al., *Clin Exp Immunol* 2014; Gao et al., *Science* 2013; Lahaye et al, *Science* 2013); (reviewed in Stifter and Feng, *JI* 2014). Similarly, excess type I interferon production is found among patients with complex forms of autoimmune disease. Genetic evidence in humans and support from studies in animal models support the hypothesis that inhibition of STING results in reduced type I interferon that drives autoimmune disease (Crow Y J, et al., *Nat. Genet.* 2006; 38917-920, Stetson D B, et al., *Cell* 2008; 134; 587-598). Therefore, inhibitors of STING provide a treatment to patients with chronic type I interferon and proinflammatory cytokine production associated with infections or complex autoimmune diseases. Allergic diseases are associated with a Th2-biased immune-response to allergens.

Type I IFN has been implicated to contributing to the innate immune sensing of immunogenic tumors leading to adaptive T-cells responses via STING and IRF3 pathway as demonstrated in by Woo, S-Y et. al. Immunity 41:330-342 (2014), Diamond. M. et. al. (2011). and Corrales. L. et. al. Cell reports 11:1018-1030 (2015).

Additionally, the mouse specific STING agonist small molecule (DMXAA) has also been shown to induce tumor regression in on multiples tumor mouse models and induced Type-I IFN-β in normal wide type mouse and lost of ability to reject tumor growth and induction of type-I IFN-β in the STING$^{(-/-)}$ mouse. This indicated that STING induces type-1 IFN-β is a central component mediated tumor cells death and adaptive immunity responses to drive tumor regression. Welsh. R. et. al. (2012), Li. K. et. al (2017), and Vargas TR. et. al. (2017).

Compounds that bind to STING and act as agonist have been shown to induce type 1 interferons and other cytokines on incubation with human PBMCs. Compounds which induce human interferons may be useful in the treatment of various diseases, for example inflammation, allergic and autoimmune diseases, infectious diseases, hepatitis C virus (HCV), hepatitis B virus (HBV), influenza, skin warts, multiple sclerosis, human immunodeficiency virus (HIV) infection, AIDS, cancer, (including basal cell carcinoma, and squamous cell carcinoma), pre-cancerous syndromes (including actinic keratoses), and as immunogenic composition or vaccine adjuvants.

Thus, there is a need for methods of administering these compounds for the effective treatment of these diseases. In particular, there remains a need for methods that allow for increased cytokine production in disease tissue and for the safe and effective systemic administration of a STING agonist that does not require the use of a targeting formulation.

SUMMARY OF THE INVENTION

In one embodiment, the present invention provides methods of treating cancer in a human comprising systemically administering a STING agonist to said human, wherein the STING agonist induces a higher concentration of at least one cytokine in a tumor microenvironment of said human compared with the concentration of said cytokine in the blood, plasma or serum of said human.

In one embodiment of the present invention, methods are provided of administering a STING agonist to a human in need thereof comprising systemically administering said STING agonist. In one embodiment, the STING agonist increases the concentration of at least one cytokine in the blood, plasma or serum of said human to a concentration effective to stimulate Tcells in said human. In one aspect, the cytokine concentrations are not increased high enough to produce adverse immune effects in said human. In one embodiment, methods are provided comprising administering a STING agonist to a human in need thereof wherein the STING agonist increases the concentration of at least one pro-inflammatory cytokine in disease tissue in said human at least three times higher than the concentration of said at least on pro-inflammatory cytokine in the blood, plasma or serum of said human.

BRIEF DESCRIPTION OF THE DRAWINGS

FIG. 2(B) Dose Titration of Compound 1 measured at 3.5 hours post IV administration.

FIG. 4(B) Serum and Tumor TNF-α; FIG. 4(C) Serum and Tumor IFN-β; FIG. 4(D) Serum and Tumor Ifn-γ.

FIG. 5(A) Blood and tumor concentration of Compound 1 at 3.5 hours following IV bolus dose to CT26 tumor bearing BALB/c mice FIG. 5(B) Dose titration of Compound 1 and detection of IFNβ blood and tumors FIG. 6(A) $ED_{50}$ Curves Dose response of tumor IFNβ to Compound 1 dose measured at 3.5 hr after IV dose titration.

FIG. 6(B): ED50 curve of Tumor volume area under the curve of tumor regression responded to IV administration treatment with Compound 1.

FIG. 9(A) Increased of Dendritic cell at tumor microenvironment and draining lymph node over time. FIG. 9(B) Increased MHC-1 expression on draining lymph node on NK, B and T cells.

FIG. 10(A) No effect of Body Weight upon IV administration of compound.

FIG. 10(B) Loss of efficacy tumor regression of Compound 1 in the CD8 T cells depletion tumor model).

DETAILED DESCRIPTION OF THE INVENTION

Figure 1:
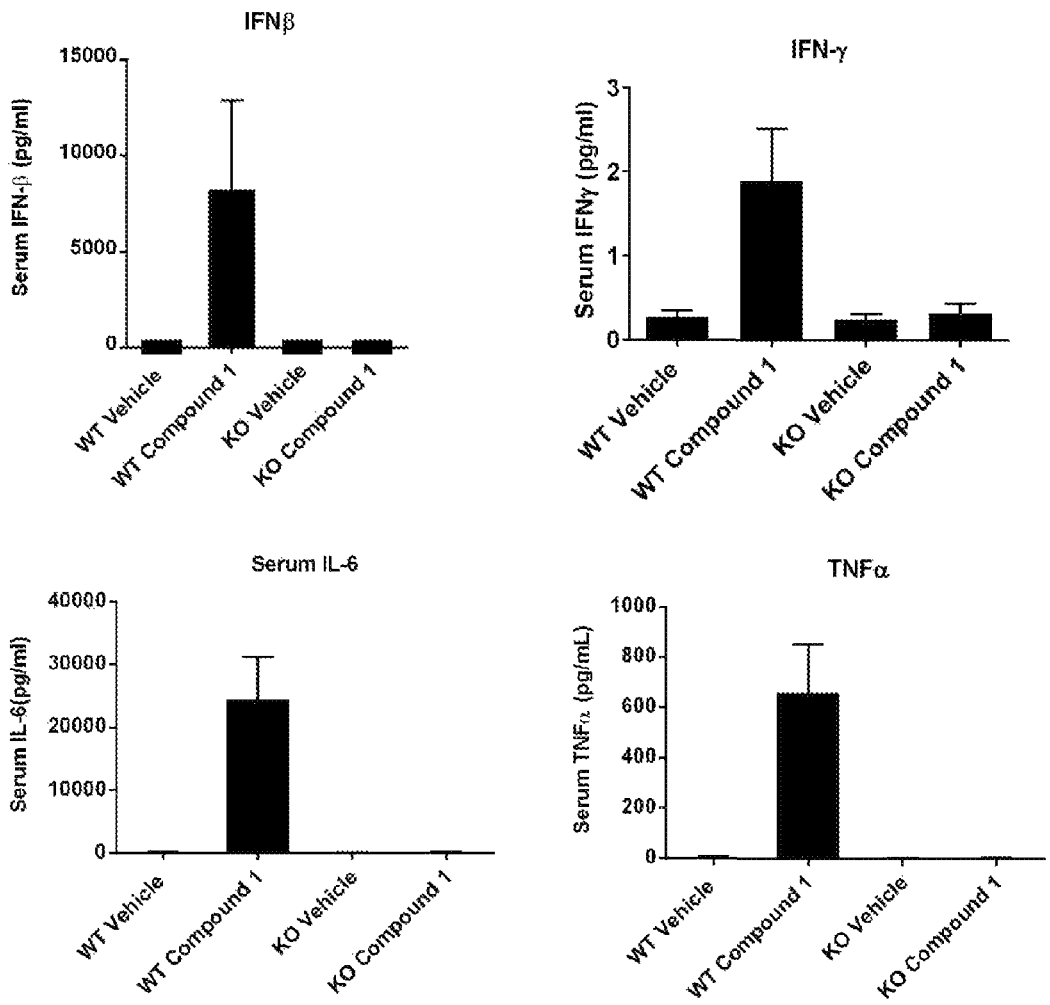
FIG. 1: Compound 1 generates STING specific cytokines in mice: Compound 1 induces IFNβ and pro-inflammatory cytokines in WT but not in a STING knock-out (KO) mouse.

The systemic activation of pattern recognition receptors (PRR) receptors, including STING, throughout an entire organism can lead the production of large amounts of proinflammatory cytokines resulting in an unacceptable side-effect profile. These adverse side effects include, elevation of body temperature, aches, pain and nausea. Bacterial LPS, a TLR4 agonist, is the primary mediator of bacterial induced-septicaemia, which is characterized in its early stages by a cytokine storm which often leads to death (Schulte, W.; Bernhagen, J.; Bucala, R., Cytokines in Sepsis: Potent Immunoregulators and Potential Therapeutic Targets—An Updated View. *Mediators of Inflammation* 2013, 2013, 16 pages). In addition to the systemic activation of TLR4 in sepsis, other conditions and therapeutic modalities are now recognized which lead to systemic cytokine storm, that if not properly managed can lead to unacceptable side effects (Barrett, D. M.; Teachey, D. T.; Grupp, S. A., Toxicity management for patients receiving novel T-cell engaging therapies. *Current opinion in pediatrics* 2014, 26 (1), 43-49). While moderate systemic activation of pro-inflammatory cytokines is believed to be a beneficial mechanism employed by the immune system to fight off invading pathogens, more potent activation, as noted above can lead to unacceptable toxicity. The need to limit the systemic activation of the PRRs is well recognized in the field of vaccination, which routinely uses a PRR agonist as an adjuvant to boost the immune response to the administered antigen (Wu, T. Y. H., Strategies for designing synthetic immune agonists. *Immunology* 2016, 148 (4), 315-325). Many of the intended uses of a PRR/STING agonist are best accomplished by local activation at the intended site of action leading to a local activation of the immune response. For instance, in cancer patients, local activation refers to STING activation in the tumor microenvironment. When STING activation occurs in a local environment or disease tissue, therapeutic benefit of a STING agonist can be improved and unnecessary systemic production of proinflammatory cytokines can be reduced. This ratio of local (for instance in a tumor microenvironment or disease tissue) versus systemic cytokine production or concentration provides a means of quantifying the production of desired cytokines in disease tissue versus production of cytokines in the blood, plasma or serum.

As used herein the term "therapeutic index (TI)" means the ratio of local cytokine concentration in the targeted disease tissue versus that of non-disease tissue. For instance, in a disease such as cancer the target disease tissue would include a tumor microenvironment. For agonists intended for the treatment of cancer such as a solid tumor, the tumor tissue is considered the diseased tissue. For most purposes the non-diseased tissue that will be used to construct the TI is blood, serum or plasma. For the treatment of cancer, the TI is defined as the ratio of cytokines in the tumor microenvironment versus those detected in blood and/or plasma and/or serum. TI can be applied to individual cytokines or a number of pro-inflammatory cytokines as measured in the tumor microenvironment and blood and/or plasma and/or serum.

In some instances, a TI of 1 or less is considered unfavourable as it indicates that the STING agonist stimulates cytokine production with equal efficacy in both the tumor and blood. In some instances, a TI of 3 or greater is considered favourable, a TI of 10 or more is considered more favourable, a TI of 30 or more is considered very favourable and a TI of 100 or more is considered extremely favourable. As is understood by one skilled in the art, the concentration of various pro-inflammatory cytokines can be measured in disease tissue and blood and/or plasma and/or serum using a number of well know techniques.

In some embodiments, the concentration of cytokine in tumor is at least 100 fold, at least 200 fold, at least 300 fold, at least 400 fold, at least 500 fold, at least 1000 fold higher than the concentration of the cytokine in blood, serum and/or plasma after the administration of STING agonist.

As used herein the term "tumor microenvironment" is the cellular environment in which the tumor exists, including surrounding blood vessels, immune cells, fibroblasts, bone marrow-derived inflammatory cells, lymphocytes, signaling molecules and the extracellular matrix. The tumor and the surrounding microenvironment are closely related and may interact constantly.

As used herein the term "disease tissue" means any cells or tissue existing in a disease state, including but not limited to a tumor. As used herein, disease tissue will also include the tissue effected by disease as well as the cellular environment of the disease tissue including normal cells, molecules and blood vessels.

It is noted that serum and plasma are components of blood. When referring to components for testing; "blood", "serum" and "plasma" are used collectively and interchangeably herein as corresponding analysis will produce identical results.

As used here in "proinflammatory cytokine" or "inflammatory cytokine" means any signaling molecule (a cytokine) that act as immunomodulatory agents. Inflammatory cytokines include, but are not limited to, IFNβ, IFNα, interleukin-1 (IL-1), IL-12, and IL-18, IL-6. IL-10, tumor necrosis factor (TNF) (including TNF-α), interferon gamma (IFN-gamma), and granulocyte-macrophage colony stimulating factor and play an important role in mediating the innate immune response. Inflammatory cytokines are involved in the upregulation of inflammatory reactions and can be produced by broad range of cells, including immune cells like macrophages, B lymphocytes, T lymphocytes and mast cells, as well as endothelial cells, fibroblasts, and various stromal cells; a given cytokine may be produced by more than one type of cell.

The targeted delivery of anti-tumor agents to improve therapeutic index (TI) is a well-established principle in drug discovery. Typical methods employed for drug targeting are the attachment of a targeting moiety to the active drug and the formulation of the drug into a nanoparticle (NP) delivery system (Arias, J. L., Drug targeting strategies in cancer treatment: An overview. *Mini-Reviews in Medicinal Chemistry* 2011, 11 (1), 1-17 and Irvine, D. J.; Hanson, M. C.; Rakhra, K.; Tokatlian, T., Synthetic Nanoparticles for Vaccines and Immunotherapy. *Chemical Reviews* 2015, 115 (19), 11109-11146). These same principles have been proposed for PRR agonists and drug delivery NP formulations have been demonstrated in animal models for STING agonist (Hanson, M. C.; Crespo, M. P.; Abraham, W.; Moynihan, K. D.; Szeto, G. L.; Chen, S. H.; Melo, M. B.; Mueller, S.; Irvine, D. J., Nanoparticulate STING agonists are potent lymph node-targeted vaccine adjuvants. *Journal of Clinical Investigation* 2015, 125 (6), 2532-2546). Intra-tumoral injection is a method of targeted delivery that has achieved dramatic efficacy and improved TIs and has been demonstrated for both TLR and STING agonist (Hammerich, L.; Bhardwaj, N.; Kohrt, H. E.; Brody, J. D., In situ vaccination for the treatment of cancer. *Immunotherapy* 2016, 8 (3), 315-330 and Corrales, L.; Glickman, Laura H.; McWhirter, Sarah M.; Kanne, David B.; Sivick, Kelsey E.; Katibah, George E.; Woo, S.-R.; Lemmens, E.; Banda, T.; Leong, Justin J.; Metchette, K.; Dubensky, Thomas W., Jr.; Gajewski, Thomas F., Direct Activation of STING in the Tumor Microenvironment Leads to Potent and Systemic Tumor Regression and Immunity. *Cell Reports* 2015, 11 (7), 1018-1030).

Unlike the examples of targeted delivery noted above, this invention provides methods of systemically administering a STING agonist that does not require the addition of a targeting moiety, the use of a NP formulation or direct intra-tumoral (i.t.) injection. In order for a STING agonist to achieve T cell activation in the tumor microenvironment, the STING agonist needs to demonstrate adequate cellular permeability and improved pharmacokinetics and distribution.

The endogenous mammalian ligand for STING is 2'3'-cGAMP, a cyclic dinucleotide possessing two phosphodiester groups. Due to the poor membrane permeability of 2'3'-cGAMP the compound has little to no activity in cellular assays even at very high concentrations. To overcome this limitation membrane permeability enhancers are often added to permit the use of CDNs is used in cellular assays (Yildiz, S.; Alpdundar, E.; Gungor, B.; Kahraman, T.; Bayyurt, B.; Gursel, I.; Gursel, M., Enhanced immunostimulatory activity of cyclic dinucleotides on mouse cells when complexed with a cell-penetrating peptide or combined with CpG. *European Journal of Immunology* 2015, 45 (4), 1170-1179). A second limitation of available STING agonist is the short serum half-life, which is believed to be the result rapid cleavage of the 2'5'-phosphdiester linkage (Li, L.; Yin, Q.; Kuss, P.; Maliga, Z.; Millán, J. L.; Wu, H.; Mitchison, T. J., Hydrolysis of 2'3'-cGAMP by ENPP1 and design of nonhydrolyzable analogs. *Nat Chem Biol* 2014, 10 (12), 1043-1048). Often the rate of phosphodiester cleavage can be slowed by replacement of oxygen with sulfur in the dative double bond of the phosphate. While introduction of sulfur into both of the phosphates of 2'3'-cGAMP was shown to improve serum and phosphodiesterase stability, the resulting CDN was still only weakly active in a cellular assay monitoring IFNβ synthesis (IC50~30 uM) versus as IC50 of >100 uM for 2'3'-cGAMP (Supplemental FIG. 13 from Li, L., et al. in *Nat Chem Biol* 2014).

Consistent with these limitations, there are very few reports of in vivo activity following the systemic (i.v. or i.p.) administration of CDN STING agonist. Li, T., et al. were able to demonstrate some efficacy using 20 daily i.v. doses of 20 mg/kg 2',3'-cGAMP in the CT26 syngeneic model if 2',3'-cGAMP was dosed 4 h after injection of the tumor cells (Li, T.; Cheng, H.; Yuan, H.; Xu, Q.; Shu, C.; Zhang, Y.; Xu, P.; Tan, J.; Rui, Y.; Li, P.; Tan, X., Antitumor Activity of cGAMP via Stimulation of cGAS-cGAMP-STING-IRF3 Mediated Innate Immune Response. *Scientific Reports* 2016, 6, 19049). However, the same treatment was significantly less active when given to animals with established tumors. In order to achieve robust anti-tumor activity investigators have turned to direct injection of the STING agonist into the tumor (intra-tumoral injection or i.t. as noted above) (Corrales, et al. Supra).

DMXAA is an example of STING agonist that potently inhibits tumor growth, leading to cures in mice, when administered once at the maximally tolerated i.p. dose of 500 ug/mouse (~99 uMol/kg) in the CT26 syngeneic model with established tumors. When dosed in this manner DMXAA generates high cytokine levels both in the tumor and the blood. By careful optimization of various systemic dosing protocols, researchers were able to achieve good oral activity in mice, but only at doses that generated high systemic cytokine levels and only in rodents that have a much higher tolerance levels for pro-inflammatory cytokines (Zhao, L.; Kestell, P.; Ching, L. M.; Baguley, B. C., Oral activity and pharmacokinetics of 5, 6-dimethylxanthenone-4-acetic acid (DMXAA) in mice. *Cancer Chemother Pharmacol* 2002, 49 (1), 20-26). DMXAA was extensively investigated as an anti-cancer agent in human clinical trials, but failed to provide sufficient efficacy and was discontinued. While DMXAA did not induce high levels of systemic cytokines in humans, it was later found to be active as a STING agonist only in mice and no other species (Conlon, J.; Burdette, D. L.; Sharma, S.; Bhat, N.; Thompson, M.; Jiang, Z.; Rathinam, V. A. K.; Monks, B.; Jin, T.; Xiao, T. S.; Vogel, S. N.; Vance, R. E.; Fitzgerald, K. A., Mouse, but not Human STING, Binds and Signals in Response to the Vascular Disrupting Agent 5,6-Dimethylxanthenone-4-Acetic Acid. *The Journal of Immunology* 2013, 190 (10), 5216-5225). Hence the activity that was seen in humans was not the result of STING agonism, but from other vasculature disrupting effects (Baguley, B. C.; McKeage, M. J., ASA404: A tumor vascular-disrupting agent with broad potential for cancer therapy. *Future Oncology* 2010, 6 (10), 1537-1543).

The present invention provides methods of systemically administering a STING agonist to a human in need thereof wherein the STING agonist increases at least one cytokine in disease tissue but does not cause increases or pro-inflammatory cytokines in the blood of said human to a level that causes adverse effects.

Thus, in one embodiment the present invention provides methods of treating cancer in a human comprising systemically administering a STING agonist to said human, wherein the STING agonist induces a higher concentration of at least one cytokine in a tumor microenvironment of said human compared with the concentration of said cytokine in the blood, serum and/or plasma of said human.

In one aspect, the cytokine is selected from IL-6, TNFα, IFNβ, and IFNγ. In one embodiment, the target index (TI) is 3 or greater for a selected cytokine. In one embodiment, the TI is 10 or greater for a selected cytokine. Thus, the TI for any given cytokine can be in the range of from about 3 to about 10, from about 3 to about 100, from about 3 to about 1000 to over 1000. As the TI represents a ratio of cytokine concentration in the disease tissue versus blood or serum, the TI can be represented by any integer or fraction thereof, with a TI of greater than about 3 considered favourable.

In one embodiment, the STING agonist increases the concentration of IL-6 at least three times as much in the tumor microenvironment or disease tissue in said human compared with the concentration of IL-6 levels in the blood of said human. In one embodiment, the STING agonist increases the concentration of TNFα at least three times as much in the tumor microenvironment or disease tissue in said human compared with the concentration of TNFα levels in the blood or said human. In one embodiment, the STING agonist increases the concentration of IFNβ at least three times as much in the tumor microenvironment or disease tissue in said human compared with the concentration of IFNβ levels in the blood of said human. In one embodiment, the STING agonist increases concentration IFNγ at least three times as much in the tumor microenvironment or disease tissue in said human compared with the concentration of IFNγ levels in the blood of said human.

In yet another embodiment. the STING agonist has an IC50 of less than about 10 µM, in one aspect the STING agonist has an IC50 of less than about 1 µM; in one aspect the STING agonist has an IC50 of less than about 0.1 µM.

In one embodiment the STING agonist provides an AUC (0-24) of at the range (850-1060 ng·hr/ml) when administered systemically to said human.

In one embodiment, the STING agonist has a significantly higher Cmax concentration in a tumor microenvironement of said human compared with blood, serum and/or plasma of said human. In one embodiment, the STING agonist has a significantly higher Cmax concentration in a tumor microenvironement of said human compared with blood, serum or plasma of said human. The term "significantly higher" suitably refers to a 2 fold increase, suitably a 3 fold increase, suitably a 10 fold increase, suitably a 100 fold increase, suitably more than a 100 fold increase.

In one embodiment, the half-life of said STING agonist is significantly longer in a tumor microenvironment of said human compared with the blood, serum and/or plasma of said human. In one embodiment, the half-life of said STING agonist is significantly longer in a tumor microenvironment of said human compared with the blood, serum or plasma of said human. The term "significantly longer" suitably refers to a 2 fold increase, suitably a 3 fold increase, suitably a 10 fold increase, suitably a 100 fold increase, suitably more than a 100 fold increase.

As used herein "Area Under the Curve" or "AUC" is used to describe both pharmacokinetic parameters and tumor volume. When used to describe pharmacokinetic drug concentration, AUC refers to the area under the curve in a plot of the concentration of a substance in plasma against time. AUC can be a measure of the integral of the instantaneous concentrations during a time interval and has the units mass×time/volume, which can also be expressed as molar concentration×time such as nM×day. AUC is typically calculated by the trapezoidal method (e.g., linear, linear-log). AUC is usually given for the time interval zero to infinity, and other time intervals are indicated (for example AUC (t1,t2) where t1 and t2 are the starting and finishing times for the interval). Thus, as used herein "$AUC_{0-24h}$" refers to an AUC over a 24-hour period, and "$AUC_{0-12h}$" refers to an AUC over a 12-hour period. Similarly, AUC can also be used to describe tumor volume over time. When used to describe tumor volume, the size of a tumor is plotted against time.

As used herein "weighted mean AUC" is the AUC divided by the time interval over which the time AUC is calculated. For instance, weighted mean $AUC_{0-24h}$ would represent the $AUC_{0-24h}$ divided by 24 hours.

In one embodiment, the STING agonist provides a mean Cmax with the range of (1900-3800 ng/ml) of said STING agonist when administered to said human.

As used herein "maximum plasma concentration" or "Cmax" means the highest observed concentration of a substance (for example, a STING agonist) in mammalian plasma after administration of the substance to the mammal.

As used herein "confidence interval" or "CI" is an interval in which a measurement or trial falls corresponding to a given probability p where p refers to a 90% or 95% CI and are calculated around either an arithmetic mean, a geometric mean, or a least squares mean. As used herein, a geometric mean is the mean of the natural log-transformed values back-transformed through exponentiation, and the least squares mean may or may not be a geometric mean as well but is derived from the analysis of variance (ANOVA) model using fixed effects.

As used herein the "coefficient of variation (CV)" is a measure of dispersion and it is defined as the ratio of the standard deviation to the mean. It is reported as a percentage (%) by multiplying the above calculation by 100 (% CV).

As used herein "Tmax" refers to the observed time for reaching the maximum concentration of a substance in plasma of a mammal after administration of that substance to the mammal.

As used herein "blood" and/or "serum" and/or "plasma" "half-life" or "terminal half-life" refers to the time required for half the quantity of a substance administered to a mammal to be metabolized or eliminated correspondingly from the blood, serum or plasma of the mammal by normal biological processes.

The one embodiment, the STING agonist has a significantly higher Cmax concentration in the tumor microenvironement of said human compared with blood, serum and/or plasma of said human. In another embodiment, the half-life of said STING agonist is significantly longer in the tumor microenvironment of said human compared with the blood, serum and/or plasma of said human. In one aspect, the STING agonist is administered intravenously. As is understood in the art, several known methods are available to measure drug concentration in the tumor microenvironment and the blood, serum, and/or plasma of a mammal. Additionally, several statistical methods are well known for measuring statistically significant differences in pharmacokinetic parameters.

In one embodiment, the STING agonist is administered to the human via a route selected from intravenously, subcutaneously, transdermally, intramuscularly, and orally. In one embodiment, the STING agonist is administered intravenously.

One embodiment of the invention relates to a STING agonist, or a pharmaceutically acceptable salt thereof for use in the treatment of cancer wherein the STING agonist is systemically administered.

One embodiment of the invention relates to the use of a STING agonist, or a pharmaceutically acceptable salt thereof in the manufacture of a medicament for the treatment of cancer wherein the STING agonist is systemically administered.

One embodiment of the invention relates to a pharmaceutical composition for systemic administration comprising a STING agonist, or a pharmaceutically acceptable salt thereof.

One embodiment of the invention relates to a pharmaceutical composition for systemic administration comprising a STING agonist, or a pharmaceutically acceptable salt thereof for use in the treatment of cancer.

In one embodiment, the STING agonist is a compound according to Formula (I-N):

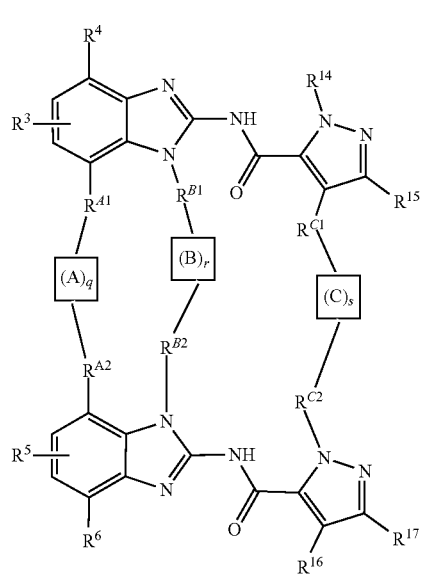

(I-N)

wherein:
q is 0 or 1;
r is 0 or 1;
s is 0 or 1;
wherein q+r+s=1 or 2;
when q is 0, $R^{A1}$ and $R^{A2}$ are each independently H, halogen, hydroxy, —O—P(O)(OH)$_2$, —O—P(O)($R^I R^{II}$)$_2$, —N($R^e$)($R^f$), —CO$_2 R^f$, —N($R^f$)COR$^b$, —N($R^g$)SO$_2$(C$_1$-C$_4$alkyl)-N($R^e$)($R^f$), —N($R^g$)CO(C$_1$-C$_4$alkyl)-N($R^h$)($R^f$), optionally substituted (C$_1$-C$_6$alkyl), optionally substituted (C$_1$-C$_6$alkyl)oxy-, optionally substituted (C$_1$-C$_6$alkyl)amino-, and optionally substituted (C$_1$-C$_6$alkyl)(C$_1$-C$_4$alkyl)amino-, wherein the (C$_1$-C$_6$alkyl) of said optionally substituted (C$_1$-C$_6$alkyl), optionally substituted (C$_1$-C$_6$alkyl)oxy-, optionally substituted (C$_1$-C$_6$alkyl)amino- and optionally substituted (C$_1$-C$_6$alkyl)(C$_1$-C$_4$alkyl)amino- is optionally substituted by 1-4 substituents each independently selected from hydroxy, —O—P(O)(OH)$_2$, —O—P(O)($R^I R^{II}$)$_2$, C$_1$-C$_4$alkoxy-, —N($R^e$)($R^f$), —CO$_2$($R^f$), —CON($R^e$)($R^f$), optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, —O—P(O)(OH)$_2$, —O—P(O)($R^I R^{II}$)$_2$, amino, (C$_1$-C$_6$alkyl)amino-, (C$_1$-C$_6$alkyl)(C$_1$-C$_6$alkyl)amino-, —(C$_1$-C$_6$alkyl)-NH$_2$, halo(C$_1$-C$_6$alkyl), hydroxy-(C$_1$-C$_4$alkyl)-, —(C$_1$-C$_4$alkyl)-O—P(O)(OH)$_2$, —(C$_1$-C$_4$alkyl)-O—P(O)($R^I R^{II}$)$_2$, halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$, —(C$_2$-C$_4$alkoxy)-O—P(O)($R^I R^{II}$)$_2$, —C$_1$-C$_4$alkyl-(C$_1$-C$_4$alkoxy) and C$_1$-C$_4$alkoxy-(C$_1$-C$_4$alkoxy)-;

when r is 0, $R^{B1}$ and $R^{B2}$ are each independently H, optionally substituted C$_1$-C$_6$alkyl, halo(C$_1$-C$_6$alkyl), optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted phenyl, optionally substituted 5-6 membered heteroaryl, or optionally substituted 9-10 membered heteroaryl, wherein said optionally substituted C$_1$-C$_6$alkyl, optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted phenyl, optionally substituted 5-6 membered heteroaryl, or optionally substituted 9-10 membered heteroaryl is optionally substituted by 1-4 substituents each independently selected from halogen, nitro, —R$^c$, —OH, —O—P(O)(OH)$_2$, —O—P(O)(RIRII)$_2$, —OR$^c$, —NH$_2$, —NR$^c$R$^c$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NRcR$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$;

when s is 0, $R^{C1}$ is H, halogen, or C$_1$-C$_4$alkyl and $R^{C2}$ is optionally substituted C$_1$-C$_4$alkyl, wherein said optionally substituted C$_1$-C$_4$alkyl group is optionally substituted by a substituent selected from —OR$^c$, —NR$^c$R$^d$, —CO$_2$R$^c$, —CONR$^c$R$^d$, —SO$_2$NR$^c$R$^d$, and —OCONR$^c$R$^d$;

when q is 1, $R^{A1}$ and $R^{A2}$ are each independently —CH$_2$—, —NR$^e$—, or —O—, and A, taken together with $R^{A1}$ and $R^{A2}$, forms a linking group, wherein A is -halo(C$_1$-C$_2$alkyl)-, optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl-, wherein the alkyl moiety of said optionally substituted —C$_1$-C$_2$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1-4 substituents each independently selected from halogen, halo(C$_1$-C$_4$alkyl), —OH, —O—P(O)(OH)$_2$, —O—P(O)(R$_I$R$_{II}$)$_2$, —OR$^c$, —NH$_2$, —NRcR$^d$, —OCOR$^c$, —CO$_2$H, —CO$_2$R$^c$, —SOR$^c$, —SO$_2$R$^c$, —CONH$_2$, —CONRcR$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the C$_3$-C$_6$cycloalkyl, phenyl, 4-6 membered heterocycloalkyl, or 5-6 membered heteroaryl moiety of said optionally substituted —C$_1$-C$_6$alkyl-(C$_3$-

$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, hydroxy, —O—P(O)(OH)$_2$, —O—P(O)($R^I R^H$)$_2$, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_1$-$C_4$alkoxy)-, —($C_1$-$C_4$alkoxyl)-O—P(O)(OH)$_2$, —($C_1$-$C_4$alkoxyl)-O—P(O)($R^I R^H$)$_2$ and $C_1$-$C_4$alkoxy-($C_1$-$C_4$alkoxy)-;

when r is 1, $R^{B1}$ and $R^{B2}$ are each independently —CH$_2$—, and B, taken together with $R^{B1}$ and $R^{B2}$, forms a linking group, wherein B is a bond or B is -halo($C_1$-$C_{10}$alkyl)-, optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-NR$^a$—$C_1$-$C_6$alkyl-, optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl-, wherein the alkyl moiety of said optionally substituted —$C_1$-$C_{10}$alkyl-, optionally substituted —$C_2$-$C_{10}$alkenyl-, optionally substituted —$C_2$-$C_{10}$alkynyl-, optionally substituted —$C_1$-$C_6$alkyl-O—$C_1$-$C_6$alkyl-, optionally substituted —$C_1$-$C_6$alkyl-NR—$C_1$-$C_6$alkyl-, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl-$C_1$-$C_4$alkyl)- is optionally substituted by 1 or 2 substituents each independently selected from halogen, halo($C_1$-$C_4$alkyl), —OH, —O—P(O)(OH)$_2$, —O—P(O)($R^I R^H$)$_2$, —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the $C_3$-$C_6$cycloalkyl, phenyl, 4-6 membered heterocycloalkyl, or 5-6 membered heteroaryl moiety of said optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl- is optionally substituted by 1-4 substituents each independently selected from halogen, hydroxy, —O—P(O)(OH)$_2$, —O—P(O)($R^I R^H$)$_2$, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, —($C_2$-$C_4$alkoxy) O—P(O)(OH)$_2$, —($C_2$-$C_4$alkoxy)-O—P(O)($R^I R^H$)$_2$, and $C_1$-$C_4$alkoxy-($C_1$-$C_4$alkoxy)-;

when s is 1, $R^{C1}$ and $R^{C2}$ are each independently —CH$_2$—, and C, taken together with $R^{C1}$ and $R^{C2}$, forms a linking group, wherein C is -halo($C_1$-$C_2$alkyl)-, optionally substituted —$C_1$-$C_{12}$alkyl-, optionally substituted —$C_2$-$C_{12}$alkenyl-, optionally substituted —$C_2$-$C_{12}$alkynyl-, optionally substituted —$C_1$-$C_6$alkyl-O—$C_1$-$C_6$alkyl-, optionally substituted —$C_1$-$C_6$alkyl-NR—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl-, wherein the alkyl moiety of said optionally substituted —$C_1$-$C_{12}$alkyl-, optionally substituted —$C_2$-$C_{12}$alkenyl-, optionally substituted —$C_2$-$C_{12}$alkynyl-, optionally substituted —$C_1$-$C_6$alkyl-O—$C_1$-$C_6$alkyl-, optionally substituted —$C_1$-$C_6$alkyl-NR—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1 or 2 substituents each independently selected from halogen, halo($C_1$-$C_4$alkyl), —OH, —O—P(O)(OH)$_2$, —O—P(O)($R^I R^H$)$_2$, —OR$^c$, —NH$_2$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, and the $C_3$-$C_6$cycloalkyl, phenyl, 4-6 membered heterocycloalkyl, or 5-6 membered heteroaryl moiety of said optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, hydroxy, —O—P(O)(OH)$_2$, —O—P(O)($R^I R^H$)$_2$, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, —($C_2$-$C_4$alkoxy)-O—P(O)(OH)$_2$, —($C_2$-$C_4$alkoxy)-O—P(O)($R^I R^H$)$_2$, and $C_1$-$C_4$alkoxy-($C_1$-$C_4$alkoxy)-;

$R^3$ and $R^5$ are each independently —CON($R^d$)($R^f$), or one of $R^3$ and $R^5$ is —CON($R^d$)($R^f$), and the other of $R^3$ and $R^5$ is H, COOH or —CO$_2$($R^c$);

$R^4$ and $R^6$ are each independently selected from H, halogen, halo($C_1$-$C_6$alkyl), halo($C_1$-$C_6$alkoxy)-, hydroxy, —O—P(O)(OH)$_2$, —O—P(O)($R^I R^H$)$_2$, —NH$_2$, —NR$^c$R$^c$, —NR$^c$R$^d$, —COR$^c$, —CO$_2$R$^c$, —N($R^d$)COR$^c$, —N($R^d$)SO$_2$R$^c$, —N($R^g$)SO$_2$($C_1$-$C_2$alkyl)-N($R^h$)($R^f$), —N($R^g$)CO($C_1$-$C_2$alkyl)-N($R^h$)($R^f$), optionally substituted ($C_1$-$C_6$alkyl), optionally substituted ($C_1$-$C_6$alkyl)oxy-, optionally substituted ($C_1$-$C_6$alkyl)amino-, and optionally substituted ($C_1$-$C_6$alkyl)($C_1$-$C_4$alkyl)amino-, wherein the ($C_1$-$C_6$alkyl) of said optionally substituted ($C_1$-$C_6$alkyl), optionally substituted ($C_1$-$C_6$alkyl)oxy-, optionally substituted (C₁-C₆alkyl)amino- and optionally substituted (C₁-C₆alkyl)(C₁-C₄alkyl)amino- is optionally substituted by 1-4 substituents each independently selected from —OH, —O—P(O)(OH)₂, —O—P(O)(R$^I$R$^{II}$)₂, —OR$^c$, —NH₂, —NR$^c$R$^d$, —NR$^c$R$^d$, —CO₂H, —CO₂R$^c$, —OCOR$^c$, —CO₂H, —CO₂R$^c$, —SOR$^c$, —SO₂R$^c$, —CONH₂, —CONR$^c$R$^d$, —SO₂NH₂, —SO₂NR$^c$R$^d$, —OCONH₂, —OCONR$^c$R$^d$, —NR$^d$COR$^c$, —NR$^d$SOR$^c$, —NR$^d$CO₂R$^c$, —NR$^d$S2R$^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, —O—P(O)(OH)₂, —O—P(O)(R$^I$R$^{II}$)₂, amino, (C₁-C₄alkyl)amino-, (C₁-C₄alkyl)(C₁-C₄alkyl)amino-, C₁-C₄alkyl, halo(C₁-C₄alkyl), hydroxy-(C₁-C₄alkyl)-, —(C₁-C₄alkyl)-O—P(O)(OH)₂, —(C₁-C₄alkyl)-O—P(O)(R$^I$R$^{II}$)₂, halo(C₁-C₄alkoxy)-, C₁-C₄alkoxy-, hydroxy-(C₂-C₄alkoxy)-, —(C₂-C₄alkoxy)-O—P(O)(OH)₂, —(C₂-C₄alkoxy)-O—P(O)(R$^I$R$^{II}$)₂, C₁-C₄alkoxy-(C₁-C₄alkoxy)-, —COR$^d$, —CON(R$^d$)(R$^f$), and —CO₂R$^d$;

R¹⁴ is optionally substituted C₁-C₄alkyl, wherein said optionally substituted C₁-C₄alkyl is optionally substituted by a substituent selected from —OR$^c$, —NR$^c$R$^d$, —CO₂R$^c$, —CONR$^c$R$^d$, —SO₂NR$^c$R$^d$, and —OCONR$^c$R$^d$;

R¹⁶ is H, halogen, or C₁-C₄alkyl;

R¹⁵ and R¹⁷ are each independently H, cyclopropyl, or C₁-C₄alkyl;

R$^a$ is H, —R$^c$, —COR$^c$, —CO₂H, —CO₂R$^c$, —SOR$^c$, —SO₂R$^c$, —CONH₂, —CONR$^c$R$^d$, —SO₂NH₂, or —SO₂NR$^c$R$^d$;

each R$^b$ is independently C₁-C₄alkyl, halo(C₁-C₄alkyl), —(C₁-C₄alkyl)-OH, —(C₁-C₄alkyl)-O—P(O)(OH)₂, —(C₁-C₄alkyl)-O—P(O)(R$^I$R$^{II}$)₂, —(C₁-C₄alkyl)-O—(C₁-C₄alkyl), —(C₁-C₄alkyl)-N(R$^e$)(R$^f$), —(C₁-C₄alkyl)-O—CO(C₁-C₄alkyl), or —(C₁-C₄alkyl)-CO—O—(C₁-C₄alkyl);

each R$^c$ is independently C₁-C₄alkyl, halo(C₁-C₄alkyl), —(C₁-C₄alkyl)-OH, —(C₁-C₄alkyl)-O—P(O)(OH)₂, —(C₁-C₄alkyl)-O—P(O)(R$^I$R$^{II}$)₂, —(C₁-C₄alkyl)-O—(C₁-C₄alkyl), —(C₁-C₄alkyl)-N(R$^e$)(R$^f$), —(C₁-C₄alkyl)-O—CO(C₁-C₄alkyl), —(C₁-C₄alkyl)-CO—O—(C₁-C₄alkyl), optionally substituted C₃-C₆cycloalkyl, optionally substituted phenyl, optionally substituted 4-6 membered heterocycloalkyl, optionally substituted 5-6 membered heteroaryl, optionally substituted 9-10 membered heteroaryl, optionally substituted —C₁-C₄alkyl-C₃-C₆cycloalkyl, optionally substituted —C₁-C₄alkyl-phenyl, optionally substituted —C₁-C₄alkyl-4-6 membered heterocycloalkyl, optionally substituted —C₁-C₄alkyl-5-6 membered heteroaryl, or optionally substituted —C₁-C₄alkyl-9-10 membered heteroaryl, wherein the C₃-C₆cycloalkyl, phenyl, 4-6 membered heterocycloalkyl, 5-6 membered heteroaryl or optionally substituted 9-10 membered heteroaryl moiety of said substituted C₃-C₆cycloalkyl, optionally substituted phenyl, optionally substituted 4-6 membered heterocycloalkyl, optionally substituted 5-6 membered heteroaryl, optionally substituted 9-10 membered heteroaryl optionally substituted —C₁-C₄alkyl-C₃-C₆cycloalkyl, optionally substituted —C₁-C₄alkyl-phenyl, optionally substituted —C₁-C₄alkyl-4-6 membered heterocycloalkyl, optionally substituted —C₁-C₄alkyl-5-6 membered heteroaryl, or optionally substituted —C₁-C₄alkyl-9-10 membered heteroaryl is optionally substituted by 1-4 substituents each independently selected from halogen, hydroxy, —O—P(O)(OH)₂, —O—P(O)(R$^I$R$^{II}$)₂, amino, —(C₁-C₄alkyl)NH₂, (C₁-C₄alkyl)amino-, (C₁-C₄alkyl)(C₁-C₄alkyl)amino-, —C₁-C₄alkyl, halo(C₁-C₄alkyl), halo(C₁-C₄alkoxy)-, C₁-C₄alkoxy-, hydroxy-(C₂-C₄alkoxy)-, —(C₂-C₄alkoxy)-O—P(O)(OH)₂, —(C₂-C₄alkoxy)-O—P(O)(R$^I$R$^{II}$)₂, C₁-C₄alkoxy-(C₁-C₄alkoxy)-, —COR$^d$, —CON(R$^d$)(R$^f$), and —CO₂R$^d$;

each R$^d$ is independently H or C₁-C₄alkyl;

each R$^e$ is independently H, C₁-C₄alkyl, —CO(C₁-C₄alkyl), —OCO(C₁-C₄alkyl), —CO₂(C₁-C₄alkyl), —(C₁-C₄alkyl)NH₂, —(C₁-C₄alkyl) C₁-C₄alkoxy, —CO-(optionally substituted 5-6 membered heterocycloalkyl), —CO(C₁-C₄alkyl)-(optionally substituted 5-6 membered heterocycloalkyl), —CO (optionally substituted 5-6 membered heteroaryl), —CO(C₁-C₄alkyl)-(optionally substituted 5-6 membered heteroaryl), wherein the optionally substituted 5-6 membered heterocycloalkyl or optionally substituted 5-6 membered heteroaryl is optionally substituted 1-4 substituents each independently selected from halogen, hydroxy, —O—P(O)(OH)₂, —O—P(O)(R$^I$R$^{II}$)₂, amino, (C₁-C₄alkyl)amino-, (C₁-C₄alkyl)(C₁-C₄alkyl)amino-, C₁-C₄alkyl, halo(C₁-C₄alkyl), halo(C₁-C₄alkoxy)-, C₁-C₄alkoxy-, hydroxy-(C₂-C₄alkoxy)-, —(C₂-C₄alkoxy) O—P(O)(OH)₂, —(C₂-C₄alkoxy)-O—P(O)(R$^I$R$^{II}$)₂, C₁-C₄alkoxy-(C₁-C₄alkoxy)-, —COR$^d$, —CON(R$^d$)(R$^f$), and —CO₂R$^d$;

each R$^f$ is independently H or C₁-C₄alkyl;

R$^g$ and R$^h$ are each independently H or C₁-C₄alkyl or R$^g$ and R$^h$, taken together with the atom or atoms through which they are connected, form a 5-6 membered ring;

and each occurrence of R$^I$ and R$^{II}$ are independently (C₁-C₆alkyl)oxy-;

or a pharmaceutically acceptable salt thereof.

In one embodiment, the STING agonist or a pharmaceutically acceptable salt thereof has the structure of Formula (I)

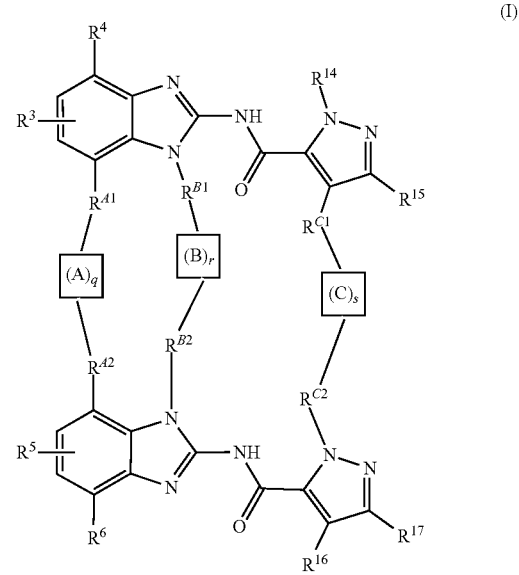

(I)

wherein:
  q is 0 or 1;
  r is 0 or 1;
  s is 0 or 1;
  wherein q+r+s=1 or 2;
  when q is 0, $R^{A1}$ and $R^{A2}$ are each independently H, halogen, hydroxy, —N($R^e$)($R^f$), —CO$_2R^f$, —N($R^f$)COR$^b$, —N($R^g$)SO$_2$(C$_1$-C$_4$alkyl)-N($R^e$)($R^f$), —N($R^g$)CO(C$_1$-C$_4$alkyl)-N($R^h$)($R^f$), optionally substituted (C$_1$-C$_6$alkyl), optionally substituted (C$_1$-C$_6$alkyl)oxy-, optionally substituted (C$_1$-C$_6$alkyl)amino-, and optionally substituted (C$_1$-C$_6$alkyl)(C$_1$-C$_4$alkyl)amino-,
  wherein the (C$_1$-C$_6$alkyl) of said optionally substituted (C$_1$-C$_6$alkyl), optionally substituted (C$_1$-C$_6$alkyl)oxy-, optionally substituted (C$_1$-C$_6$alkyl)amino- and optionally substituted (C$_1$-C$_6$alkyl)(C$_1$-C$_4$alkyl)amino- is optionally substituted by 1-4 substituents each independently selected from hydroxy, C$_1$-C$_4$alkoxy-, —N($R^e$)($R^f$), —CO$_2$($R^f$), —CON($R^e$)($R^f$), optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, amino, (C$_1$-C$_6$alkyl)amino-, (C$_1$-C$_6$alkyl)(C$_1$-C$_6$alkyl)amino-, halo(C$_1$-C$_6$alkyl), hydroxy-(C$_1$-C$_4$alkyl)-, halo(C$_1$-C$_4$alkoxy)-, C$_1$-C$_4$alkoxy-, hydroxy-(C$_2$-C$_4$alkoxy)-, and C$_1$-C$_4$alkoxy-(C$_1$-C$_4$alkoxy)-;
  when r is 0, $R^{B1}$ and $R^{B2}$ are each independently H, optionally substituted C$_1$-C$_6$alkyl, halo(C$_1$-C$_6$alkyl), optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted phenyl, optionally substituted 5-6 membered heteroaryl, or optionally substituted 9-10 membered heteroaryl,
  wherein said optionally substituted C$_1$-C$_6$alkyl, optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted phenyl, optionally substituted 5-6 membered heteroaryl, or optionally substituted 9-10 membered heteroaryl is optionally substituted by 1-4 substituents each independently selected from halogen, nitro, —$R^c$, —OH, —OR$^c$, —NH$_2$, —NR$^cR^c$, —NR$^cR^d$, —OCOR$^c$, —CO$_2$H, —CO$_2R^c$, —SOR$^c$, —SO$_2R^c$, —CONH$_2$, —CONR$^cR^d$, —SO$_2$NH$_2$, —SO$_2$NR$^cR^d$, —OCONH$_2$, —OCONR$^cR^d$, —NR$^d$COR$^c$, —NR$^d$SOR$^c$, —NR$^d$CO$_2R^c$, and —NR$^d$SO$_2R^c$;
  when s is 0, $R^{C1}$ is H, halogen, or C$_1$-C$_4$alkyl and $R^{C2}$ is optionally substituted C$_1$-C$_4$alkyl, wherein said optionally substituted C$_1$-C$_4$alkyl group is optionally substituted by a substituent selected from —OR$^c$, —NR$^cR^d$, —CO$_2R^c$, —CONR$^cR^d$, —SO$_2$NR$^cR^d$, and —OCONR$^cR^d$;
  when q is 1, $R^{A1}$ and $R^{A2}$ are each independently —CH$_2$—, —NR$^e$—, or —O—, and A, taken together with $R^{A1}$ and $R^{A2}$, forms a linking group, wherein A is -halo(C$_1$-C$_2$alkyl)-, optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl-,
  wherein the alkyl moiety of said optionally substituted —C$_1$-C$_{12}$alkyl-, optionally substituted —C$_2$-C$_{12}$alkenyl-, optionally substituted —C$_2$-C$_{12}$alkynyl-, optionally substituted —C$_1$-C$_6$alkyl-O—C$_1$-C$_6$alkyl-, optionally substituted —C$_1$-C$_6$alkyl-NR—C$_1$-C$_6$alkyl-, optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1-4 substituents each independently selected from halogen, halo(C$_1$-C$_4$alkyl), —OH, —OR$^c$, —NH$_2$, —NR$^cR^d$, —OCOR$^c$, —CO$_2$H, —CO$_2R^c$, —SOR$^c$, —SO$_2R^c$, —CONH$_2$, —CONR$^cR^d$, —SO$_2$NH$_2$, —SO$_2$NR$^cR^d$, —OCONH$_2$, —OCONR$^cR^d$, —NR$^d$COR$^c$, —NR$^d$SOR$^c$, —NR$^d$CO$_2R^c$, and —NR$^d$SO$_2R^c$,
  and
  the C$_3$-C$_6$cycloalkyl, phenyl, 4-6 membered heterocycloalkyl, or 5-6 membered heteroaryl moiety of said optionally substituted —C$_1$-C$_6$alkyl-(C$_3$-C$_6$cycloalkyl)-C$_1$-C$_6$alkyl-, optionally substituted —C$_1$-C$_6$alkyl-phenyl-C$_1$-C$_6$alkyl-, optionally substituted —C$_1$-C$_6$alkyl-(4-6 membered heterocycloalkyl)-C$_1$-C$_6$alkyl-, or optionally substituted —C$_1$-C$_6$alkyl-(5-6 membered heteroaryl)-C$_1$-C$_6$alkyl- is optionally substituted by 1-4 substituents each independently selected from halogen, hydroxy, amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_2$-C$_4$alkoxy)-, and C$_1$-C$_4$alkoxy-(C$_1$-C$_4$alkoxy)-;
  when r is 1, $R^{B1}$ and $R^{B2}$ are each independently —CH$_2$—, and B, taken together with $R^{B1}$ and $R^{B2}$, forms a linking group, wherein B is a bond or B is -halo(C$_1$-C$_{10}$alkyl)-, optionally substituted —C$_1$-C$_{10}$alkyl-, optionally substituted —C$_2$-C$_{10}$alkenyl-, optionally substituted —C$_2$-C$_{10}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted C$_3$-C$_6$cycloalkyl, optionally substituted phenyl, optionally substituted 4-6 membered heterocycloalkyl, optionally substituted 5-6 membered heteroaryl, optionally substituted —C$_1$-C$_4$alkyl-(C$_3$-C$_6$cycloalkyl)-C$_1$-C$_4$alkyl-, optionally substituted —C$_1$-C$_4$alkyl-phenyl-C$_1$-C$_4$alkyl-, optionally substituted —C$_1$-C$_4$alkyl-(4-6 membered heterocycloalkyl)-C$_1$-C$_4$alkyl-, or optionally substituted —C$_1$-C$_4$alkyl-(5-6 membered heteroaryl)-C$_1$-C$_4$alkyl-,
  wherein the alkyl moiety of said optionally substituted —C$_1$-C$_{10}$alkyl-, optionally substituted —C$_2$-C$_{10}$alkenyl-, optionally substituted —C$_2$-C$_{10}$alkynyl-, optionally substituted —C$_1$-C$_6$alkyl-O—C$_1$-C$_6$alkyl-, optionally substituted —C$_1$-C$_6$alkyl-NR$^a$—C$_1$-C$_6$alkyl-, optionally substituted —C$_1$-C$_4$alkyl-(C$_3$-C$_6$cycloalkyl)-C$_1$-C$_4$alkyl-, optionally substituted —C$_1$-C$_4$alkyl-phenyl-C$_1$-C$_4$alkyl-, optionally substituted —C$_1$-C$_4$alkyl-(4-6 membered heterocycloalkyl)-C$_1$-C$_4$alkyl-, or optionally substituted —C$_1$-C$_4$alkyl-(5-6 membered heteroaryl-C$_1$-C$_4$alkyl)- is optionally substituted by 1 or 2 substituents each independently selected from halogen, halo($C_1$-$C_4$alkyl), —OH, —$OR^c$, —$NH_2$, —$NR^cR^d$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, and —$NR^dSO_2R^c$, and the $C_3$-$C_6$cycloalkyl, phenyl, 4-6 membered heterocycloalkyl, or 5-6 membered heteroaryl moiety of said optionally substituted $C_3$-$C_6$cycloalkyl, optionally substituted phenyl, optionally substituted 4-6 membered heterocycloalkyl, optionally substituted 5-6 membered heteroaryl, optionally substituted —$C_1$-$C_4$alkyl-($C_3$-$C_6$cycloalkyl)-$C_1$-$C_4$alkyl-, optionally substituted —$C_1$-$C_4$alkyl-phenyl-$C_1$-$C_4$alkyl-, optionally substituted —$C_1$-$C_4$alkyl-(4-6 membered heterocycloalkyl)-$C_1$-$C_4$alkyl-, or optionally substituted —$C_1$-$C_4$alkyl-(5-6 membered heteroaryl)-$C_1$-$C_4$alkyl- is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, and $C_1$-$C_4$alkoxy-($C_1$-$C_4$alkoxy)-;

when s is 1, $R^{C1}$ and $R^{C2}$ are each independently —$CH_2$—, and C, taken together with $R^{C1}$ and $R^{C2}$, forms a linking group, wherein C is -halo($C_1$-$C_2$alkyl)-, optionally substituted —$C_1$-$C_{12}$alkyl-, optionally substituted —$C_2$-$C_{12}$alkenyl-, optionally substituted —$C_2$-$C_{12}$alkynyl-, optionally substituted —$C_1$-$C_6$alkyl-O—$C_1$-$C_6$alkyl-, optionally substituted —$C_1$-$C_6$alkyl-NR—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl-, wherein the alkyl moiety of said optionally substituted —$C_1$-$C_{12}$alkyl-, optionally substituted —$C_2$-$C_{12}$alkenyl-, optionally substituted —$C_2$-$C_{12}$alkynyl-, optionally substituted —$C_1$-$C_6$alkyl-O—$C_1$-$C_6$alkyl-, optionally substituted —$C_1$-$C_6$alkyl-NR—$C_1$-$C_6$alkyl-, optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1 or 2 substituents each independently selected from halogen, halo($C_1$-$C_4$alkyl), —OH, —$OR^c$, —$NH_2$, —$NR^cR^d$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, and —$NR^dSO_2R^c$, and the $C_3$-$C_6$cycloalkyl, phenyl, 4-6 membered heterocycloalkyl, or 5-6 membered heteroaryl moiety of said optionally substituted —$C_1$-$C_6$alkyl-($C_3$-$C_6$cycloalkyl)-$C_1$-$C_6$alkyl-, optionally substituted —$C_1$-$C_6$alkyl-phenyl-$C_1$-$C_6$alkyl-, optionally substituted —$C_1$-$C_6$alkyl-(4-6 membered heterocycloalkyl)-$C_1$-$C_6$alkyl-, or optionally substituted —$C_1$-$C_6$alkyl-(5-6 membered heteroaryl)-$C_1$-$C_6$alkyl- is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, and $C_1$-$C_4$alkoxy-($C_1$-$C_4$alkoxy)-;

$R^3$ and $R^5$ are each independently —$CON(R^d)(R^f)$, or one of $R^3$ and $R^5$ is —$CON(R^d)(R^c)$, and the other of $R^3$ and $R^5$ is H or —$CO_2(R^c)$;

$R^4$ and $R^6$ are each independently selected from H, halogen, halo($C_1$-$C_6$alkyl), halo($C_1$-$C_6$alkoxy)-, hydroxy, —$NH_2$, —$NR^cR^c$, —$NR^cR^d$, —$COR^c$, —$CO_2R^c$, —$N(R^d)COR^c$, —$N(R^d)SO_2R^c$, —$N(R^g)SO_2(C_1$-$C_2$alkyl)-$N(R^h)(R^f)$, —$N(R^g)CO(C_1$-$C_2$alkyl)-$N(R^h)(R^f)$, optionally substituted ($C_1$-$C_6$alkyl), optionally substituted ($C_1$-$C_6$alkyl)oxy-, optionally substituted ($C_1$-$C_6$alkyl)amino-, and optionally substituted ($C_1$-$C_6$alkyl)($C_1$-$C_4$alkyl)amino-, wherein the ($C_1$-$C_6$alkyl) of said optionally substituted ($C_1$-$C_6$alkyl), optionally substituted ($C_1$-$C_6$alkyl)oxy-, optionally substituted ($C_1$-$C_6$alkyl)amino- and optionally substituted ($C_1$-$C_6$alkyl)($C_1$-$C_4$alkyl)amino- is optionally substituted by 1-4 substituents each independently selected from —OH, —$OR^c$, —$NH_2$, —$NR^cR^c$, —$NR^cR^d$, —$CO_2H$, —$CO_2R^c$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, —$NR^dSO_2 R^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), hydroxy-($C_1$-$C_4$alkyl)-, halo($C_1$-$C_4$alkoxy)-, $C_1$-$C_4$alkoxy-, hydroxy-($C_2$-$C_4$alkoxy)-, $C_1$-$C_4$alkoxy-($C_1$-$C_4$alkoxy)-, —$COR^d$, —$CON(R^d)(R^f)$, and —$CO_2R^d$;

$R^{14}$ is optionally substituted $C_1$-$C_4$alkyl, wherein said optionally substituted $C_1$-$C_4$alkyl is optionally substituted by a substituent selected from —$OR^c$, —$NR^cR^d$, —$CO_2R^c$, —$CONR^cR^d$, —$SO_2NR^cR^d$, and —$OCONR^cR^d$;

$R^{16}$ is H, halogen, or $C_1$-$C_4$alkyl;

$R^{15}$ and $R^{17}$ are each independently H, cyclopropyl, or $C_1$-$C_4$alkyl;

$R^a$ is H, —$R^c$, —$COR^c$, —$CO_2H$, —$CO_2R^c$, —$SOR^c$, —$SO_2R^c$, —$CONH_2$, —$CONR^cR^d$, —$SO_2NH_2$, or —$SO_2NR^cR^d$;

each $R^b$ is independently $C_1$-$C_4$alkyl, halo($C_1$-$C_4$alkyl), —($C_1$-$C_4$alkyl)-OH, —($C_1$-$C_4$alkyl)-O—($C_1$-$C_4$alkyl), —($C_1$-$C_4$alkyl)-$N(R^e)(R^f)$, —($C_1$-$C_4$alkyl)-O—$CO(C_1$-$C_4$alkyl), or —($C_1$-$C_4$alkyl)-CO—O—($C_1$-$C_4$alkyl);

each $R^c$ is independently $C_1$-$C_4$alkyl, halo($C_1$-$C_4$alkyl), —($C_1$-$C_4$alkyl)-OH, —($C_1$-$C_4$alkyl)-O—($C_1$-$C_4$alkyl), —($C_1$-$C_4$alkyl)-$N(R^e)(R^f)$, —($C_1$-$C_4$alkyl)-O—$CO(C_1$-$C_4$alkyl), —($C_1$-$C_4$alkyl)-CO—O—($C_1$-$C_4$alkyl), optionally substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —C$_1$-C$_4$alkyl-9-10 membered heteroaryl,
wherein the C$_3$-C$_6$cycloalkyl, phenyl, 4-6 membered heterocycloalkyl, 5-6 membered heteroaryl or optionally substituted 9-10 membered heteroaryl moiety of said substituted C$_3$-C$_6$cycloalkyl, optionally substituted phenyl, optionally substituted 4-6 membered heterocycloalkyl, optionally substituted 5-6 membered heteroaryl, optionally substituted 9-10 membered heteroaryl optionally substituted —C$_1$-C$_4$alkyl-C$_3$-C$_6$cycloalkyl, optionally substituted —C$_1$-C$_4$alkyl-phenyl, optionally substituted —C$_1$-C$_4$alkyl-4-6 membered heterocycloalkyl, optionally substituted —C$_1$-C$_4$alkyl-5-6 membered heteroaryl, or optionally substituted —C$_1$-C$_4$alkyl-9-10 membered heteroaryl is optionally substituted by 1-4 substituents each independently selected from halogen, hydroxy, amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_2$-C$_4$alkoxy)-, C$_1$-C$_4$alkoxy-(C$_1$-C$_4$alkoxy)-, —COR$^d$, —CON(R$^d$)(R$^f$), and —CO$_2$R$^d$;
each R$^d$ is independently H or C$_1$-C$_4$alkyl;
each R$^e$ is independently H,
C$_1$-C$_4$alkyl, —CO(C$_1$-C$_4$alkyl), —OCO(C$_1$-C$_4$alkyl), —CO$_2$(C$_1$-C$_4$alkyl), —CO-(optionally substituted 5-6 membered heterocycloalkyl), —CO(C$_1$-C$_4$alkyl)-(optionally substituted 5-6 membered heterocycloalkyl), —CO (optionally substituted 5-6 membered heteroaryl), —CO(C$_1$-C$_4$alkyl)-(optionally substituted 5-6 membered heteroaryl),
wherein the optionally substituted 5-6 membered heterocycloalkyl or optionally substituted 5-6 membered heteroaryl is optionally substituted 1-4 substituents each independently selected from halogen, hydroxy, amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), halo(C$_1$-C$_4$alkoxy)-, C$_1$-C$_4$alkoxy-, hydroxy-(C$_2$-C$_4$alkoxy)-, C$_1$-C$_4$alkoxy-(C$_1$-C$_4$alkoxy)-, —COR$^d$, —CON(R$^d$)(R$^f$), and —CO$_2$R$^d$;
each R$^f$ is independently H or C$_1$-C$_4$alkyl;
R$^g$ and R$^h$ are each independently H or C$_1$-C$_4$alkyl or R$^g$ and R$^h$, taken together with the atom or atoms through which they are connected, form a 5-6 membered ring;
or a pharmaceutically acceptable salt thereof.
In one embodiment, wherein when s of Formula I-N or Formula I is 0, R$^{C1}$ and R$^{C2}$ are each independently H or C$_1$-C$_4$alkyl. In one embodiment, wherein when s of Formula I-N or Formula I is 0, R$^{C1}$ and R$^{C2}$ are each independently ethyl.
In one embodiment, wherein when r of Formula I-N or Formula I is 1, B, taken together with R$^{B1}$ and R$^{B2}$ form —CH$_2$CH=CHCH$_2$—, —CH$_2$CH$_2$CH$_2$CH$_2$—, —CH$_2$CH(OH)CH(OH)CH$_2$—, or —CH$_2$CH$_2$N(CH$_3$)CH$_2$CH$_2$—.
In one embodiment, wherein when r of Formula I-N or Formula I is 1, B, taken together with R$^{B1}$ and R$^{B2}$, form a —CH$_2$CH=CHCH$_2$—.
In one embodiment R$^4$ and R$^6$ a of Formula I-N or Formula I are each H. In one embodiment, R$^{16}$ is H. In one embodiment, R$^{14}$, R$^{15}$, and R$^{17}$ are each independently C$_1$-C$_3$alkyl.
In yet another embodiment, the STING agonist has the structure of Formula (I-N-B')

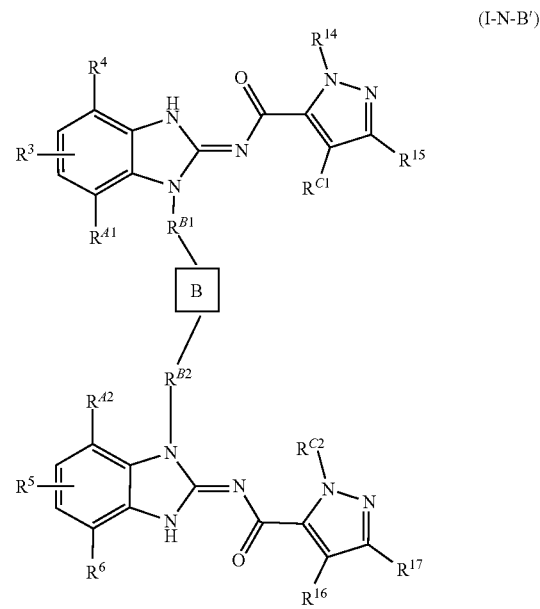

wherein
R$^3$ and R$^5$ are each independently —CON(R$^d$)(R$^f$), or one of R$^3$ and R$^5$ is —CON(R$^d$)(R$^f$), and the other of R$^3$ and R$^5$ is H, COOH or —CO$_2$(R$^e$);
R$^c$ is C$_1$-C$_4$alkyl;
R$^{B1}$ and R$^{B2}$ are each independently —CH$_2$—;
B is -halo(C$_1$-C$_5$alkyl), unsubstituted —C$_1$-C$_5$alkyl, or unsubstituted —C$_2$-C$_5$alkenyl-;
R$^{A2}$ and R$^{A1}$ are each independently H, halogen, hydroxyl, —O—P(O)(OH)$_2$,
—O—P(O)(R$^I$R$^{II}$)$_2$, optionally substituted (C$_1$-C$_6$alkyl), or optionally substituted (C$_1$-C$_6$alkyl)oxy-,
wherein C$_1$-C$_6$alkyl of said optionally substituted (C$_1$-C$_6$alkyl), or optionally substituted (C$_1$-C$_6$alkyl)oxy- is optionally substituted with 1-4 substituents each independently selected from the group consisting of hydroxyl, —O—P(O)(OH)$_2$,
—O—P(O)(R$^I$R$^{II}$)$_2$, C$_1$-C$_4$alkoxyl, —N(R$^e$)(R$^f$), —CO$_2$(R$^f$), optionally substituted phenyl, and optionally substituted 5-6 membered heterocycloalkyl; wherein said optionally substituted phenyl, or 5-6 membered heterocycloalkyl is optionally substituted by 1-4 substituents each independently selected from halogen, hydroxy, —O—P(O)(OH)$_2$, —O—P(O)(R$^I$R$^{II}$)$_2$, amino, (C$_1$-C$_6$alkyl)amino-, (C$_1$-C$_6$alkyl)(C$_1$-C$_6$alkyl)amino-, halo(C$_1$-C$_6$alkyl), hydroxy-(C$_1$-C$_4$alkyl)-,
—(C$_1$-C$_4$alkyl)-O—P(O)(OH)$_2$, —(C$_1$-C$_4$alkyl)-O—P(O)(R$^I$R$^{II}$)$_2$, halo(C$_1$-C$_4$alkoxy)-, C$_1$-C$_4$alkoxy-, hydroxy-(C$_2$-C$_4$alkoxy)-, —(C$_2$-C$_4$alkoxy)-O—P(O)(OH)$_2$,
—(C$_2$-C$_4$alkoxy)-O—P(O)(R$^I$R$^{II}$)$_2$, —(C$_1$-C$_6$alkyl)-NH$_2$, —C$_1$-C$_4$alkyl-(C$_1$-C$_4$alkoxyl) and C$_1$-C$_4$alkoxy-(C$_1$-C$_4$alkoxy)-;
each R$^d$ is independently H or C$_1$-C$_4$alkyl;
R$^e$ is selected from H, (C$_1$-C$_4$alkyl), —CO(C$_1$-C$_4$alkyl), —OCO(C$_1$-C$_4$alkyl), —(C$_1$-C$_4$alkyl)-NH$_2$, —(C$_1$-C$_4$alkyl) C$_1$-C$_4$alkoxy, or —CO$_2$(C$_1$-C$_4$alkyl),
each occurrence of R$^f$ is H or (C$_1$-C$_4$alkyl);
R$^4$ and R$^6$ are H;
R$^{14}$ is C$_1$-C$_4$alkyl;
R$^{C1}$ is H or C$_1$-C$_4$alkyl;

$R^{C2}$ is $C_1$-$C_4$alkyl;
$R^{15}$ is H or $C_1$-$C_4$alkyl;
$R^{16}$ is H or $C_1$-$C_4$alkyl;
$R^{17}$ is H or $C_1$-$C_4$alkyl; and
each occurrence of $R^I$ and $R^{II}$ are independently ($C_1$-$C_6$alkyl)oxy-,
or a pharmaceutically acceptable salt thereof.

In one embodiment, the STING agonist has the structure of Formula (I-N-b'),

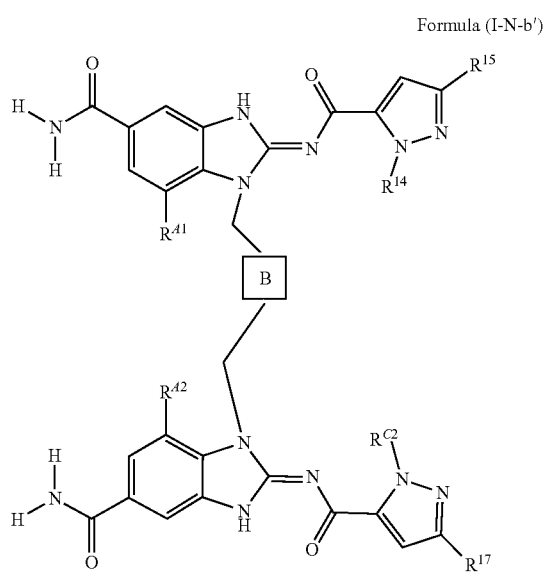

Formula (I-N-b')

wherein
B is -halo($C_1$-$C_5$alkyl), unsubstituted —$C_1$-$C_5$alkyl, or unsubstituted —$C_2$-$C_5$alkenyl-;
$R^{42}$ and $R^{41}$ are each independently H, halogen, hydroxyl, —O—P(O)(OH)$_2$, —O—P(O)($R^IR^{II}$)$_2$, optionally substituted ($C_1$-$C_6$alkyl), or optionally substituted ($C_1$-$C_6$alkyl)oxy-,
wherein $C_1$-$C_6$alkyl of said optionally substituted ($C_1$-$C_6$alkyl), or optionally substituted ($C_1$-$C_6$alkyl)oxy- is optionally substituted with 1-4 substituents each independently selected from the group consisting of hydroxyl, $C_1$-$C_4$alkoxyl,
—N($R^e$)($R^f$), —CO$_2$($R^f$), optionally substituted phenyl, and optionally substituted 5-6 membered heterocycloalkyl, and wherein said optionally substituted phenyl, or 5-6 membered heterocycloalkyl is optionally substituted by 1-4 substituents each independently selected from halogen, hydroxy, —O—P(O)(OH)$_2$,
—O—P(O)($R^IR^{II}$)$_2$, amino, ($C_1$-$C_6$alkyl)amino-, ($C_1$-$C_6$alkyl)($C_1$-$C_6$alkyl)amino-, halo($C_1$-$C_6$alkyl), hydroxy-($C_1$-$C_4$alkyl)-, —($C_1$-$C_4$alkyl)-O—P(O)(OH)$_2$, —($C_1$-$C_4$alkyl)-O—P(O)($R^IR^{II}$)$_2$, halo($C_1$-$C_4$alkoxy)-, $C_1$-$C_4$alkoxy-, hydroxy-($C_2$-$C_4$alkoxy)-, —($C_2$-$C_4$alkoxy)-O—P(O)(OH)$_2$, —($C_2$-$C_4$alkoxy)-O—P(O)($R^IR^{II}$)$_2$, —($C_1$-$C_6$alkyl)-NH$_2$,
—$C_1$-$C_4$alkyl-($C_1$-$C_4$alkoxyl) and $C_1$-$C_4$alkoxy-($C_1$-$C_4$alkoxy)-;
$R^e$ is selected from H, ($C_1$-$C_4$alkyl), —CO($C_1$-$C_4$alkyl), —OCO($C_1$-$C_4$alkyl),
—($C_1$-$C_4$alkyl)-NH$_2$, —($C_1$-$C_4$alkyl) $C_1$-$C_4$alkoxy, or —CO$_2$($C_1$-$C_4$alkyl),
each $R^f$ is H or ($C_1$-$C_4$alkyl);

$R^{14}$ is $C_1$-$C_4$alkyl;
$R^{C2}$ is $C_1$-$C_4$alkyl;
$R^{15}$ is $C_1$-$C_4$alkyl; and
$R^{17}$ is $C_1$-$C_4$alkyl;
each occurrence of $R^I$ and $R^{II}$ are independently ($C_1$-$C_6$alkyl)oxy-;
or a pharmaceutically acceptable salt thereof.

In one embodiment, wherein $R^{42}$ and $R^{41}$ of Formula I-N-b' are each independently H, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from the group consisting of hydroxyl, —N($R^e$)($R^f$), $C_1$-$C_4$alkoxyl, phenyl, optionally substituted 5-6 membered heterocycloalkyl containing at least one nitrogen or oxygen as a member of the ring, and $R^e$ and Rare each independently H or $C_1$-$C_4$alkyl.

In one embodiment, at least one of $R^{42}$ or $R^{41}$ is each independently H, optionally substituted ($C_1$-$C_6$alkyl), or optionally substituted ($C_1$-$C_6$alkyl)oxy-, and the $C_1$-$C_6$alkyl of said optionally substituted ($C_1$-$C_6$alkyl), optionally substituted ($C_1$-$C_6$alkyl)oxy- is optionally substituted with 1-4 substituents each independently selected from the group consisting of —N($R^e$)($R^f$), tetrahydropyran, pyrrolidinyl, piperazinyl, piperidyl and morpholinyl, and $R^e$ and Rare each independently H or $C_1$-$C_4$alkyl.

In one embodiment, the compound of Formula X

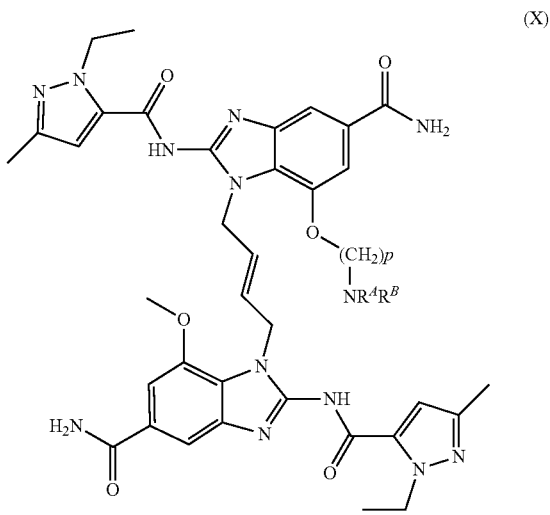

(X)

wherein
P is an integer among 1 to 6,
$R^A$ and $R^B$ are independently H, ($C_1$-$C_4$alkyl)
or N, $R^A$ and $R^B$ form an optionally substituted 5 or 6 membered heterocyclic ring,
wherein the heterocyclic ring is selected from the group consisting of morpholinyl, piperidinyl, piperazinyl and pyrrolidinyl, and
the heterocyclic ring is optionally substituted by one or two substituents independently selected from the group consisting of hydroxyl and $C_1$-$C_3$ alkyl optionally substituted with one or two substituents of hydroxyl or $C_1$-$C_3$ alkoxyl;
or a pharmaceutically acceptable salt thereof.

In one aspect, the STING agonist of Formula (I-N), (I) or (X) are not:

(E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-hydroxypropoxy)-1H-benzo[d]imidazole-5-carboxamide;

(E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-hydroxypropoxy)-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-hydroxypropoxy)-2,3-dihydro-1H-benzo[d]imidazole-5-carboxamide;

or a salt thereof, particularly a pharmaceutically acceptable salt, thereof.

In one aspect, the STING agonist of Formula (I-N), (I) or (X) are not:

(E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide;

(E)-1-((E)-4-((E)-5-carbamoyl-2-((1-ethyl-3-methyl-1H-pyrazole-5-carbonyl)imino)-7-(3-hydroxypropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-7-(3-hydroxypropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

or a salt thereof, particularly a pharmaceutically acceptable salt, thereof.

In one aspect, the STING agonist of Formula (I-N), (I) or (X) are not:

(E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide;

(E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide;

or a salt thereof, particularly a pharmaceutically acceptable salt, thereof.

In one aspect, the STING agonist of Formula (I-N), (I) or (X) are not:

(E)-1-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide;

(E)-1-((E)-4-((E)-5-carbamoyl-2-((1-ethyl-3-methyl-1H-pyrazole-5-carbonyl)imino)-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

or a salt thereof, particularly a pharmaceutically acceptable salt, thereof.

In one aspect, the STING agonist of Formula (I-N), (I) or (X) are not:

3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyldihydrogen phosphate;

(E)-3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl dihydrogen phosphate;

3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy) propyl dihydrogen phosphate;

or a salt thereof, particularly a pharmaceutically acceptable salt, thereof.

In one aspect, the STING agonist of Formula (I-N), (I) or (X) are not:

(E)-4-((5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)oxy) butanoic acid;

(E)-7-(aminomethyl)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide; and (E)-3-(5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl) propanoic acid or a salt thereof, particularly a pharmaceutically acceptable salt, thereof.

In one embodiment of the present methods the STING agonist is:

(E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-hydroxypropoxy)-1H-benzo[d]imidazole-5-carboxamide;

(E)-1-((E)-4-((E)-5-carbamoyl-2-((1-ethyl-3-methyl-1H-pyrazole-5-carbonyl)imino)-2,3-dihydro-1H-benzol[d]imidazol-1-yl)but-2-en-1-yl)-2-((1-ethyl-3-methyl-1H-pyrazole-5-carbonyl)imino)-7-(3-hydroxypropoxy)-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-2,3-dihydro-1H-benzol[d]imidazol-1-yl)but-2-en-1-yl)-2-((1-ethyl-3-methyl-1H-pyrazole-5-carbonyl)imino)-7-(3-hydroxypropoxy)-2,3-dihydro-1H-benzo[d]imidazole-5-carboxamide;

(E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide;

(E)-1-((E)-4-((E)-5-carbamoyl-2-((1-ethyl-3-methyl-1H-pyrazole-5-carbonyl)imino)-7-(3-hydroxypropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-7-(3-hydroxypropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

(E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide;

(E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide;

(E)-1-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide;

(E)-1-((E)-4-((E)-5-carbamoyl-2-((1-ethyl-3-methyl-1H-pyrazole-5-carbonyl)imino)-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

(Z)-1-((E)-4-((Z)-5-carbamoyl-2-((1-ethyl-3-methyl-1H-pyrazole-5-carbonyl)imino)-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide;

3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyldihydrogen phosphate;

(E)-3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl dihydrogen phosphate;

3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyl dihydrogen phosphate;

(E)-1-(4-(5-Carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide tris hydrochloride;

(E)-4-((5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)oxy) butanoic acid;

(E)-7-(aminomethyl)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide;

(E)-3-(5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl) propanoic acid;

(E)-1-(4-(5-carbamoyl-2-(1-ethyl-3-methyl-1H-pyrazole-5-carboxamido)-7-(3-(piperazin-1-yl)propoxy)-1H-benzo[d]imidazol-1-yl)but-2-en-1-yl)-2-(1-ethyl-3-methyl-1Hpyrazole-5-carboxamido)-7-methoxy-1H-benzo[d]imidazole-5-carboxamide;

(E)-1-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-7-ethoxy-2-(1-ethyl-3-methyl-1H-pyrazole-5-carboxamido)-1H-benzo[d]imidazole-5-carboxamide; and (E)-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-(3-(dimethylamino)propoxy)-2-(1-ethyl-3-methyl-1H-pyrazole-5-carboxamido)-1H-benzo[d]imidazole-5-carboxamide;

or a pharmaceutically acceptable salt thereof.

The STING agonist of the present invention can be systemically administered to said human via an administration route selected from intravenous, subcutaneous, oral, intramuscular, and transdermal.

In one embodiment of the present invention methods are provided of administering a STING agonist to a human in need thereof comprising systemically administering said STING agonist. In certain aspects, the STING agonist increases cytokine levels in the blood of said human to a concentration effective to stimulate Tcells in said human. In certain aspects, the STING agonist does not increase cytokine levels in the blood of said human to a concentration high enough to cause adverse immune reactions. In one embodiment, the adverse immune reaction is dose limiting toxicity. In one embodiment, the human has at least one disease selected from: inflammation, allergic and autoimmune diseases, infectious diseases, hepatitis C virus (HCV), hepatitis B virus (HBV), influenza, skin warts, multiple sclerosis, human immunodeficiency virus (HIV) infection, AIDS, cancer (including basal cell carcinoma, and squamous cell carcinoma), pre-cancerous syndromes (including actinic keratoses).

In one embodiment, the STING agonist is administered as vaccine adjuvant.

Also provided herein are the use of a STING agonist for systemically administration to a human in need thereof wherein the STING agonist increases certain cytokines in disease tissue to a greater concentration than said cytokines in blood and/or plasma and/or serum of said human. Also, provided are compositions comprising at least one STING agonist for use in the treatment of inflammation, allergic and autoimmune diseases, infectious diseases, hepatitis C virus (HCV), hepatitis B virus (HBV), influenza, skin warts, multiple sclerosis, human immunodeficiency virus (HIV) infection, AIDS, cancer, pre-cancerous syndromes in a human characterized in that the composition is systemically administered to said human and further wherein said STING agonist increases the concentration of at least one cytokine in disease tissue at least three times more than the concentration of at least one cytokine in blood and/or serum and/or plasma. In one embodiment, the human has cancer. In one embodiment, the disease tissue is a tumor microenvironment. In one embodiment use of a STING agonist or a pharmaceutical composition comprising said STING agonist is provided for the treatment of cancer via systemic administration. In one aspect, the STING agonist increase the concentration of at least one cytokine in the tumor microenvironment or disease tissue to at least three time higher than the blood and/or serum and/or plasma when systemically administered to a human. In one embodiment, the present invention provides the use of a STING agonist in the manufacture of a medicament for systemic administration to a human wherein the medicament increases the concentration of at least one cytokine in disease tissue compared with the concentration of at least one cytokine in blood and/or serum and/or plasma.

Suitably, the invention relates to a method of treating cancer in a human that comprises systemically administering an effective amount of a STING agonist to said human, wherein the STING agonist induces a higher concentration of at least one cytokine in a tumor microenvironment of said human compared with the concentration of said cytokine in the blood, serum, and/or plasma of said human. Suitably, the cytokine is selected from IL-6, TNFα, IFNβ, and IFNγ. Suitably, the target index (TI) is 3 or greater for the selected cytokine. Suitably, the target index (TI) is 10 or greater for the selected cytokine.

Suitably, the invention relates to a method of treating cancer in a human that comprises systemically administering an effective amount of a STING agonist to said human, wherein the STING agonist induces a higher concentration of at least one cytokine in a tumor microenvironment of said human compared with the concentration of said cytokine in the blood, serum, or plasma of said human. Suitably, the cytokine is selected from IL-6, TNFα, IFNβ, and IFNγ. Suitably, the target index (TI) is 3 or greater for the selected cytokine. Suitably, the target index (TI) is 10 or greater for the selected cytokine.

Suitably, the invention relates to a method of treating cancer in a human that comprises systemically administering an effective amount of a STING agonist to said human, wherein the STING agonist induces a has a significantly higher Cmax concentration in the tumor microenvironement of said human compared with blood, serum and/or plasma of said human.

Suitably, the invention relates to a method of treating cancer in a human that comprises systemically administering an effective amount of a STING agonist to said human, wherein the STING agonist induces a has a significantly higher Cmax concentration in the tumor microenvironement of said human compared with blood, serum or plasma of said human.

As used herein the term "agonist" refers to any compound, for example a STING agonist, which upon contact with STING causes one or more of the following (1) stimulates or activates the STING protein, (2) enhances, increases or promotes, induces or prolongs an activity, function or presence of STING and/or (3) enhances, increases, promotes or induces the expression of the STING. Agonist activity can be measured in vitro by various assays know in the art such as, but not limited to, measurement of cell signaling, cell proliferation, immune cell activation markers, cytokine production. Agonist activity can also be measured in vivo by various assays that measure surrogate end points such as, but not limited to the measurement of T cell proliferation or cytokine production, in particular type I interferon.

By the term "treating" or "treatment" and grammatical variations thereof as used herein, is intended to mean at least the mitigation of a disease or disorder in a human. In reference to a particular condition, treating means: (1) to ameliorate the condition of one or more of the biological manifestations of the condition, (2) to interfere with (a) one or more points in the biological cascade that leads to or is responsible for the condition or (b) one or more of the biological manifestations of the condition, (3) to alleviate one or more of the symptoms, effects or side effects associated with the condition or treatment thereof, (4) to slow the progression of the condition or one or more of the biological manifestations of the condition and/or (5) to cure said condition or one or more of the biological manifestations of the condition by eliminating or reducing to undetectable levels one or more of the biological manifestations of the condition for a period of time considered to be a state of remission for that manifestation without additional treatment over the period of remission. One skilled in the art will understand the duration of time considered to be remission for a particular disease or condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof. Thus, "Prevent", "preventing" or "prevention" refers to the prophylactic administration of a drug to diminish the likelihood of the onset of or to delay the onset of a disease or biological manifestation thereof. Prophylactic therapy is appropriate, for example, when a subject is considered at high risk for developing cancer, such as when a subject has a strong family history of cancer or when a subject has been exposed to a carcinogen. The methods of treatment for mitigation of a disease or disorder include the use of the compounds in this invention in any conventionally acceptable manner, for example for retardation, therapy or cure of a STING-mediated disease or disorder, as described hereinabove. Thus, in one embodiment, "treat" "treating" or "treatment" in reference to cancer refers to alleviating the cancer, eliminating or reducing one or more symptoms of the cancer, slowing or eliminating the progression of the cancer, reducing the tumor volume of at least one tumor, and delaying the reoccurrence of the condition in a previously afflicted or diagnosed patient or subject.

As used herein, the terms "cancer," "neoplasm," and "tumor" are used interchangeably and, in either the singular or plural form, refer to cells that have undergone a malignant transformation that makes them pathological to the host organism. Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a patient.

As used herein the term "solid tumor" refers to an abnormal mass of tissue that usually does not contain cysts or liquid areas. Solid tumors may be benign or malignant. Different types of solid tumors are named for the type of cells that form them. Examples of solid tumors include but are not limited to, sarcomas, carcinomas, and lymphomas. Examples of solid tumor cancers include, but are not limited to, colon, breast, gastric, ovarian, lung, cervical, melanoma, renal, prostate, lymphoma, neuroblastoma, pancreatic and bladder cancers.

Suitably, the methods of the invention are used in the treatment of solid tumors.

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelieal carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be amenable to therapy by a method disclosed herein include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Other cancers that can be amenable to treatment according to the methods disclosed herein include atypical meningioma (brain), islet cell carcinoma (pancreas), medullary carcinoma (thyroid), mesenchymoma (intestine), hepatocellular carcinoma (liver), hepatoblastoma (liver), clear cell carcinoma (kidney), and neurofibroma mediastinum.

Further exemplary cancers that can be amenable to treatment using a method disclosed herein include, but are not limited to, cancers of neuroectodermal and epithelial origin. Examples of cancers of neuroectodermal origin include, but are not limited to, Ewings sarcoma, spinal tumors, brain tumors, supratenbrial primative neuroectodermal tumors of yancy, tubulocystic carcinoma, mucinous tubular and spindle cell carcinoma, renal tumors, mediastinum tumors, neurogliomas, neuroblastomas, and sarcomas in adolescents and young adults. Examples of epithelial origin include, but are not limited to, small cell lung cancer, cancers of the breast, eye lens, colon, pancreas, kidney, liver, ovary, and bronchial epithelium.

Tumors may be a hematopoietic (or hematologic or hematological or blood-related) cancer, for example, cancers derived from blood cells or immune cells, which may be referred to as "liquid tumors." Specific examples of clinical conditions based on hematologic tumors include leukemias such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

The cancer may be any cancer in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblastic) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocytic (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polcythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT); as well as myelofibrosis (MFS) with or without agnogenic myeloid metaplasia.

Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent Bcell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphomas (T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL), Waldenstrom's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

Suitably, the methods of the invention are directed to treating cancer. Suitably, the methods of the invention are directed to treating a cancer selected from: non-small cell lung cancer (NSCLC), microsatellite stable (MSS) colorectal cancer, gastroesophageal adenocarcinoma (GEC), and squamous cell carcinoma of the head and neck (SCCHN).

Suitably the cancer is selected from: cancers of the lung, bone, pancreas, skin, head, neck, uterus, ovaries, stomach, colon, breast, esophagus, small intestine, bowel, endocrine system, thyroid glad, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemagioma; hepatoma; fibrosarcoma; chondrosarcoma; myeloma; chronic or acute leukemia; lymphocytic lymphomas; primary CNS lymphoma; neoplasms of the CNS; spinal axis tumours; squamous cell carcinomas; synovial sarcoma; malignant pleural mesotheliomas; brain stem glioma; pituitary adenoma; bronchial adenoma; chondromatous hanlartoma; inesothelioma; and Hodgkin's Disease or a combination of one or more of the foregoing cancers.

Suitably the cancer is selected from: brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

Suitably, the methods of the invention are directed to treating pre-cancerous syndromes.

Suitably the pre-cancerous syndrome is selected from: cervical intraepithelial neoplasia, monoclonal gammapathy of unknown significance (MGUS), myelodysplastic syndrome, aplastic anemia, cervical lesions, skin nevi (pre-melanoma), prostatic intraepithleial (intraductal) neoplasia (PIN), Ductal Carcinoma in situ (DCIS), colon polyps and severe hepatitis or cirrhosis.

As used herein "tumor antigens" are proteins that are produced by tumor cells that elicit an immune response, particularly T-cell mediated immune responses. The term "tumor antigen" as used herein includes both tumor-specific antigens and tumor-associated antigens. Tumor-specific antigens are unique to tumor cells and do not occur on other cells in the body. Tumor-associated antigens are not unique to a tumor cell and instead is also expressed on a normal cell under conditions that fail to induce a state of immunologic tolerance to the antigen. The expression of the antigen on the tumor may occur under conditions that enable the immune system to respond to the antigen. Tumor-associated antigens may be antigens that are expressed on normal cells during fetal development when the immune system is immature and unable to respond or they may be antigens that are normally present at extremely low levels on normal cells but which are expressed at much higher levels on tumor cells.

Non-limiting examples of tumor antigens include the following: differentiation antigens such as MART-1/MelanA (MART-I), gp100 (Pmel 17), tyrosinase, TRP-1, TRP-2 and tumor-specific multilineage antigens such, MAGE family antigens including but not limited to MAGE1, MAGE3, MAGE10, MAGE11, MAGE12, MAGEA2, MAGEA3, MAGEA4, MAGEA6, MAGEA8, MAGEA9, MAGEB18, MAGEB6, MABEC1, MAGED2, MAGEE1, MAGEH1, MAGEL2, BAGE, GAGE-1, GAGE-2, p15; MEL4, melanoma associated antigen 100+, melanoma gp100, NRIP3, NYS48, OCIAD1, OFA-iLRP, OIP5, ovarian carcinoma-associated antigen (OV632), PAGE4, PARP9, PATE, plastin L, PRAME, prostate-specific antigen, proteinase 3, prostein, Reg3a, RHAMM, ROPN1, SART2, SDCCAG8, SEL1L, SEPT1, SLC45A2, SPANX, SSX5, STXGALNAC1, STEAP4, survivin, TBC1D2, TEM1, TRP1, tumor antigens of epithelial origin, XAGE1, XAGE2, WT-1; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein 30 Barr virus antigens EBVA and the human papillomavirus (HPV) antigens E6 and E7.

Other tumor antigens include, but are not limited to, TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, TPS, glioma-associated antigen, β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), ELF2M, neutrophil elastase, ephrinB2, CD19, CD20, CD22, ROR1, CD33/IL3Ra, c-Met, PSMA, Glycolipid F77, EGFRvIII, GD-2, insulin growth factor (IGF)-I, IGF-II, IGF-I receptor and mesothelin.

It will be appreciated by those skilled in the art that the compounds of this invention may exist in other tautomeric forms including zwitterionic forms, or isomeric forms. All tautomeric (including zwitterionic forms) and isomeric forms of the formulas and compounds described herein are intended to be encompassed within the scope of the present invention.

It will also be appreciated by those skilled in the art that the compounds of this invention may exist in tautomeric forms including, but not limited to, Formula (A), Formula (B) and/or Formula (C) or zwitterionic forms including, but not limited to, Formula (D) or Formula (E).

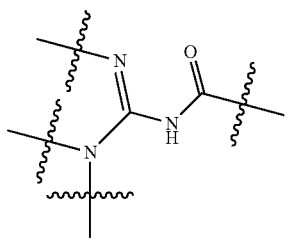

Formula (A)

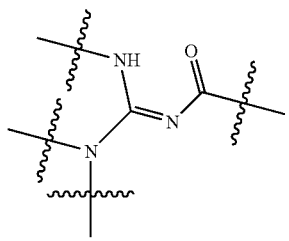

Formula (B)

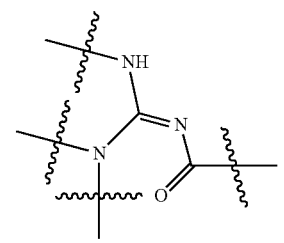

Formula (C)

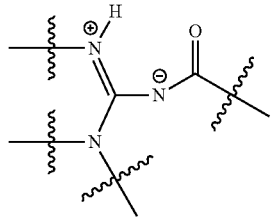

Formula (D)

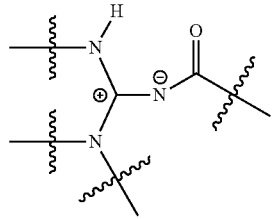

Formula (E)

The chemical names provided for the intermediate compounds and/or the compounds of this invention described herein may refer to any one of the tautomeric representations of such compounds (in some instances, such alternate names are provided with the experimental). It is to be understood that any reference to a named compound (an intermediate compound or a compound of the invention) or a structurally depicted compound (an intermediate compound or a compound of the invention) is intended to encompass all tautomeric forms including zwitterionic forms of such compounds and any mixture thereof.

As used herein, the term "alkyl" represents a saturated, straight or branched hydrocarbon group having the specified number of carbon atoms. The term "$C_1$-$C_4$alkyl" refers to a straight or branched alkyl moiety containing from 1 to 4 carbon atoms. Exemplary alkyls include, but are not limited to methyl, ethyl, n-propyl, isopropyl, n-butyl, isobutyl, s-butyl, t-butyl, pentyl and hexyl.

When a substituent term such as "alkyl" is used in combination with another substituent term, for example as in "hydroxy($C_1$-$C_4$alkyl)", the linking substituent term (e.g., alkyl) is intended to encompass a divalent moiety, wherein the point of attachment is through that linking substituent. Examples of "hydroxy($C_1$-$C_4$alkyl)" groups include, but are not limited to, hydroxymethyl, hydroxyethyl, and hydroxyisopropyl.

As used herein, the term "halo(alkyl)" represents a saturated, straight or branched hydrocarbon group having the specified number (n) of carbon atoms and one or more (up to 2n+1) halogen atoms. For example, the term "halo($C_1$-$C_4$alkyl)" represents a group having one or more halogen atoms, which may be the same or different, at one or more carbon atoms of an alkyl moiety containing from 1 to 4 carbon atoms. Examples of "halo($C_1$-$C_4$alkyl)" groups include, but are not limited to, —$CF_3$ (trifluoromethyl), —$CCl_3$ (trichloromethyl), 1,1-difluoroethyl, 2,2,2-trifluoroethyl, and hexafluoroisopropyl.

"Alkenyl" refers to straight or branched hydrocarbon group having the specified number of carbon atoms and at least 1 and up to 3 carbon-carbon double bonds. Examples include ethenyl and propenyl.

"Alkynyl" refers to straight or branched hydrocarbon group having the specified number of carbon atoms and at least 1 and up to 3 carbon-carbon triple bonds. Examples include ethynyl and propynyl.

"Alkoxy-" or "(alkyl)oxy-" refers to an "alkyl-oxy-" group, containing an alkyl moiety, having the specified number of carbon atoms, attached through an oxygen linking atom. For example, the term "$C_1$-$C_4$alkoxy-" represents a saturated, straight or branched hydrocarbon moiety having at least 1 and up to 4 carbon atoms attached through an oxygen linking atom. Exemplary "$C_1$-$C_4$alkoxy-" or "($C_1$-$C_4$alkyl)oxy-" groups include, but are not limited to, methoxy, ethoxy, n-propoxy, isopropoxy, n-butoxy, s-butoxy, and t-butoxy.

As used herein, the term "halo(alkoxy)-" represents a saturated, straight or branched hydrocarbon group having the specified number (n) of carbon atoms and one or more (up to 2n+1) halogen atoms, attached through an oxygen linking atom. For example, the term "halo($C_1$-$C_4$alkoxy)-" refers to a "haloalkyl-oxy-" group, containing a "halo($C_1$-$C_4$alkyl)" moiety attached through an oxygen linking atom. Exemplary "halo($C_1$-$C_4$alkoxy)-" groups include, but are not limited to, —$OCHF_2$ (difluoromethoxy), —$OCF_3$ (trifluoromethoxy), —$OCH_2CF_3$ (trifluoroethoxy), and —$OCH(CF_3)_2$ (hexafluoroisopropoxy).

A carbocyclic group or moiety is a cyclic group or moiety in which the ring members are carbon atoms, which may be saturated, partially unsaturated (non-aromatic) or fully unsaturated (aromatic).

"Cycloalkyl" refers to a non-aromatic, saturated, hydrocarbon ring group containing the specified number of carbon atoms in the ring. For example, the term "$C_3$-$C_6$cycloalkyl" refers to a cyclic group having from three to six ring carbon atoms. Exemplary "$C_3$-$C_6$cycloalkyl" groups include cyclopropyl, cyclobutyl, cyclopentyl, and cyclohexyl.

A heterocyclic group or moiety is a cyclic group or moiety having, as ring members, atoms of at least two different elements, which cyclic group or moiety may be saturated, partially unsaturated (non-aromatic) or fully unsaturated (aromatic).

"Heteroatom" refers to a nitrogen, sulfur, or oxygen atom, for example a nitrogen atom or an oxygen atom.

"Heterocycloalkyl" refers to a non-aromatic, monocyclic or bicyclic group containing 3-10 ring atoms and containing one or more (generally one or two) heteroatom ring members independently selected from oxygen, sulfur, and nitrogen. The point of attachment of a heterocycloalkyl group may be by any suitable carbon or nitrogen atom.

Examples of "heterocycloalkyl" groups include, but are not limited to, aziridinyl, thiiranyl, oxiranyl, azetidinyl, oxetanyl, thietanyl, pyrrolidinyl, tetrahydrofuranyl, tetrahydrothienyl, 1,3-dioxolanyl, piperidinyl, piperazinyl, tetrahydropyranyl, dihydropyranyl, tetrahydrothiopyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, 1,4-dithianyl, morpholinyl, thiomorpholinyl, and hexahydro-1H-1,4-diazepinyl.

Examples of "4-membered heterocycloalkyl" groups include oxetanyl, thietanyl and azetidinyl.

The term "5-6 membered heterocycloalkyl" represents a saturated, monocyclic group, containing 5 or 6 ring atoms, which includes one or two heteroatoms selected independently from oxygen, sulfur, and nitrogen. Illustrative examples of 5-6 membered heterocycloalkyl groups include, but are not limited to pyrrolidinyl, tetrahydrofuranyl, tetrahydrothienyl, tetrahydropyranyl, tetrahydrothiopyranyl, piperidinyl, piperazinyl, morpholinyl, and thiomorpholinyl.

"Heteroaryl" refers to an aromatic monocyclic or bicyclic group containing 5 to 10 ring atoms, including 1 to 4 heteroatoms independently selected from nitrogen, oxygen and sulfur, wherein at least a portion of the group is aromatic. For example, this term encompasses bicyclic heterocyclic-aryl groups containing either a phenyl ring fused to a heterocyclic moiety or a heteroaryl ring moiety fused to a carbocyclic moiety. The point of attachment of a heteroaryl group may be by any suitable carbon or nitrogen atom.

The term "5-6 membered heteroaryl" represents an aromatic monocyclic group containing 5 or 6 ring atoms, including at least one carbon atom and 1 to 4 heteroatoms independently selected from nitrogen, oxygen and sulfur. Selected 5-membered heteroaryl groups contain one nitrogen, oxygen, or sulfur ring heteroatom, and optionally contain 1, 2, or 3 additional nitrogen ring atoms. Selected 6-membered heteroaryl groups contain 1, 2, or 3 nitrogen ring heteroatoms. Examples of 5-membered heteroaryl groups include furyl (furanyl), thienyl, pyrrolyl, imidazolyl, pyrazolyl, triazolyl, tetrazolyl, thiazolyl, isothiazolyl, thiadiazolyl, oxazolyl, isoxazolyl, and oxadiazolyl. Selected 6-membered heteroaryl groups include pyridinyl (pyridyl), pyrazinyl, pyrimidinyl, pyridazinyl and triazinyl.

The term "9-10 membered heteroaryl" refers to an aromatic bicyclic group containing 9 or 10 ring atoms, including 1 to 4 heteroatoms independently selected from nitrogen, oxygen and sulfur. Examples of 9-membered heteroaryl (6,5-fused heteroaryl) 30 groups include benzothienyl, benzofuranyl, indolyl, indolinyl (dihydroindolyl), isoindolyl, isoindolinyl, indazolyl, isobenzofuryl, 2,3-dihydrobenzofuryl, benzoxazolyl, benzoisoxazolyl, benzothiazolyl, benzoisothiazolyl, benzimidazolyl, benzoxadiazolyl, benzothiadiazolyl, benzotriazolyl, purinyl, imidazopyridinyl, pyrazolopyridinyl, triazolopyridinyl and 1,3-benzodioxolyl.

Examples of 10-membered heteroaryl (6,6-fused heteroaryl) groups include quinolinyl (quinolyl), isoquinolyl, phthalazinyl, naphthridinyl (1,5-naphthyridinyl, 1,6-naphthyridinyl, 1,7-naphthyridinyl, 1,8-naphthyridinyl), quinazolinyl, quinoxalinyl, 4H-quinolizinyl, 1,2,3,4-tetrahydroquinolinyl (tetrahydroquinolinyl), 1,2,3,4-tetrahydroisoquinolinyl (tetrahydroisoquinolinyl), cinnolinyl, pteridinyl, and 2,3-dihydrobenzo[b][1,4]dioxinyl.

The terms "halogen" and "halo" refers to a halogen radical, for example, a fluoro, chloro, bromo, or iodo substituent.

"Oxo" represents a double-bonded oxygen moiety; for example, if attached directly to a carbon atom forms a carbonyl moiety (C═O).

"Hydroxy" or "hydroxyl" is intended to mean the radical —OH.

As used herein, the term "cyano" refers to a nitrile group, —C≡N.

As used herein, the term "optionally substituted" indicates that a group (such as an alkyl, cycloalkyl, alkoxy, heterocycloalkyl, aryl, or heteroaryl group) or ring or moiety may be unsubstituted, or the group, ring or moiety may be substituted with one or more substituent(s) as defined in the substituent definitions (A, $R^3$, etc,) provided herein. In the case where groups may be selected from a number of alternative groups, the selected groups may be the same or different.

The term "independently" means that where more than one substituent is selected from a number of possible substituents, those substituents may be the same or different.

The term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the terms "compound(s) of the invention" or "compound(s) of this invention" mean a compound of Formula (I-N) or Formula (I), as defined herein, in any form, i.e., any tautomeric form, any isomeric form, any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

Accordingly, included within the present invention are the compounds of Formula (I-N), or (I), as defined herein, in any salt or non-salt form and any physical form thereof, and mixtures of various forms. While such are included within the present invention, it will be understood that the compounds of Formula (I-N) or (I), as defined herein, in any salt or non-salt form, and in any physical form thereof, may have varying levels of activity, different bioavailabilities and different handling properties for formulation purposes.

A therapeutically "effective amount" is intended to mean that amount of a compound that, when administered to a patient in need of such treatment, is sufficient to effective treat or prevent, as defined herein. Thus, e.g., a therapeutically effective amount of a compound of Formula (I-N), or (I), or a pharmaceutically acceptable salt thereof, is a quantity of an inventive agent that, when administered to a human in need thereof, is sufficient to modulate the activity of STING such that a disease condition which is mediated by that activity is reduced, alleviated or prevented. The amount of a given compound that will correspond to such an amount will vary depending upon factors such as the particular compound (e.g., the potency ($pIC_{50}$), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmacokinetic properties), disease or disorder and its severity and the specific composition and method being used, but can nevertheless be determined by one of skill in the art.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin. Compounds of the present invention and well as methods of making and using such compounds are disclosed and described in PCT/IB2017/051945 (filed Apr. 5, 2017) which is incorporated herein in its entirety.

The invention also provides a pharmaceutical composition comprising from 0.5 to 1,000 mg of a compound selected from anyone of Formulas: (I-N), (I), (I-N-B), (I-N-B') and (X), or pharmaceutically acceptable salt thereof and from 0.5 to 1,000 mg of a pharmaceutically acceptable excipient.

EXAMPLES

The following examples illustrate various non-limiting aspects of this invention.

Intermediate 1

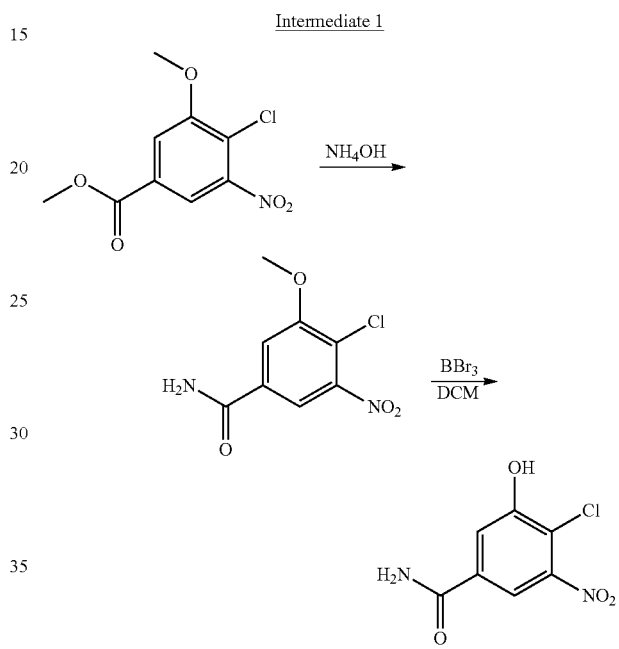

Step 1: 4-chloro-3-methoxy-5-nitrobenzamide

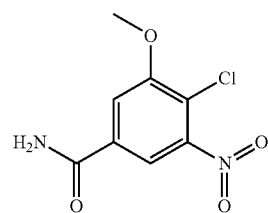

Methyl 4-chloro-3-methoxy-5-nitrobenzoate (1000 mg, 4.07 mmol) was stirred in $NH_4OH$ (10 mL, 77 mmol) at RT for 24 h. The reaction temperature was then increased to 50° C. for 2 h. An additional 2 mL (3.7 eq) of $NH_4OH$ was added to the vessel. After an additional 2 h stirring at 50° C. (4 h total) the reaction was cooled to RT. The solid was filtered and rinsed with cold water. The solid was dried under house vacuum and lyophilized to give 4-chloro-3-methoxy-5-nitrobenzamide (710 mg, 2.99 mmol, 73% yield) as a tan solid. $^1$H NMR (400 MHz, DMSO-$d_6$) δ ppm 8.31 (br. s., 1H), 8.06 (d, J=1.77 Hz, 1H), 7.88 (d, J=1.77 Hz, 1H), 7.81 (br. s., 1H), 4.02 (s, 3H). LCMS (LCMS Method D): Rt=0.71 min, $[M+H]^+$=230.9.

Step 2: 4-chloro-3-hydroxy-5-nitrobenzamide

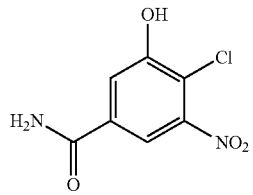 [SMILES: NC(=O)c1cc(O)c(Cl)c([N+](=O)[O-])c1]

4-chloro-3-methoxy-5-nitrobenzamide (1 g, 4.34 mmol) was suspended in dry DCM (15 mL) and stirred at rt. To the reaction was added BBr$_3$ (17.4 mL, 1M in DCM) dropwise. A slurry rapidly formed which was stirred overnight at rt under nitrogen. The reaction was poured into ice water (300 mL) and stirred vigorously for 30 min. The resulting suspension was filtered and the solids dried to afford the title compound (610 mg, 2.82 mmol, 65% yield). $^1$H NMR (400 MHz, DMSO-d$_6$) δ ppm 11.53 (br. s., 1H), 8.17 (br. s., 1H), 7.92 (s, 1H), 7.72 (s, 1H), 7.66 (br. s., 1H). LC-MS (LCMS Method D) Rt=0.60 min, [M+H]$^+$=217.

Intermediate 2

4-(5-(5-Carboxy-3-methyl-1H-pyrazol-1-yl)pentyl)-1-ethyl-3-methyl-1H-pyrazole-5-carboxylic acid

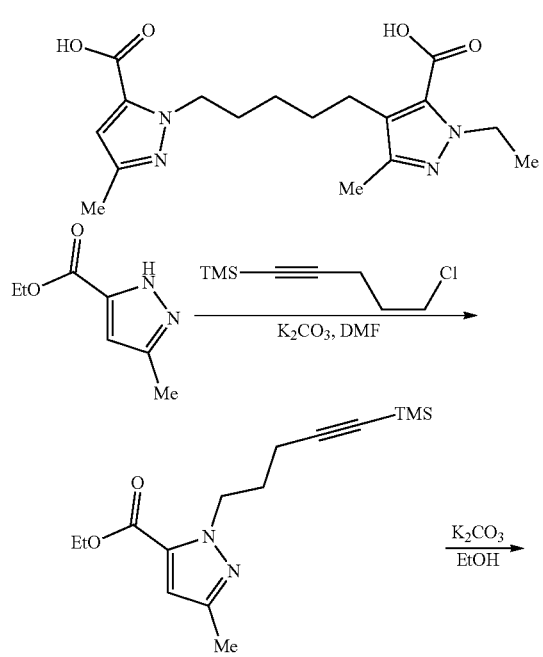

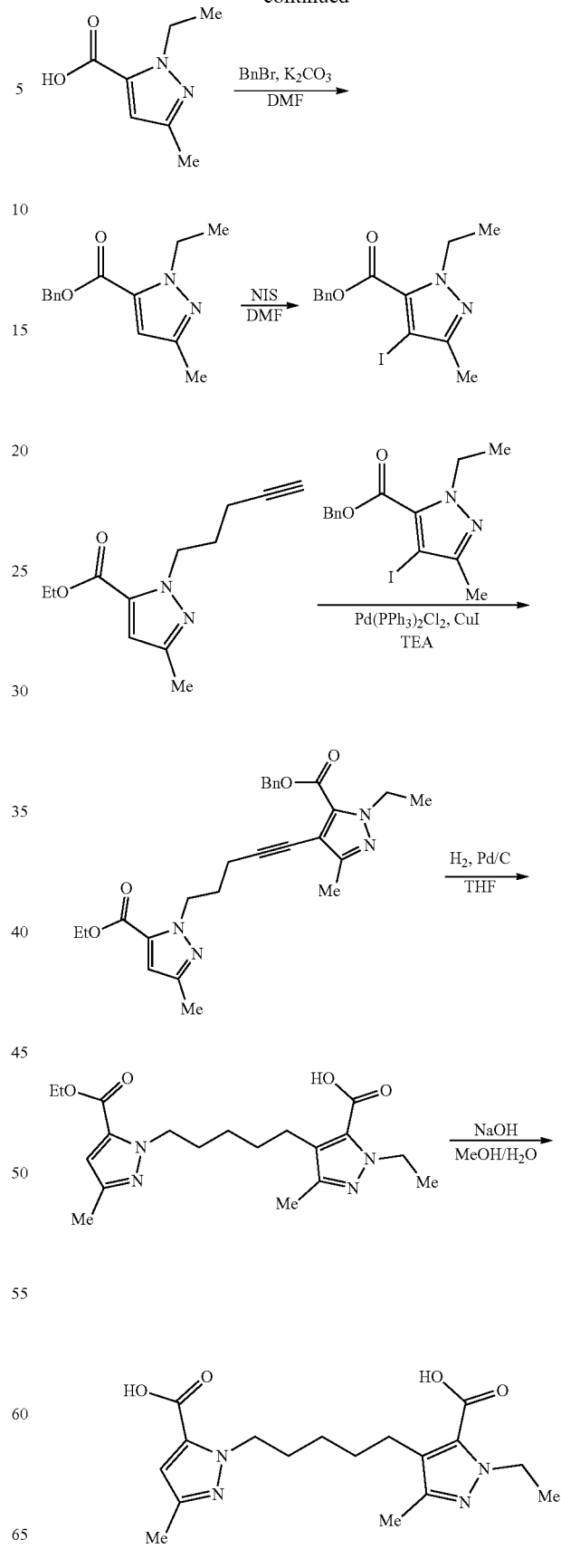

Step 1

Ethyl 3-methyl-1-(5-(trimethylsilyl)pent-4-yn-1-yl)-1H-pyrazole-5-carboxylate

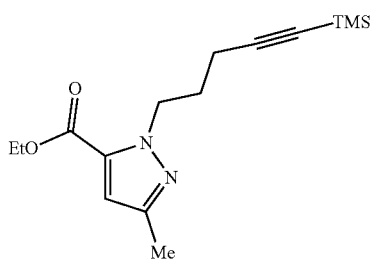 [SMILES: CCOC(=O)c1cc(C)nn1CCCC#C[Si](C)(C)C]

A mixture of ethyl 3-methyl-1H-pyrazole-5-carboxylate (22 g, 143 mmol), (5-chloropent-1-yn-1-yl)trimethylsilane (24.94 g, 143 mmol), $K_2CO_3$ (39.4 g, 285 mmol), and DMF (4 mL) was stirred at 60° C. overnight under a nitrogen gas atmosphere. The mixture was then dissolved in DCM and washed with water. The organic phase was dried over anhydrous $Na_2SO_4$, filtered, concentrated under reduced pressure, and purified by column chromatography on silica gel (petroleum ether/EtOAc=10:1) to afford ethyl 3-methyl-1-(5-(trimethylsilyl)pent-4-yn-1-yl)-1H-pyrazole-5-carboxylate (12.5 g, 42.7 mmol, 30% yield) as a colorless oil. LCMS (LCMS Method A): Rt=2.43 min, $[M+H]^+$=293.

Step 2

Ethyl 3-methyl-1-(pent-4-yn-1-yl)-1H-pyrazole-5-carboxylate

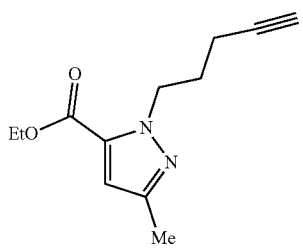 [SMILES: C#CCCCn1nc(C)cc1C(=O)OCC]

A mixture of ethyl 3-methyl-1-(5-(trimethylsilyl)pent-4-yn-1-yl)-1H-pyrazole-5-carboxylate (37.7 g, 129 mmol), $K_2CO_3$ (44.5 g, 322 mmol), and EtOH (800 mL) was stirred at rt overnight. The mixture was then filtered and the filtrate was concentrated under reduced pressure. The residue was dissolved in DCM, washed with water, dried over anhydrous $Na_2SO_4$, filtered, and concentrated under reduced pressure to afford ethyl 3-methyl-1-(pent-4-yn-1-yl)-1H-pyrazole-5-carboxylate (20 g, 91 mmol, 70.4% yield) as a colorless oil. LCMS (LCMS Method A): Rt=2.08 min, $[M+H]^+$=221.

Step 3

Benzyl 1-ethyl-3-methyl-1H-pyrazole-5-carboxylate

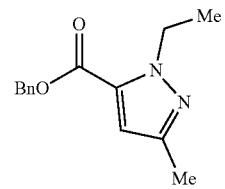 [SMILES: CCn1nc(C)cc1C(=O)OCc1ccccc1]

A mixture of 1-ethyl-3-methyl-1H-pyrazole-5-carboxylic acid (20 g, 130 mmol), (bromomethyl)benzene (22.2 g, 130 mmol), $K_2CO_3$ (26.9 g, 195 mmol), and DMF (200 mL) was stirred at 60° C. overnight. The mixture was then dissolved in DCM, washed with water, dried over anhydrous $Na_2SO_4$, filtered, concentrated under reduced pressure, and purified by column chromatography on silica gel (petroleum ether/EtOAc=10:1) to afford benzyl 1-ethyl-3-methyl-pyrazole-5-carboxylate (31.4 g, 129 mmol, 99% yield) as a colorless oil. LCMS (LCMS Method A): Rt=2.09 min, $[M+H]^+$=245.

Step 4

Benzyl 1-ethyl-4-iodo-3-methyl-1H-pyrazole-5-carboxylate

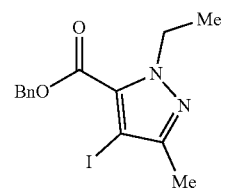 [SMILES: CCn1nc(C)c(I)c1C(=O)OCc1ccccc1]

A mixture of benzyl 1-ethyl-3-methyl-1H-pyrazole-5-carboxylate (31.6 g, 129 mmol), 1-iodopyrrolidine-2,5-dione (34.9 g, 155 mmol) and DMF (400 mL) was stirred at 90° C. for 2 days. The mixture was then allowed to cool to rt, dissolved in DCM, and washed with a saturated aqueous sodium thiosulfate solution. The organic layer was dried over anhydrous $Na_2SO_4$, filtered, concentrated under reduced pressure, and purified by column chromatography (petroleum ether/EtOAc=10:1) to afford benzyl 1-ethyl-4-iodo-3-methyl-1H-pyrazole-5-carboxylate (42.6 g, 115 mmol, 89% yield). LCMS (LCMS Method A): Rt=2.31 min, $[M+H]^+$=371.

Step 5

Benzyl 4-(5-(5-(ethoxycarbonyl)-3-methyl-1H-pyrazol-1-yl)pent-1-yn-1-yl)-1-ethyl-3-methyl-1H-pyrazole-5-carboxylate

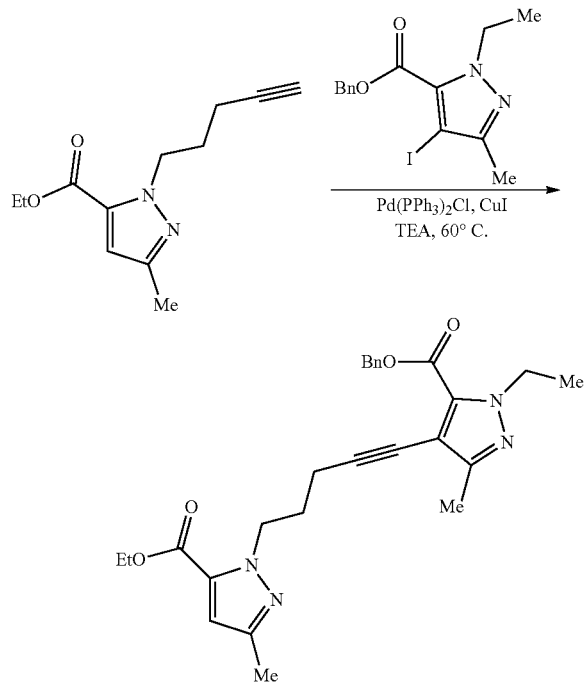

A mixture of ethyl 3-methyl-1-(pent-4-yn-1-yl)-1H-pyrazole-5-carboxylate (10.0 g, 45.4 mmol), benzyl 1-ethyl-4-iodo-3-methyl-1H-pyrazole-5-carboxylate (16.8 g, 45.4 mmol), copper(I) iodide (0.864 g, 4.54 mmol), bis(triphenylphosphine)palladium(II) chloride (0.319 g, 0.454 mmol), and Et$_3$N (200 mL) was stirred at 60° C. overnight under a nitrogen gas atmosphere. The mixture was then dissolved in DCM and washed with water. The organic phase was dried over anhydrous Na$_2$SO$_4$, filtered, concentrated under reduced pressure, and purified by column chromatography on silica gel (petroleum ether/EtOAc=5:1) to afford benzyl 4-(5-(5-(ethoxycarbonyl)-3-methyl-H-pyrazol-1-yl)pent-1-yn-1-yl)-1-ethyl-3-methyl-1H-pyrazole-5-carboxylate (9.5 g, 20.5 mmol, 45.3% yield) as a yellow solid. LCMS (LCMS Method B): Rt=2.66 min, [M+H]$^+$=463.

Step 6

4-(5-(5-(Ethoxycarbonyl)-3-methyl-1H-pyrazol-1-yl)pentyl)-1-ethyl-3-methyl-1H-pyrazole-5-carboxylic acid

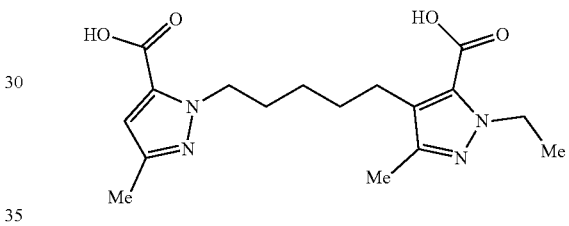

A mixture of benzyl 4-(5-(5-(ethoxycarbonyl)-3-methyl-1H-pyrazol-1-yl)pent-1-yn-1-yl)-1-ethyl-3-methyl-1H-pyrazole-5-carboxylate (19.0 g, 41.10 mmol), 10% Pd/C (0.22 g, 2.05 mmol), and THF (500 mL) was stirred at rt under a hydrogen gas atmosphere (4 atm) for 2 days. The reaction mixture was then filtered and concentrated under reduced pressure. The residue obtained was recrystallized from EtOAc/petroleum ether (1:5, v/v) to afford 4-(5-(5-(ethoxycarbonyl)-3-methyl-pyrazol-1-yl)pentyl)-1-ethyl-3-methyl-pyrazole-5-carboxylic acid (10.5 g, 27.90 mmol, 67.9% yield). $^1$H-NMR (400 MHz, CDCl$_3$) δ NMR (400 MHz, CDCl, v/v) to afford 4-(5-(5-(ethoxycarbonyl)-3-methyl-pyrazol-1-yl)pentyl)-1-ethyl-3-methyl-pyrazole-5-carboxylic acid (10.5 g, 27.90 mmol, 67.9% yield). $^1$H-NMR (400 MHz, CDCl$_3$) δ ppm 6.63 (s, 1H), 4.57-4.48 (m, 4H), 4.38-4.32 (m, 2H), 2.74-2.62 (m, 2H), 2.32 (s, 3H), 2.23 (s, 3H), 1.91-1.86 (m, 2H), 1.59-1.54 (m, 2H), 1.45-1.37 (m, 8H). LCMS (LCMS Method A): Rt=1.59 min, [M+H]$^+$=377.

Step 7

4-4-(7-(5-Carboxy-3-methyl-1H-pyrazol-1-yl)heptyl)-1-ethyl-3-methyl-1H-pyrazole-5-carboxylic acid

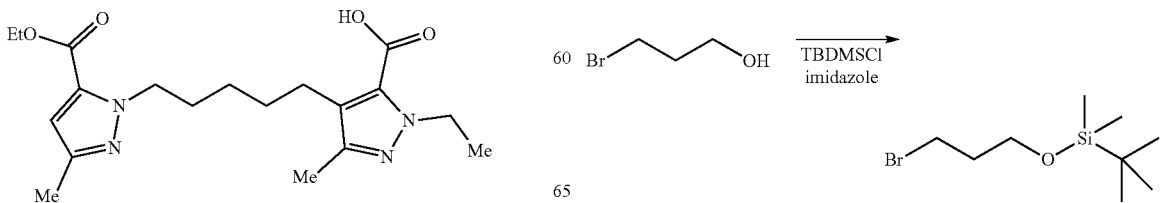

To a suspension of 4-(5-(5-(ethoxycarbonyl)-3-methyl-1H-pyrazol-1-yl)pentyl)-1-ethyl-3-methyl-1H-pyrazole-5-carboxylic acid (9.0 g, 23.9 mmol) in MeOH (120 mL) and water (120 mL) stirred at rt was added a 2 M aq. NaOH solution (60 mL, 119.5 mmol). The reaction mixture was stirred at rt for 30 min. The mixture was then acidified to pH 4 with the addition of a 6 M HCl solution upon which a solid precipitated from the reaction mixture. The solid was collected by filtration and dried under reduced pressure to afford 4-(5-(5-carboxy-3-methyl-1H-pyrazol-1-yl)pentyl)-1-ethyl-3-methyl-1H-pyrazole-5-carboxylic acid (6.5 g, 18.7 mmol, 78.1% yield) as a white solid. $^1$H-NMR (400 MHz, DMSO-d6) δ ppm 6.57 (s, 1H), 4.40-4.34 (m, 4H), 2.53 (t, J=7.6 Hz, 2H), 2.16 (s, 3H), 2.09 (s, 3H), 1.74-1.67 (m, 2H), 1.44-1.37 (m, 2H), 1.27-1.16 (m, 5H). LCMS (LCMS Method A): Rt=1.40 min, [M+H]$^+$=349.

Intermediate 3

(3-Bromopropoxy)(tert-butyl)dimethylsilane

To 1H-imidazole (13.4 g, 197 mmol) in DCM (100 mL) was added 3-bromopropan-1-ol (13.7 g, 99 mmol) followed slowly by tert-butylchlorodimethylsilane (17.8 g, 118 mmol) in DCM (20 ml). After 3 hr at RT, the reaction was concentrated to ~100 mL and poured in EtOAc (800 mL), washed with 5% aq citric acid (2×200 mL) and brine. The organic layer was dried over MgSO$_4$, filtered and concentrated to yield the title compound (10.0 g, 39.5 mmol, 40% yield). $^1$H NMR (400 MHz, chloroform-d) δ ppm 3.78 (t, J=5.70 Hz, 2H), 3.56 (t, J=6.46 Hz, 2H), 2.07 (t, J=5.83 Hz, 2H), 0.94 (s, 9H), 0.11 (s, 6H).

Intermediate 4

2,2,3,3-Tetrafluorobutane-1,4-diamine

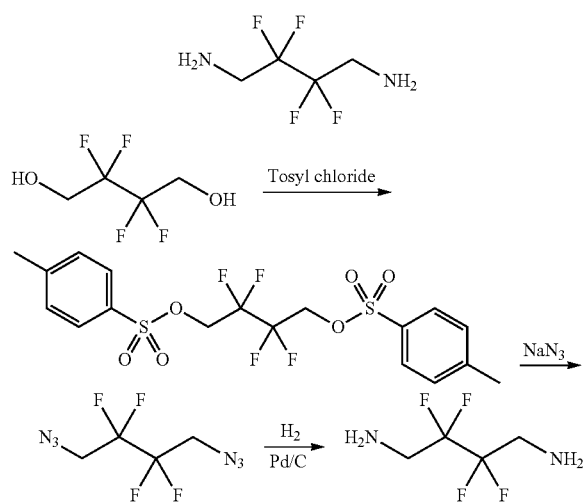

Step 1: 2,2,3,3-Tetrafluorobutane-1,4-diyl bis(4-methylbenzenesulfonate

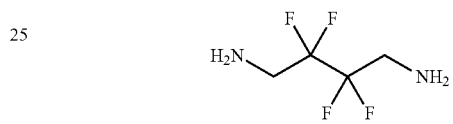

To 2,2,3,3-tetrafluorobutane-1,4-diol (10.0 g, 61.7 mmol) in pyridine (150 mL) at 0° C. was added 4-methylbenzene-1-sulfonyl chloride (29.4 g, 154 mmol) over 5 min, and then the reaction was heated to 55° C. After 1 day, the reaction was quenched with ice water, and the resulting solid was collected by filtration, dissolved in DCM (200 mL) and washed with 5% aq H$_2$SO$_4$ (100 mL×3). The organic layer was dried over Na$_2$SO$_4$ and concentrated to yield the title compound (27.3 g, 58.0 mmol, 94% yield) as a white solid. LCMS (LCMS Method A): Rt=1.750 min, [M+H]$^+$=470.9

Step 2: 1,4-Diazido-2,2,3,3-tetrafluorobutane

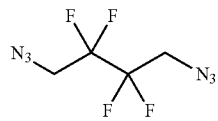 [SMILES: [N-]=[N+]=NCC(F)(F)C(F)(F)CN=[N+]=[N-]]

2,2,3,3-Tetrafluorobutane-1,4-diyl bis(4-methylbenzenesulfonate) (10.0 g, 21.3 mmol) and sodium azide (5.53 g, 85.0 mmol) in DMF (40 mL) was stirred at 110° C. overnight. The reaction was quenched with NaClO(aq) and extracted with DCM (5 mL×3). The combined organic layers were washed with water (10 mL), dried over Na$_2$SO$_4$ and concentrated to yield the title compound (3.5 g, 16.5 mmol, 78% yield). LCMS (LCMS Method A): Rt=1.520 min, [M+H]$^+$=213.1

Step 3: 2,2,3,3-Tetrafluorobutane-1,4-diamine

To a solution of 1,4-diazido-2,2,3,3-tetrafluorobutane (36.0 g, 170 mmol) in MeOH (350 mL) was added 10% Pd on carbon (18.1 g, 17.0 mmol). The reaction mixture was stirred at 40° C. under hydrogen (4 atm) for 16 hrs. The mixture was filtered through a pad of Celite, washed with MeOH and the filtrate was concentrated in vacuo to yield the title compound (22.0 g, 124 mmol, 73% yield). $^1$H NMR (400 MHz, chloroform-d) δ ppm 3.12-3.37 (m, 4H), 1.43 (br. s., 4H).

Intermediate 5

1-ethyl-3-methyl-1H-pyrazole-5-carbonyl isothiocyanate

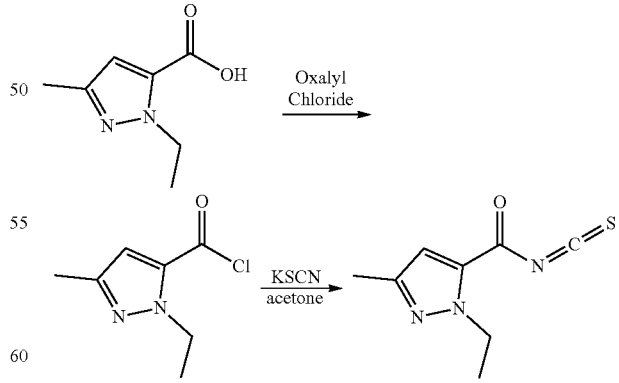

To a 1 L round bottom flask was added 1-ethyl-3-methyl-1H-pyrazole-5-carboxylic acid (25 g, 162 mmol) and DCM (500 mL). To this heterogeneous solution was added DMF (0.1 mL, 1.291 mmol) followed by the slow addition of oxalyl chloride (15.61 mL, 178 mmol). During the addition, bubbling was noticed. After stirring for 1 hr at room temperature, the volatiles were removed under vacuum and the crude was co-evaporated twice with dichloromethane (100 mL each). It was assumed 100% yield and the crude (1-ethyl-3-methyl-1H-pyrazole-5-carbonyl chloride (28.0 g, 162 mmol, 100% yield)) was used directly as it is in the next reaction.

To a dry 1 L round bottom flask was added KSCN (18.92 g, 195 mmol) and acetone (463 ml). This clear homogenous solution was cooled to 0° C. After 5 min. stirring at 0° C., 1-ethyl-3-methyl-1H-pyrazole-5-carbonyl chloride (28 g, 162 mmol) was added as a solution in acetone (25 mL). Once the addition was complete, the reaction was allowed to stir at 0° C. After 1 min. Additional KSCN was added (2 g) and the reaction was stirred for an additional 20 min. At this time, hexanes (200 mL) was added to the reaction mixture and the crude heterogeneous solution was concentrated in vacuo to one third of the volume. The process of hexanes addition and concentration was repeated twice (300 mL of Hexanes each). After the last concentration, hexanes (200 mL) were added and the solid was removed by filtration, rinsing with hexanes (100 mL). The resulting clear light yellow filtrate concentrated and purified by chromatography (330 g Gold silica column; eluting with 0-20% EtOAc/hexanes). The desired product elutes at 7% EtOAc/hexanes. The desired fractions were combined and concentrated yielding 1-ethyl-3-methyl-1H-pyrazole-5-carbonyl isothiocyanate (27.5 g, 139 mmol, 86% yield) as a clear colorless liquid. 1H NMR (400 MHz, chloroform-d) δ ppm 6.77 (s, 1H), 4.54 (q, J=7.10 Hz, 2H), 2.34 (s, 3H), 1.44 (t, J=7.22 Hz, 3H); LCMS (LCMS Method D): Rt=1.16 min, [M+H]$^+$=196.1. The acylisothiocyanate product degrades over time, and so a 0.4 M 1,4-dioxane solution was prepared and frozen to avoid/slow decomposition. This solution was thawed and used directly in subsequent reactions.

Intermediate 6

(E)-1-(4-Aminobut-2-en-1-yl)-2-(1-ethyl-3-methyl-1H-pyrazole-5-carboxamido)-1H-benzo[d]imidazole-5-carboxamide hydrochloride

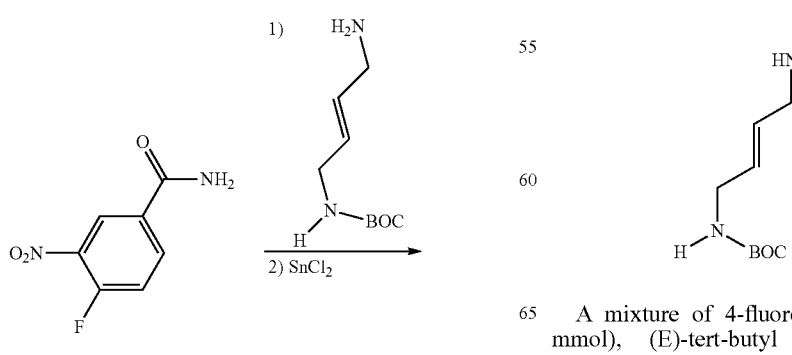

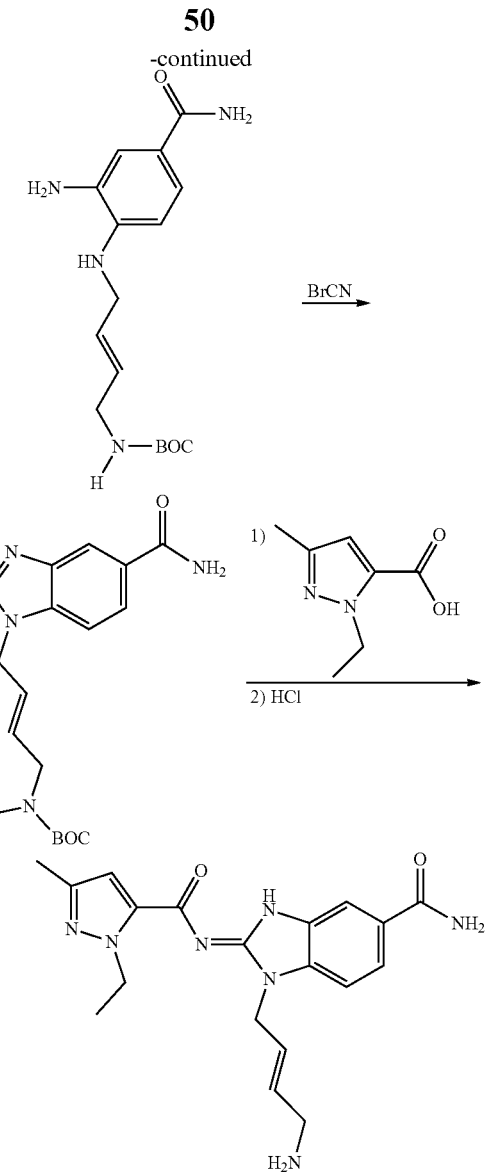

Step 1: (E)-tert-Butyl (4-((4-carbamoyl-2-nitrophenyl)amino)but-2-en-1-yl)carbamate

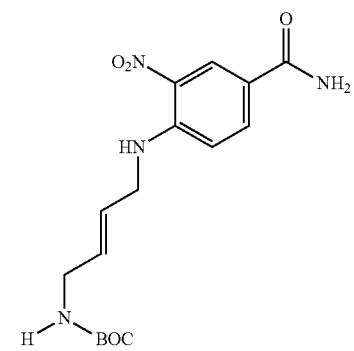 [SMILES: CC(C)(C)OC(=O)NC/C=C/CNc1ccc(C(N)=O)cc1[N+](=O)[O-]]

A mixture of 4-fluoro-3-nitrobenzamide (10.0 g, 54.3 mmol), (E)-tert-butyl (4-aminobut-2-en-1-yl)carbamate (10.62 g, 57.0 mmol) and K$_2$CO$_3$ (15.01 g, 109 mmol) in DMSO (200 mL) was stirred at RT overnight. The reaction was poured into water (2000 mL) and stirred for 30 min. The resulting solid was collected by filtration to yield the title compound (18.3 g, 52.2 mmol, 96% yield). LCMS (LCMS Method A): Rt=1.38 min, [2M+H]⁺=700.5

Step 2: (E)-tert-Butyl (4-((2-amino-4-carbamoylphenyl)amino)but-2-en-1-yl)carbamate

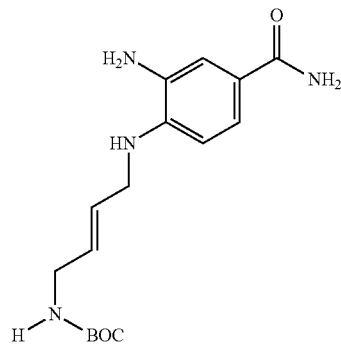

To (E)-tert-butyl (4-((4-carbamoyl-2-nitrophenyl)amino)but-2-en-1-yl)carbamate (18.3 g, 52.2 mmol) in DMF (300 mL) was added stannous chloride dihydrate (58.9 g, 261 mmol). After stirring at RT overnight, the reaction was added to sat aq NaHCO₃ (2000 mL), dropwise, and extracted with EtOAc (5×500 mL). The combined organic layers were washed with brine (200 mL), dried over Na₂SO₄, filtered and concentrated to yield the title compound (16.5 g, 51.5 mmol, 99% yield) as a yellow oil. LCMS (LCMS Method A): Rt=1.275 min, [M-BOC+H]⁺=221.1

Step 3: (E)-tert-Butyl (4-(2-amino-5-carbamoyl-1Hbenzo[d]imidazol-1-yl)but-2-en-1-yl)carbamate

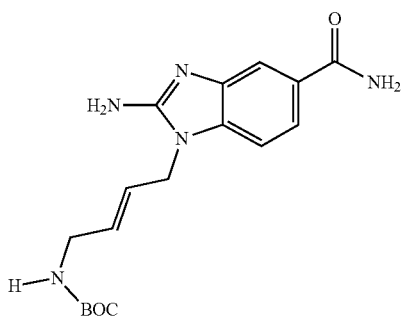 [SMILES: CC(C)(C)OC(=O)NC/C=C/Cn1c(N)nc2cc(C(N)=O)ccc21]

A mixture of (E)-tert-butyl (4-((2-amino-4-carbamoylphenyl)amino)but-2-en-1-yl)carbamate (16.5 g, 51.5 mmol) and cyanogen bromide (8.18 g, 77 mmol) in THF (200 mL) was heated to reflux overnight. The reaction was cooled to room temperature, diluted with sat aq NaHCO₃ (500 mL), and extracted with EtOAc (5×300 mL). The combined organic layers were washed with brine, dried over Na₂SO₄, filtered and concentrated. The residue was purified over silica gel, eluting with 50:1 to 20:1 DCM in MeOH (+3% NH₄OH) to yield the title compound (13.7 g, 39.7 mmol, 77% yield) as an off-white solid. LCMS (LCMS Method A): Rt=1.150 min, [M+H]⁺=346.1

Step 4: (E)-tert-Butyl(4-(5-carbamoyl-2-(1-ethyl-3-methyl-1H-pyrazole-5-carboxamido)-1H-benzo[d]imidazol-1-yl)but-2-en-1-yl)carbamate

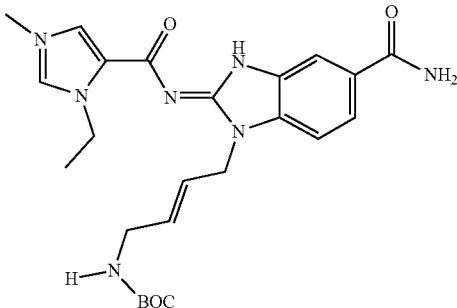

To 1-ethyl-3-methyl-1H-pyrazole-5-carboxylic acid (9.17 g, 59.5 mmol) in DCM (500 mL) at 0° C. was added EDC (20.53 g, 107 mmol) and HOBT (18.22 g, 119 mmol). After 15 min, a mixture of (E)-tert-butyl (4-(2-amino-5-carbamoyl-1H-benzo[d]imidazol-1-yl)but-2-en-1-yl)carbamate (13.7 g, 39.7 mmol) in DMF (50 mL) was added, followed by TEA (27.6 mL, 198 mmol). The reaction was warmed to RT, stirred overnight and concentrated. The residue was diluted with water (500 mL) and extracted with ethyl acetate (3×300 mL), and the combined organic phases were washed with brine, dried over Na₂SO₄, filtered and concentrated. The residue was purified over silica gel, eluting with 50:1 to 20:1 DCM: MeOH to give the crude product, which was washed with DCM 15 (300 mL) and collected by filtration to yield the title compound (14.0 g, 29.1 mmol, 73% yield) as an off-white solid. ¹H NMR (400 MHz, DMSO-d₆) δ ppm 12.84 (s, 1H), 8.00-7.97 (m, 2H), 7.80-7.78 (m, 1H), 7.49 (d, J=8.4 Hz, 1H), 7.34 (s, 1H), 6.95 (t, J=5.5 Hz, 1H), 6.66 (s, 1H), 5.73-5.65 (m, 2H), 4.83 (d, J=4.3 Hz, 2H), 4.62 (q, J=7.0 Hz, 2H), 3.52 (s, 2H), 2.18 (s, 3H), 1.38-1.33 (m, 12H); LCMS (LCMS Method A): Rt=1.409 min, [M+H]⁺=482.0

Step 5: (E)-1-(4-Aminobut-2-en-1-yl)-2-(1-ethyl-3-methyl-1H-pyrazole-5-carboxamido)-1H-benzo[d]imidazole-5-carboxamide hydrochloride

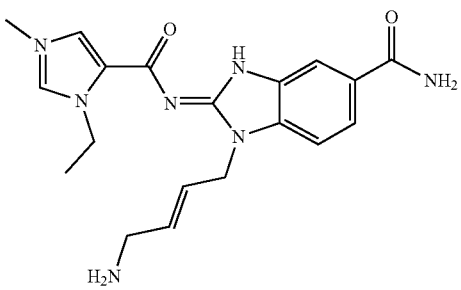

To a suspension of (E)-tert-butyl (4-(5-carbamoyl-2-(1-ethyl-3-methyl-1H-pyrazole-5-carboxamido)-1H-benzo[d]imidazol-1-yl)but-2-en-1-yl)carbamate (3.00 g, 6.23 mmol) in dioxane (60 mL) was added 4N HCl in dioxane (15.6 mL, 62.3 mmol), followed by MeOH (15 mL) to dissolve some remaining solid. After 30 min at RT, the reaction mixture became cloudy and was allowed to stir for approximately 3 days. The resulting solid was collected by filtration and washed with DCM to yield the title compound (2.0 g, 4.8 mmol, 77% yield) as a white solid. $^1$H NMR (400 MHz, DMSO-$d_6$) δ ppm 7.97-8.09 (br. s., 1H), 7.82 (d, J=8.11 Hz, 1H), 7.50 (d, J=8.11 Hz, 1H), 7.38 (br. s., 1H), 6.70 (s, 1H), 5.97-6.08 (m, 1H), 5.68-5.80 (m, 1H), 4.91 (d, J=4.31 Hz, 2H), 4.60 (q, J=6.67 Hz, 2H), 3.42 (br. s., 2H), 2.18 (s, 3H), 1.36 (t, J=6.97 Hz, 3H); LCMS (LCMS Method D): Rt=0.53 min, [M+H]$^+$=382.2

Intermediate 7

1-(5-(5-(ethoxycarbonyl)-1-ethyl-3-methyl-1H-pyrazol-4-yl)pentyl)-3-methyl-1H-pyrazole-5-carboxylicacid

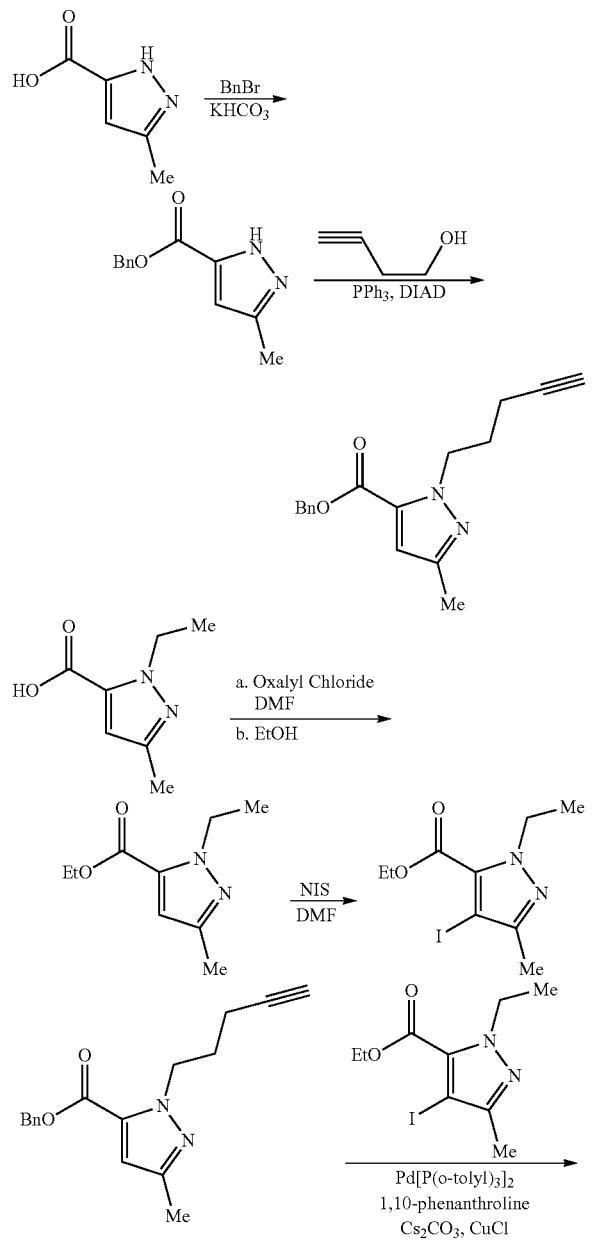

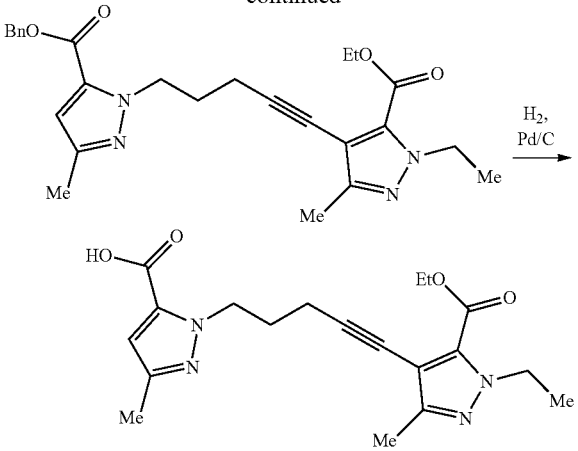

Step 1: benzyl 3-methyl-H-pyrazole-5-carboxylate

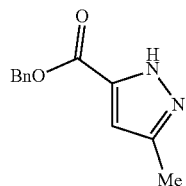 [SMILES: Cc1cc(C(=O)OCc2ccccc2)[nH]n1]

A mixture of 3-methyl-1H-pyrazole-5-carboxylic acid (50 mg, 0.396 mmol) and KHCO$_3$ (47.6 mg, 0.476 mmol) in DMSO (2 mL) was stirred for 30 min, and (bromomethyl)benzene (0.045 mL, 0.377 mmol) was added. The mixture was stirred for 4 h at RT, diluted with EtOAc (20 mL), washed with water and brine, and dried over Na$_2$SO$_4$. The mixture was filtered and concentrated, and the residue was purified by column chromatography (Combiflash, 0-50% EtOAc in hexane) to afford the title compound (66 mg, 0.305 mmol, 77% yield) as a white solid. $^1$H NMR (400 MHz, DMSO-$d_6$) δ ppm 13.19 (br. s., 1H) 7.34-7.48 (m, 5H) 6.52 (s, 1H) 5.29 (s, 2H) 2.27 (s, 3H). LCMS (LCMS Method D): Rt=0.86 min, [M+H]$^+$=216.9.

Step 2: benzyl 3-methyl-1-(pent-4-yn-1-yl)-1H-pyrazole-5-carboxylate

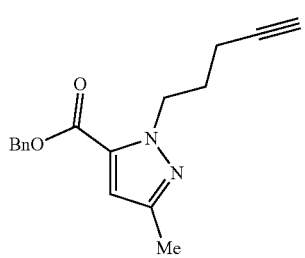 [SMILES: C#CCCCn1nc(C)cc1C(=O)OCc1ccccc1]

A mixture of DIAD (25.9 mL, 133 mmol) and triphenylphosphine (34.9 g, 133 mmol) in tetrahydrofuran (THF) (600 mL) was stirred for 30 min at 0° C., and pent-4-yn-1-ol (11.36 mL, 122 mmol) was then added. The mixture was stirred for 30 min, and benzyl 3-methyl-1H-pyrazole-5- carboxylate (24 g, 111 mmol) was added. It was allowed to warm to RT and stirred overnight. The reaction was diluted with EtOAc (1000 mL), washed with saturated NaHCO$_3$, and brine, dried over Na$_2$SO$_4$, filtered and concentrated. The oily residue was treated with 10% EtOAc in hexane (500 mL), and a white precipitate formed. The precipitate was filtered off and washed with 10% EtOAc in hexane. The combined filtrates were concentrated, and the residue was purified by column chromatography (Combiflash, 0-15% EtOAc in hexane) to afford the title compound (27.5 g, 97 mmol, 88% yield) as a white solid. $^1$H NMR (400 MHz, CHLOROFORM-d) δ ppm 7.34-7.47 (m, 5H) 6.68 (s, 1H) 5.33 (s, 2H) 4.63 (t, J=7.03 Hz, 2H) 2.30 (s, 3H) 2.19-2.26 (m, 2H) 2.09 (quin, J=7.09 Hz, 2H) 1.97 (br. s., 1H); LCMS (LCMS Method D): Rt=1.21 min, [M+H]$^+$=283.0.

Step 3: ethyl 1-ethyl-3-methyl-1H-pyrazole-5-carboxylate

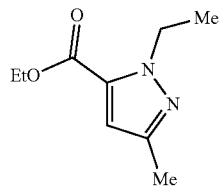 [SMILES: CCOC(=O)c1cc(C)nn1CC]

Oxalyl chloride (5.68 ml, 64.9 mmol) was added to a suspension of 1-ethyl-3-methyl-1H-pyrazole-5-carboxylic acid (5 g, 32.4 mmol) in DCM (40 mL) at RT under N$_2$ and two drops of DMF were added. The mixture was stirred for 2 hours at RT, concentrated and dried in vacuo. Ethanol (50 ml, 856 mmol) was added, and the mixture was stirred for 1 hour at RT. The reaction was concentrated and dried in vacuo to give a light-yellow oil which was taken into EtOAc (100 mL), washed with saturated NaHCO$_3$ and brine, dried over Na$_2$SO$_4$, filtered, concentrated and the resulting residue was dried in vacuo to give the title compound (5.5 g, 30.2 mmol, 93% yield) as a light-yellow oil. $^1$H NMR (400 MHz, CHLOROFORM-d) δ ppm 6.63 (s, 1H) 4.56 (q, J=7.11 Hz, 2H) 4.35 (q, J=7.11 Hz, 2H) 2.30 (s, 3H) 1.44 (t, J=7.28 Hz, 3H) 1.39 (t, J=7.28 Hz, 3H). LCMS (LCMS Method E): Rt=0.81 min, [M+H]$^+$=183.1.

Step 4: ethyl 1-ethyl-4-iodo-3-methyl-1H-pyrazole-5-carboxylate

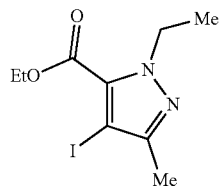 [SMILES: CCOC(=O)c1c(I)c(C)nn1CC]

A mixture of ethyl 1-ethyl-3-methyl-1H-pyrazole-5-carboxylate (5.5 g, 30.2 mmol) and NIS (8.15 g, 36.2 mmol) in DMF (100 mL) was heated to 90° C. and stirred for 3 days under N2. The reaction was cooled to RT, diluted with EtOAc (200 mL), washed with saturated Na$_2$S2O3, 5% LiCl, and brine, dried over Na$_2$SO$_4$, filtered, concentrated, and the resulting residue was purified by column chromatography (Combiflash, 0-7% EtOAc in hexane) to afford the title compound (9.1 g, 29.5 mmol, 98% yield) as a colorless oil. $^1$H NMR (400 MHz, CHLOROFORM-d) δ ppm 4.57 (q, J=7.03 Hz, 2H) 4.43 (q, J=7.03 Hz, 2H) 2.32 (s, 3H) 1.45-1.50 (m, 3H) 1.39-1.45 (m, 3H). LCMS (LCMS Method D): Rt=1.12 min, [M+H]$^+$=308.9.

Step 5: 1 ethyl 4-(5-(5-((benzyloxy)carbonyl)-3-methyl-1H-pyrazol-1-yl)pent-1-yn-1-yl)-1-ethyl-3-methyl-1H-pyrazole-5-carboxylate

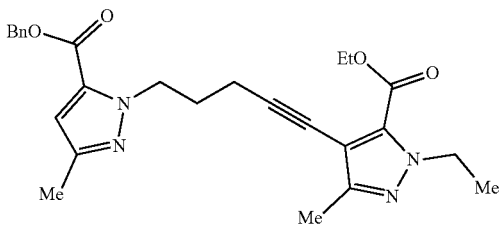 [SMILES: CCOC(=O)c1c(C#CCCCn2nc(C)cc2C(=O)OCc2ccccc2)c(C)nn1CC]

A flask which was previously purged with nitrogen was charged with Cs$_2$CO$_3$ (23.08 g, 70.8 mmol), 1,10-phenanthroline (1.915 g, 10.63 mmol), copper(I) chloride (0.175 g, 1.771 mmol), benzyl 3-methyl-1-(pent-4-yn-1-yl)-1H-pyrazole-5-carboxylate (10 g, 35.4 mmol), ethyl 1-ethyl-4-iodo-3-methyl-1H-pyrazole-5-carboxylate (13.10 g, 42.5 mmol), Pd[P(o-tollyl)$_3$]$_2$ (0.760 g, 1.063 mmol), and degassed Toluene (100 mL). The mixture was degassed for 15 min, heated to 100° C. and stirred overnight (18 hr) under N$_2$. The reaction was cooled to RT and diluted with EtOAc. The inorganic solids were filtered off and washed with EtOAc. The combined organics were concentrated and the residue was purified via silica gel chromatography (EtOAc/Hexanes 0-25%) to afford the title compound (11.38 g, 24.60 mmol, 69.5% yield) as a colorless oil. $^1$H NMR (400 MHz, CHLOROFORM-d) δ ppm 7.34-7.47 (m, 5H) 6.68 (s, 1H) 5.31 (s, 2H) 4.67 (t, J=7.03 Hz, 2H) 4.51 (q, J=7.19 Hz, 2H) 4.39 (q, J=7.03 Hz, 2H) 2.51 (t, J=7.28 Hz, 2H) 2.31 (s, 3H) 2.29 (s, 3H) 2.17 (t, J=7.15 Hz, 2H) 1.40 (t, J=7.03 Hz, 6H). LCMS (LCMS Method D): Rt=1.43 min, [M+H]$^+$=463.3.

Step 6:1-(5-(5-(ethoxycarbonyl)-1-ethyl-3-methyl-1H-pyrazol-4-yl)pentyl)-3-methyl-1H-pyrazole-5-carboxylicacid

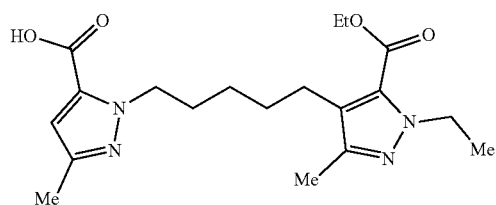 [SMILES: CCOC(=O)c1c(CCCCCn2nc(C)cc2C(=O)O)c(C)nn1CC]

To a flask charged with ethyl 4-(5-(5-((benzyloxy)carbonyl)-3-methyl-1H-pyrazol-1-yl)pent-1-yn-1-yl)-1-ethyl-3-methyl-1H-pyrazole-5-carboxylate (11.3 g, 24.43 mmol) and Pd/C (2.60 g, 2.443 mmol) was added ethanol (200 mL). The flask was purged with N$_2$, then hydrogen (via balloon) and the mixture was stirred under a H$_2$ atmosphere overnight (18 hr). The catalyst was filtered off and the filtrate was concentrated in vacuo to afford the title compound (8.89 g, 23.62 mmol, 97% yield) as a white solid. $^1$H NMR (400 MHz, DMSO-d$_6$) δ ppm 13.14 (br. s., 1H) 6.57 (s, 1H) 4.33-4.43 (m, 4H) 4.28 (m, J=7.09 Hz, 2H) 2.51-2.56 (m, 2H) 2.16 (s, 3H) 2.10 (s, 3H) 1.72 (m, J=7.34 Hz, 2H) 1.41 (m, J=7.58 Hz, 2H) 1.25-1.31 (m, 6H) 1.16-1.24 (m, 2H). LCMS (LCMS Method D): Rt=1.07 min, [M+H]$^+$=377.2.

Example 1
(E)-1-(4-(5-Carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-hydroxypropoxy)-1H-benzo[d]imidazole-5-carboxamide
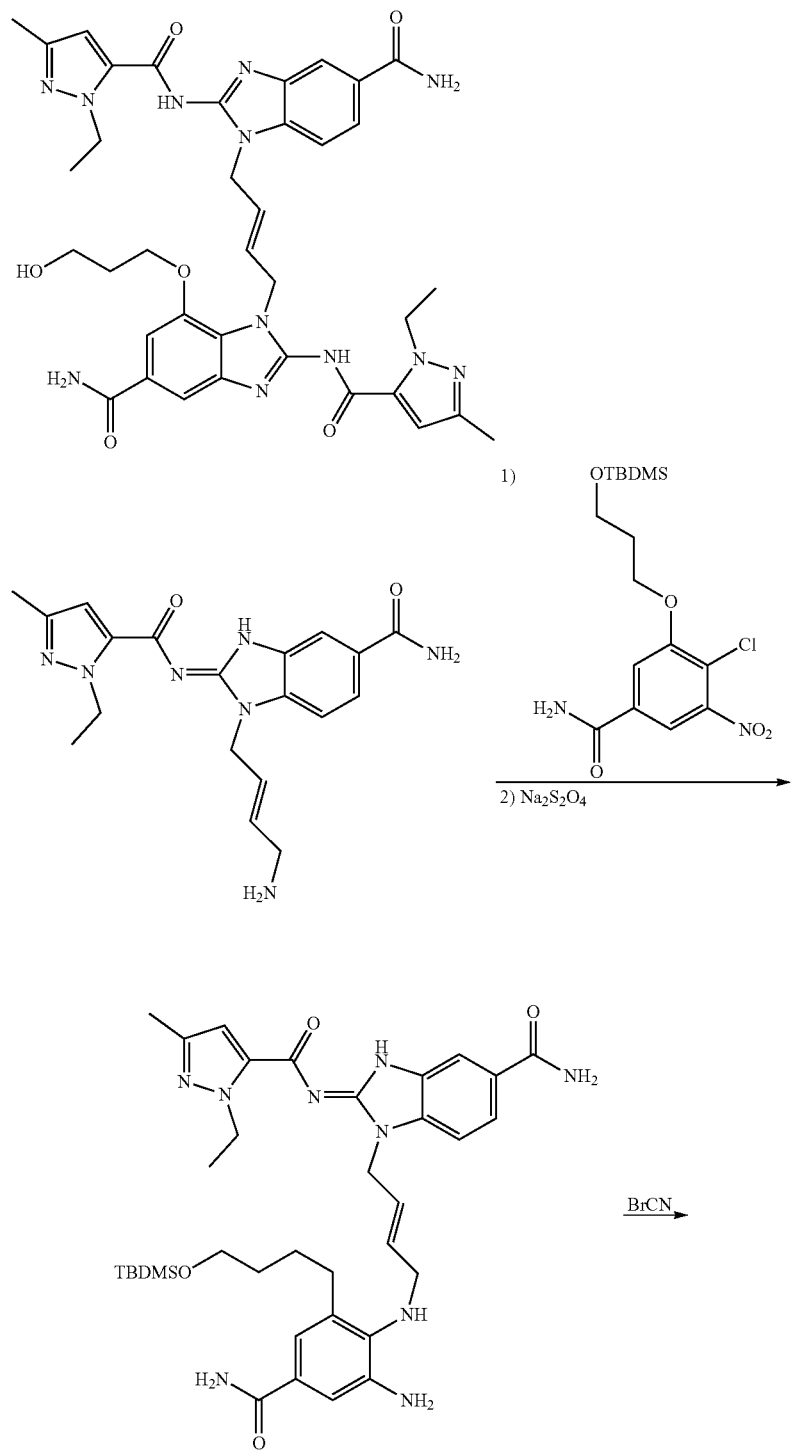

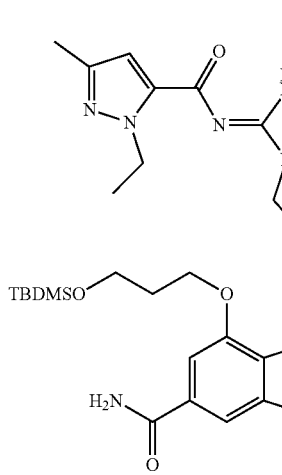 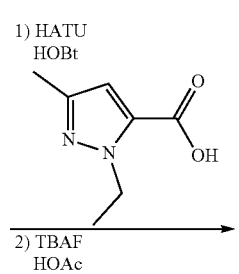 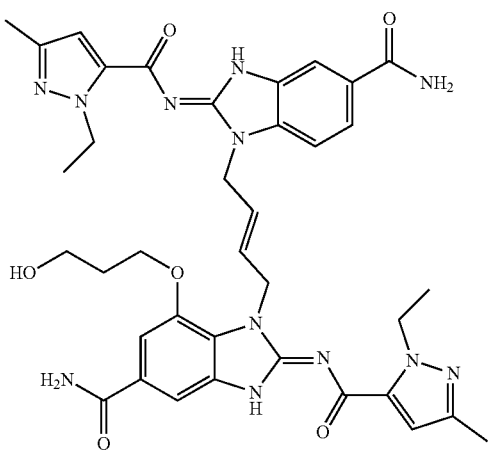

Step 1: (E)-1-(4-((2-(3-((tert-Butyldimethylsilyl)oxy)propoxy)-4-carbamoyl-6-nitrophenyl)amino)but-2-en-1-yl)-2-(1-ethyl-3-methyl-1H-pyrazole-5-carboxamido)-1H-benzo[d]imidazole-5-carboxamide

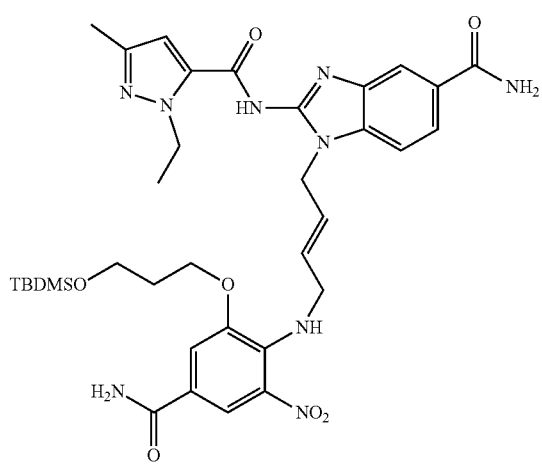 [SMILES: CCn1nc(C)cc1C(=O)Nc1nc2cc(C(N)=O)ccc2n1C/C=C/CNc1c(OCCCO[Si](C)(C)C(C)(C)C)cc(C(N)=O)cc1[N+](=O)[O-]]

A microwave tube containing (E)-1-(4-aminobut-2-en-1-yl)-2-(1-ethyl-3-methyl-1H-pyrazole-5-carboxamido)-1H-benzo[d]imidazole-5-carboxamide hydrochloride (517 mg, 1.24 mmol, in DMSO (10 mL) was treated with TEA (0.28 mL, 2.0 mmol), followed by $K_2CO_3$ (274 mg, 1.98 mmol) and 3-(3-((tert-butyldimethylsilyl)oxy)propoxy)-4-chloro-5-nitrobenzamide (385 mg, 0.990 mmol). The reaction was heated to 75° C. After 7 hr, the mixture was concentrated, and the residue was purified over silica gel, eluting with 10-90% EtOAc to remove impurities, followed by 0-10% MeOH in DCM to yield the title compound (200 mg, 0.273 mmol, 28% yield) as an orange solid. $^1$H NMR (400 MHz, DMSO-$d_6$) δ ppm 8.16 (d, J=1.52 Hz, 1H), 7.94-8.08 (m, 3H), 7.74 (d, J=8.11 Hz, 2H), 7.50 (s, 1H), 7.31-7.43 (m, 3H), 6.62 (s, 1H), 5.74-5.81 (m, 2H), 4.80 (br. s., 2H), 4.59 (d, J=6.84 Hz, 2H), 4.13 (br. s., 2H), 4.01 (t, J=6.08 Hz, 2H), 3.63 (t, J=5.96 Hz, 2H), 2.16 (s, 3H), 1.76-1.88 (m, 2H), 1.33 (t, J=7.10 Hz, 3H), 0.74-0.82 (m, 9H), −0.06 (s, 6H); LCMS (LCMS Method D): Rt=1.23 min, [M+H]$^+$=734.6

Step 2: (E)-1-(4-((2-Amino-6-(3-((tert-butyldimethylsilyl)oxy)propoxy)-4-carbamoylphenyl)amino)but-2-en-1-yl)-2-(1-ethyl-3-methyl-1Hpyrazole-5-carboxamido)-1H-benzo[d]imidazole-5-carboxamide

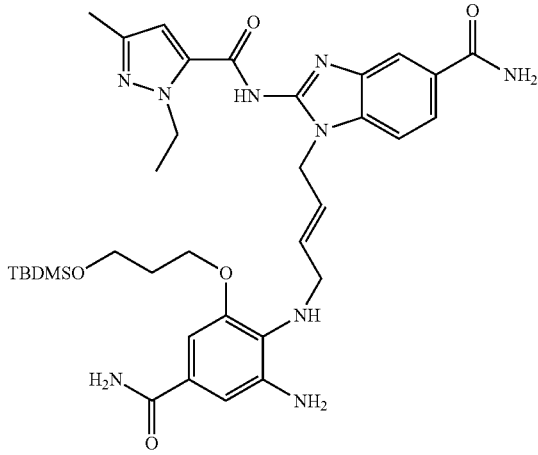

(E)-1-(4-((2-(3-((tert-butyldimethylsilyl)oxy)propoxy)-4-carbamoyl-6-nitrophenyl)amino)but-2-en-1-yl)-2-(1-ethyl-3-methyl-1H-pyrazole-5-carboxamido)-1H-benzo[d]imidazole-5-carboxamide (1 g, 1.363 mmol) was suspended in MeOH (20 mL) and ammonium hydroxide (4.62 mL, 34.1 mmol) was added and stirred for 5 mins at RT. Sodium hydrosulfite (1.675 g, 8.18 mmol) in Water (5 mL) was then added. After 60 mins, EtOAc (300 ml) was added and the mixture was extracted with water (50 ml×3). The organic phase was separated, dried with $Na_2SO_4$, and concentrated in vacuo to afford title compound (710 mg, 1.009 mmol, 74.0% yield) as light yellow solid which was used without further purification. $^1$H NMR (400 MHz, DMSO-$d_6$) δ ppm 12.80 (br. s., 1H), 8.00 (s, 1H), 7.97 (br. s., 1H), 7.75 (dd, J=8.49, 1.14 Hz, 1H), 7.63 (br. s., 1H), 7.28-7.41 (m, 2H), 7.00 (br. s., 1H), 6.84 (d, J=1.52 Hz, 1H), 6.74 (d, J=1.52 Hz, 1H), 6.65 (s, 1H), 5.79-5.96 (m, 1H), 5.64-5.78 (m, 1H), 4.81 (d, J=4.82 Hz, 2H), 4.68 (br. s., 2H), 4.61 (d, J=7.10 Hz, 2H), 3.92 (t, J=5.83 Hz, 2H), 3.84 (br. s., 1H), 3.63 (t, J=6.08 Hz, 2H), 3.57 (br. s., 2H), 2.17 (s, 3H), 1.70-1.82 (m, 2H), 1.34 (t, J=7.10 Hz, 3H), 0.68-0.83 (m, 9H), −0.06 (s, 6H); LCMS (LCMS Method J): Rt=1.05 min, [M+H]$^+$=704.3

Step 3: (E)-2-Amino-7-(3-((tert-butyldimethylsilyl)oxy)propoxy)-1-(4-(5-carbamoyl-2-(1-ethyl-3-methyl-1H-pyrazole-5-carboxamido)-1H-benzo[d]imidazol-1-yl)but-2-en-1-yl)-1H-benzo[d]imidazole-5-carboxamide

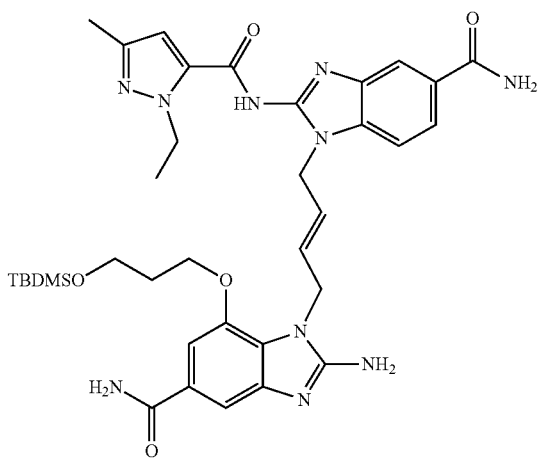 [SMILES: CCn1nc(C)cc1C(=O)Nc1nc2cc(C(N)=O)ccc2n1C/C=C/Cn1c(N)nc2cc(C(N)=O)cc(OCCCO[Si](C)(C)C(C)(C)C)c21]

To a solution of (E)-1-(4-((2-amino-6-(3-((tert-butyldimethylsilyl)oxy)propoxy)-4-carbamoylphenyl)amino)but-2-en-1-yl)-2-(1-ethyl-3-methyl-1H-pyrazole-5-carboxamido)-1H-benzo[d]imidazole-5-carboxamide (120 mg, 0.170 mmol) in MeOH (5 mL) was added cyanogen bromide (36 mg, 0.34 mmol) at RT. After 2 hr, the reaction was concentrated, and EtOAc was added (10 mL). After stirring 30 min, the solid was isolated by filtration, and washed with EtOAc to yield the title compound (120 mg, 0.165 mmol, 97% yield) as a light brown solid, which was used without further purification. $^1$H NMR (400 MHz, MeOH-d4) δ ppm 8.00 (d, J=1.27 Hz, 1H), 7.81 (dd, J=8.36, 1.77 Hz, 1H), 7.49 (d, J=1.27 Hz, 1H), 7.39-7.45 (m, 1H), 7.36 (d, J=1.27 Hz, 1H), 6.61 (s, 1H), 5.82-5.99 (m, 2H), 4.96-5.01 (m, 2H), 4.56-4.65 (m, 2H), 4.12 (t, J=6.21 Hz, 2H), 3.62-3.75 (m, 2H), 2.18-2.29 (m, 3H), 1.79 (t, J=6.21 Hz, 2H), 1.24-1.54 (m, 5H), 0.84-0.98 (m, 9H), −0.01-0.11 (m, 6H); LCMS (LCMS Method D): Rt=0.97 min, [M+H]$^+$=729.5

Step 4: (E)-7-(3-((tert-Butyldimethylsilyl)oxy)propoxy)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazole-5-carboxamide

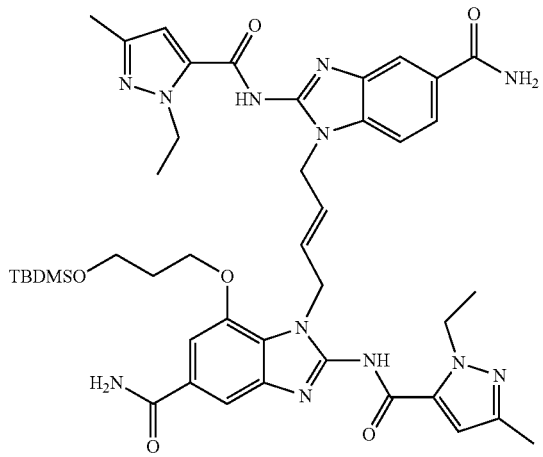 [SMILES: CCn1nc(C)cc1C(=O)Nc1nc2cc(C(N)=O)ccc2n1C/C=C/Cn1c(NC(=O)c2cc(C)nn2CC)nc2cc(C(N)=O)cc(OCCCO[Si](C)(C)C(C)(C)C)c21]

To a solution of 1-ethyl-3-methyl-1H-pyrazole-5-carboxylic acid (33 mg, 0.21 mmol) in DMF (3 mL) was added HATU (75 mg, 0.20 mmol) and HOBt (12.6 mg, 0.082 mmol). After stirring at RT 10 min, triethylamine (0.09 mL, 0.66 mmol) was added, followed by (E)-2-amino-7-(3-((tert-butyldimethylsilyl)oxy)propoxy)-1-(4-(5-carbamoyl-2-(1-ethyl-3-methyl-1H-pyrazole-5-carboxamido)-1H-benzo[d]imidazol-1-yl)but-2-en-1-yl)-1H-benzo[d]imidazole-5-carboxamide (120 mg, 0.165 mmol) and the reaction was continued at RT. After 3 days, a solid was precipitated out of the reaction by the dropwise addition of water. The solid was isolated by filtration and washed with water. The solid was then purified over silica gel (12 g HP Gold column), eluting with 0-20% MeOH in DCM. The desired fractions were combined and concentrated to yield the title compound (29 mg, 0.034 mmol, 20% yield) as an off-white solid. $^1$H NMR (400 MHz, THF-$d_4$) δ ppm 12.53 (br. s., 2H), 8.00 (d, J=1.01 Hz, 1H), 7.61 (d, J=1.01 Hz, 1H), 7.53 (dd, J=8.36, 1.52 Hz, 1H), 7.36 (d, J=6.84 Hz, 2H), 7.29 (d, J=1.01 Hz, 1H), 7.12 (d, J=8.36 Hz, 1H), 6.83 (br. s., 2H), 6.66 (d, J=2.28 Hz, 2H), 6.06 (dt, J=15.46, 5.58 Hz, 1H), 5.87 (dt, J=15.46, 5.83 Hz, 1H), 5.09 (d, J=5.32 Hz, 2H), 4.89 (d, J=5.58 Hz, 2H), 4.59-4.72 (m, 4H), 3.97 (t, J=6.21 Hz, 2H), 3.69 (t, J=5.96 Hz, 2H), 2.20 (s, 6H), 1.73-1.78 (m, 2H), 1.40 (td, J=7.03, 1.14 Hz, 6H), 0.82-0.94 (m, 9H), −0.03-0.09 (m, 6H); LCMS (LCMS Method D): Rt=1.21 min, [M/2+H]$^+$=433.6

Step 5: (E)-1-(4-(5-Carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-hydroxypropoxy)-1H-benzo[d]imidazole-5-carboxamide

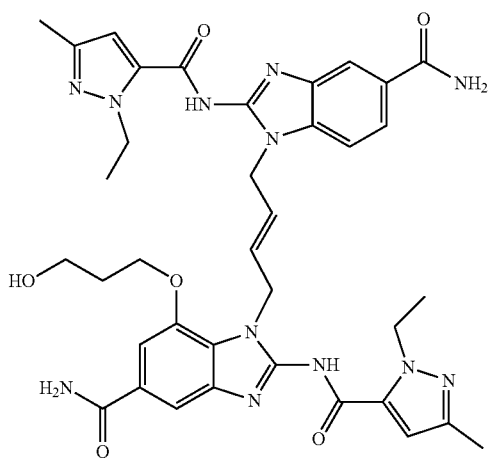 [SMILES: CCn1nc(C)cc1C(=O)Nc1nc2cc(C(N)=O)ccc2n1C/C=C/Cn1c(NC(=O)c2cc(C)nn2CC)nc2cc(C(N)=O)cc(OCCCO)c21]

To a solution of (E)-7-(3-((tert-butyldimethylsilyl)oxy)propoxy)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazole-5-carboxamide (25 mg, 0.029 mmol) and 1M TBAF in THF (0.058 mL, 0.058 mmol) in THF (2 mL) at RT was added acetic acid (3.3 L, 0.058 mmol). After 12 hr the reaction was concentrated, triturated with diethyl ether and EtOAc, and further purified over silica gel (12 g Gold column) eluting with 0-25% methanol in DCM. The desired fractions were concentrated to yield the title compound (7 mg, 9 μmole, 32% yield) as an off-white solid. $^1$H NMR (400 MHz, THF-d4) δ ppm 12.51 (br. s., 2H), 8.01 (d, J=1.01 Hz, 2H), 7.55-7.65 (m, 3H), 7.33 (d, J=1.01 Hz, 2H), 7.14-7.20 (m, 2H), 6.00-6.15 (m, 2H), 5.82-5.96 (m, 2H), 5.05-5.13 (m, 4H), 4.04 (t, J=6.59 Hz, 4H), 3.78-3.90 (m, 5H), 2.19 (d, J=2.03 Hz, 6H), 1.87-2.00 (m, 2H), 1.36-1.44 (m, 6H); LCMS (LCMS Method D): Rt=0.79 min, [M+H]$^+$=751.4.

The compound prepared by the above process may exist in a tautomeric or an isomeric form, e.g., as (E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-hydroxypropoxy)-2,3-dihydro-1H-benzo[d]imidazole-5-carboxamide

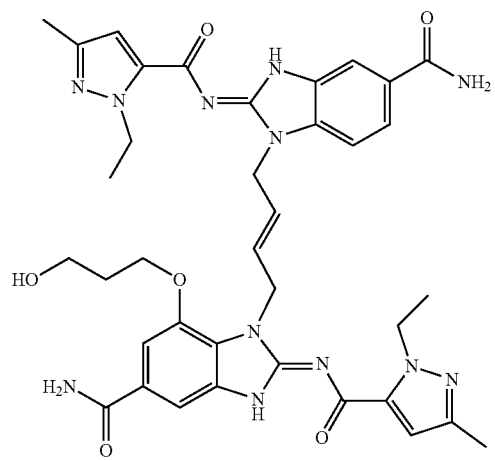 [SMILES: CCn1nc(C)cc1C(=O)/N=c1\[nH]c2cc(C(N)=O)ccc2n1C/C=C/Cn1/c(=N/C(=O)c2cc(C)nn2CC)[nH]c2cc(C(N)=O)cc(OCCCO)c21]

or (Z)-1-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-hydroxypropoxy)-2,3-dihydro-1H-benzo[d]imidazole-5-carboxamide

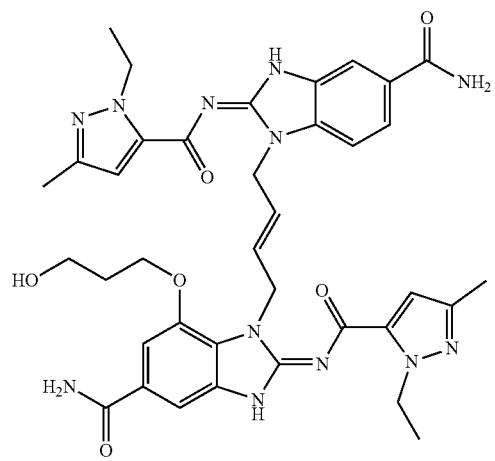 [SMILES: CCn1nc(C)cc1C(=O)/N=c1/[nH]c2cc(C(N)=O)ccc2n1C/C=C/Cn1/c(=N\C(=O)c2cc(C)nn2CC)[nH]c2cc(C(N)=O)cc(OCCCO)c21]

Example 2
(E)-1-(4-(5-Carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide
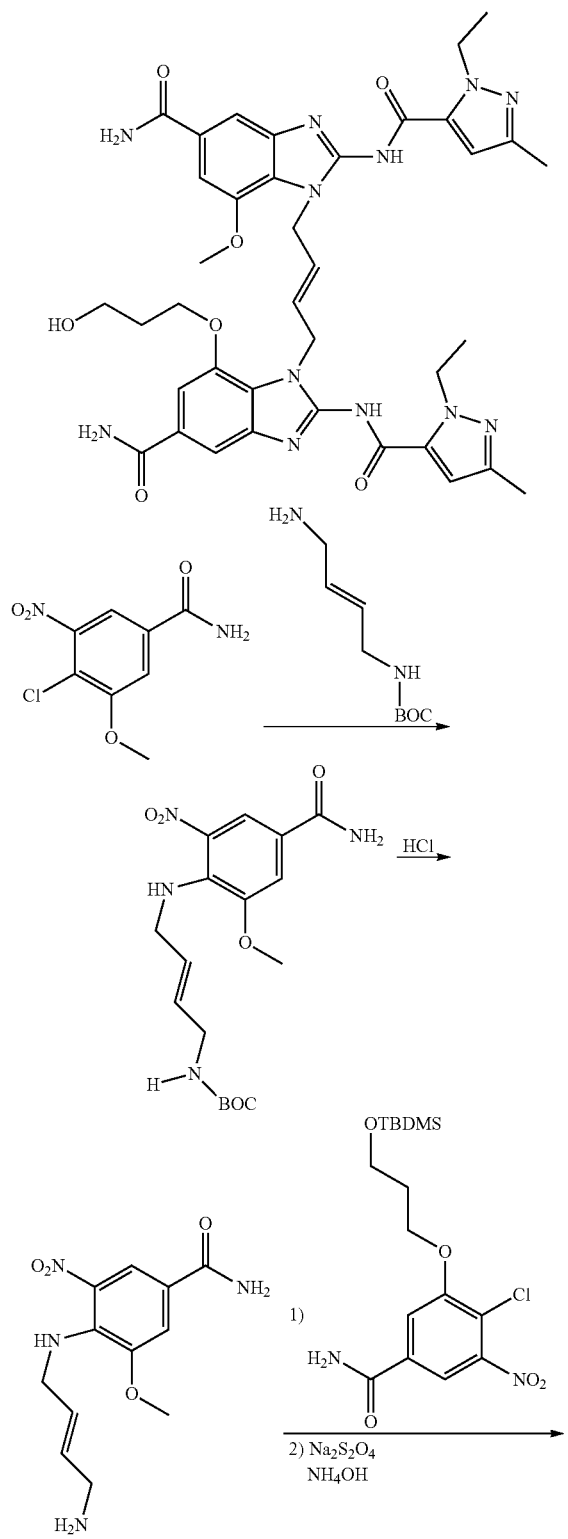
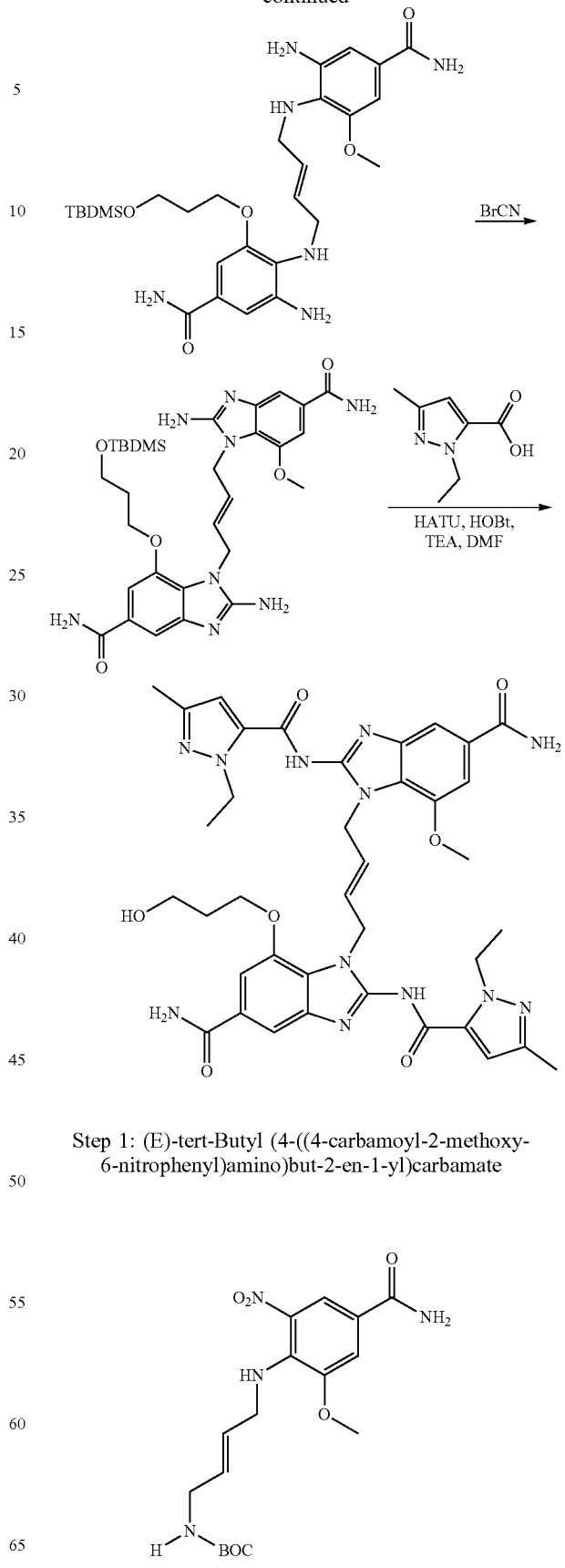
Step 1: (E)-tert-Butyl (4-((4-carbamoyl-2-methoxy-6-nitrophenyl)amino)but-2-en-1-yl)carbamate To suspension of (4-chloro-3-methoxy-5-nitrobenzamide (1.50 g, 6.50 mmol) in EtOH (25 mL) was added (E)-tert-butyl(4-aminobut-2-en-1-yl)carbamate (1.454 g, 7.81 mmol) and DIEA (3.4 mL, 20 mmol). The reaction was stirred at 120° C. in a sealed tube overnight and allowed to cool to RT. The resulting orange solid was collected by filtration 10 and washed with EtOH to afford the title compound (2.10 g, 5.52 mmol, 8500 yield). $^1$H NMR (400 MHz, DMSO-$d_6$) δ ppm 8.19 (d, J=1.77 Hz, 1H) 8.03 (br. s., 1H) 7.76 (t, J=6.08 Hz, 1H) 7.55 (d, J=1.52 Hz, 1H) 7.34 (br. s., 1H) 6.95 (t, J=5.45 Hz, 1H) 5.53 (br. s., 2H) 4.09 (br. s., 2H) 3.88 (s, 3H) 3.48 (br. s., 2H) 1.35 (s, 9H); LCMS (LCMS Method D): Rt=0.89 min, [M-t-Bu+H]$^+$=325.1

Step 2: (E)-4-((4-Aminobut-2-en-1-yl)amino)-3-methoxy-5-nitrobenzamide, hydrochloride

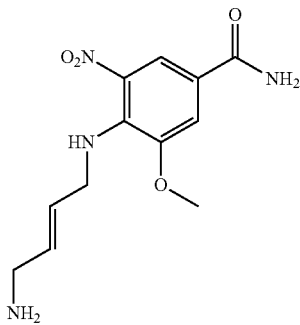 [SMILES: COc1cc(C(N)=O)cc([N+](=O)[O-])c1NC/C=C/CN]

To a suspension of tert-butyl (E)-(4-((4-carbamoyl-2-methoxy-6-nitrophenyl)amino)but-2-en-1-yl)carbamate (20 g, 47.3 mmol) in methanol (50 mL) was added slowly 4M HCl in dioxane (100 mL, 400 mmol). The reaction mixture was stirred at RT for 1hr, then the resulting solid was isolated by filtration, washed with Et$_2$O 3 times (100 ml×3), and dried under high vacuum column to provide the title compound (13.90 g, 43.9 mmol, 93% yield). $^1$H NMR (400 MHz, DMSO-$d_6$) δ ppm 8.22 (d, J=2.03 Hz, 1H), 7.76-8.16 (br. in., 5H), 7.60 (d, J=2.03 Hz, 1H), 7.37 (br. s., 1H), 5.87 (dt, J=15.52, 5.80 Hz, 1H), 5.62 (dt, J=15.65, 6.37 Hz, 1H), 4.18 (d, J=5.32 Hz, 2H), 3.90 (s, 3H), 3.40 (t, J=5.70 Hz, 2H); LCMS (LCMS Method K): Rt=0.41 min, [M+H]$^+$=281.1

Step 3: (E)-3-(3-((tert-Butyldimethylsilyl)oxy)propoxy)-4-((4-((4-carbamoyl-2-methoxy-6-nitrophenyl)amino)but-2-en-1-yl)amino)-5-nitrobenzamide

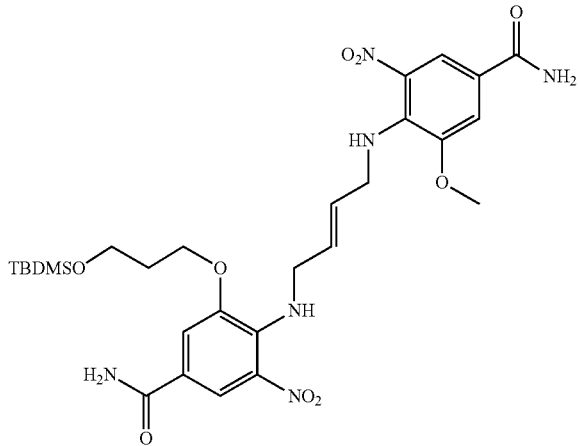 [SMILES: COc1cc(C(N)=O)cc([N+](=O)[O-])c1NC/C=C/CNc1c(OCCCO[Si](C)(C)C(C)(C)C)cc(C(N)=O)cc1[N+](=O)[O-]]

To a suspension of (E)-4-((4-aminobut-2-en-1-yl)amino)-3-methoxy-5-nitrobenzamide, hydrochloride (9.77 g, 30.9 mmol) in 1-Butanol (90 mL) was added sodium bicarbonate (5.18 g, 61.7 mmol) and DIEA (22.45 mL, 129 mmol). The mixture was stirred at RT for 10 min, then 3-(3-((tert-butyldimethylsilyl)oxy)propoxy)-4-chloro-5-nitrobenzamide (10 g, 25.7 mmol) was added and the reaction mixture was stirred at 120° C. overnight. The solution was allowed to cool to RT and the resulting dark orange solid was isolated by filtration and washed EtOH (15 ml). The crude material was then stirred in water (100 mL) for 10 min., filtered and washed again with water (100 mL), EtOAc (50 mL) and EtOH (20 mL). The material was dried in vacuum oven to provide the title compound (10 g, 14.54 mmol, 56.5% yield). $^1$H NMR (400 MHz, DMSO-$d_6$) δ ppm 8.16 (t, J=1.77 Hz, 2H), 8.04 (br. s., 2H), 7.72 (d, J=5.83 Hz, 2H), 7.53 (s, 2H), 7.35 (br. s., 2H), 5.53-5.68 (m, 2H), 3.99-4.16 (m, 6H), 3.74 (t, J=6.08 Hz, 2H), 3.43 (br. s., 3H), 1.92 (t, J=6.08 Hz, 2H), 0.74-0.88 (m, 9H), 0.00 (s, 6H); LCMS (LCMS Method K): Rt=1.32 min, [M+H]$^+$=633.4

Step 4: (E)-3-Amino-4-((4-((2-amino-4-carbamoyl-6-methoxyphenyl)amino)but-2-en-1-yl)amino)-5-(3-((tert-butyldimethylsilyl)oxy)propoxy)benzamide

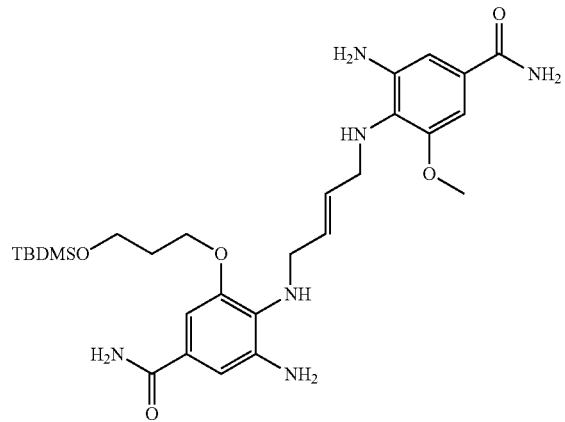 [SMILES: COc1cc(C(N)=O)cc(N)c1NC/C=C/CNc1c(N)cc(C(N)=O)cc1OCCCO[Si](C)(C)C(C)(C)C]

To a solution of (E)-3-(3-((tert-butyldimethylsilyl)oxy)propoxy)-4-((4-((4-carbamoyl-2-methoxy-6-nitrophenyl)amino)but-2-en-1-yl)amino)-5-nitrobenzamide (5 g, 7.90 mmol) in methanol (120 mL) at 0° C., was added sodium hydrosulfite (16.19 g, 79 mmol) in water (50 mL) and ammonium hydroxide (25.6 mL, 198 mmol). The reaction mixture was allowed to warm to RT. After 10 min. at RT, the mixture was extracted with EtOAc (100×3), dried over Na$_2$SO$_4$, and concentrated in vacuo. The crude material was purified by silica gel chromatography (Isco column) eluting with hexane: (EtOH: EtOAc 3:1) with 2% NH$_4$OH additive (0-100% gradient) to yield the title compound (2.1 g, 3.34 mmol, 42.2% yield). $^1$H NMR (400 MHz, DMSO-$d_6$) δ ppm 7.63 (br. s., 2H), 6.99 (d, J=5.58 Hz, 2 H), 6.72-6.91 (m, 6H), 5.62-5.73 (m, 2H), 4.66 (d, J=8.36 Hz, 4H), 4.00 (t, J=5.96 Hz, 2H), 3.69-3.84 (m, 4H), 3.40-3.49 (m, 2H), 3.35 (s, 3H), 1.90 (t, J=6.08 Hz, 2H), 0.79-0.91 (m, 9H), −0.03-0.07 (m, 6H); LCMS (LCMS Method K): Rt=0.46 min, [M+H]$^+$=573.3

Step 5: (E)-1-(4-(5-Carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide

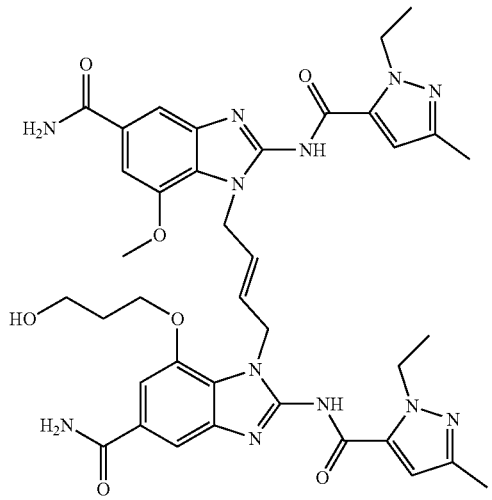 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCO)c21]

To a solution of (E)-3-amino-4-((4-((2-amino-4-carbamoyl-6-methoxyphenyl)amino)but-2-en-1-yl)amino)-5-(3-((tert-butyldimethylsilyl)oxy)propoxy)benzamide (1.02 g, 1.78 mmol) in MeOH (15 mL) was added cyanogen bromide (943 mg, 8.90 mmol). After stirring at room temperature for 20 min, alight yellow solid precipitated, which was collected by filtration, washed with EtOAc and determined by LCMS to be a mixture of ⅔ of the TBDMS-protected compound (E)-2-amino-1-(4-(2-amino-5-carbamoyl-7-methoxy-1H-benzo[d]imidazol-1-yl)but-2-en-1-yl)-7-(3-((tert-butyldimethylsilyl)oxy)propoxy)-1H-benzo[d]imidazole-5-carboxamide and ⅓ deprotected alcohol (E)-2-amino-1-(4-(2-amino-5-carbamoyl-7-(3-hydroxypropoxy)-1H-benzo[d]imidazol-1-yl)but-2-en-1-yl)-7-methoxy-1H-benzo[d]imidazole-5-carboxamide. This mixture (ca. 900 mg) was added, after TEA (1.07 mL, 7.7 mmol), to a solution of 1-ethyl-3-methyl-1H-pyrazole-5-carboxylic acid (0.89 g, 5.78 mmol), HATU (2.2 g, 5.78 mmol) and HOBt (443 mg, 2.89 mmol) in DMF (10 mL) which had been stirred for 15 min at RT. After 20 hr, 5N aq NaOH (3 mL) was added. After 30 min at RT, water (30 mL) was added, and the resulting white precipitate was collected by filtration and purified over silica gel (40 g Isco column), eluting with 0-30% MeOH in DCM to yield the title compound (545 mg, 0.684 mmol, 38% yield for 2 steps). $^1$H NMR (400 MHz, DMSO-d) δ ppm 12.83 (br. s., 2H), 7.99 (br. s., 2H), 7.64 (d, J=3.04 Hz, 2H), 7.28-7.42 (m, 4H), 6.52 (s, 2H), 5.84 (br. s., 2H), 4.91 (br. s., 4H), 4.53 (d, J=6.34 Hz, 4H), 4.06 (t, J=6.34 Hz, 2H), 3.75 (s, 3H), 3.45 (t, J=5.96 Hz, 2H), 2.10 (d, J=2.53 Hz, 6H), 1.71 (t, J=6.08 Hz, 2H), 1.27 (td, J=7.03, 1.90 Hz, 6H); LCMS (LCMS Method D): Rt=0.85 min, [M/2+H]$^+$=391.3833

The compound prepared by the above process may exist in a tautomeric or an isomeric form, e.g., as (E)-1-((E)-4-((E)-5-carbamoyl-2-((1-ethyl-3-methyl-1H-pyrazole-5-carbonyl)imino)-7-(3-hydroxypropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide

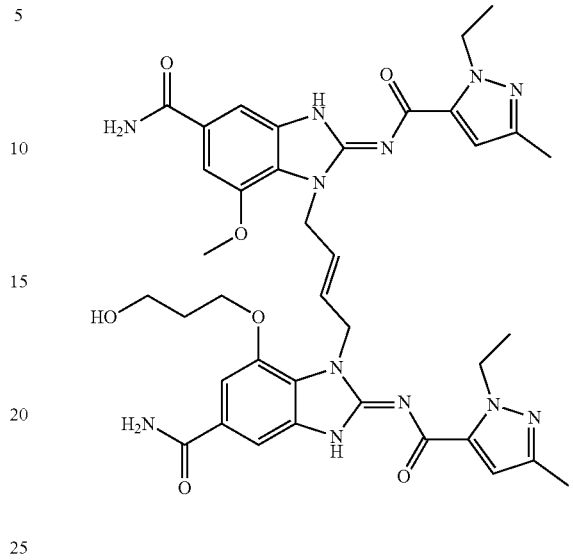

or (Z)-1-((E)-4-((Z)-5-carbamoyl-2-((1-ethyl-3-methyl-1H-pyrazole-5-carbonyl)imino)-7-(3-hydroxypropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide

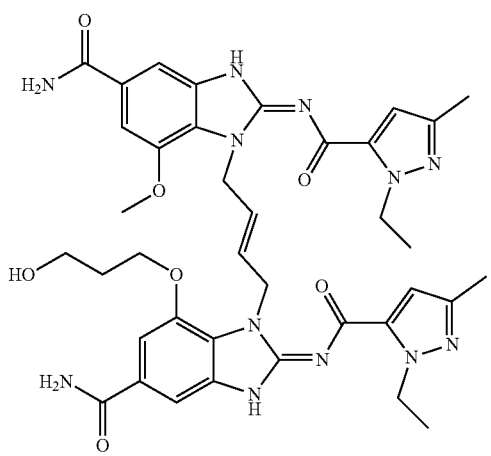 [SMILES: CCn1nc(C)cc1C(=O)/N=c1/[nH]c2cc(C(N)=O)cc(OC)c2n1C/C=C/Cn1/c(=N\C(=O)c2cc(C)nn2CC)[nH]c2cc(C(N)=O)cc(OCCCO)c21]

Example 3

(E)-1-(4-(5-Carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-morpholinopropoxy)-1H-benzo[d]imidazole-5-carboxamide

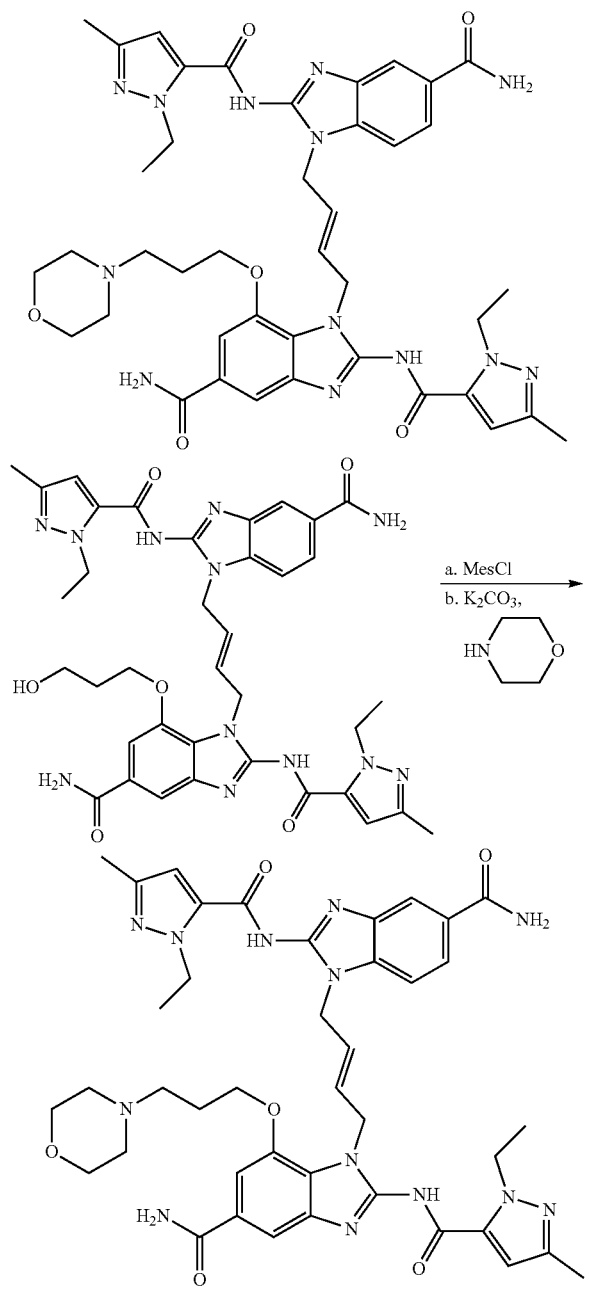

Step 1: To (E)-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-7-(3-hydroxy-propoxy)-1H-benzo[d]imidazole-5-carboxamide (17 mg, 0.023 mmol) in THF (3 mL) was added triethylamine (9.5 L, 0.068 mmol). After 10 min at RT, methanesulfonyl chloride (2.1 L, 0.027 mmol) was added. After 2 hr, LCMS indicated presence of (E)-3-((5-Carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl methanesulfonate, and the reaction mixture was used directly in the next reaction. LCMS (LCMS Method D): Rt=0.80 min, [M+H]$^+$=751.6010.

Step 2: To a solution of (E)-3-((5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1Hpyrazole-5-carboxamido)-1H-benzo[d]imidazol-7-yl)oxy)propyl methanesulfonate (18 mg, 0.022 mmol) in THF (5 mL) was added morpholine (9.5 L, 0.11 mmol) and $K_2CO_3$ (9.0 mg, 0.065 mmol). After 5 hr at RT, the reaction was heated to 45° C. for 2 hr and then concentrated. The residue was purified over silica gel eluting with 0-20% MeOH in DCM to yield the title compound (7 mg, 9 μmole, 39% yield). $^1$H NMR (400 MHz, MeOH-$d_4$) δ ppm 7.99 (d, J=1.27 Hz, 1H), 7.73 (dd, J=8.36, 1.52 Hz, 1H), 7.59 (d, J=1.27 Hz, 1H), 7.36 (d, J=8.62 Hz, 1H), 7.28 (d, J=1.27 Hz, 1H), 6.64 (s, 1H), 6.57 (s, 1H), 5.92-6.05 (m, 1H), 5.73-5.88 (m, 1H), 4.51-4.71 (m, 4H), 4.00 (t, J=6.21 Hz, 2H), 3.56-3.67 (m, 8H), 2.27-2.46 (m, 6H), 2.22 (d, J=10.39 Hz, 6H), 1.83 (dt, J=14.19, 6.84 Hz, 2H), 1.26-1.44 (m, 6H); LCMS (LCMS Method D): Rt=0.73 min, [M/2+H]$^+$=410.9876

The compound prepared by the above process may exist in a tautomeric or an isomeric form, e.g., as (E)-1-((E)-4-((E)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide

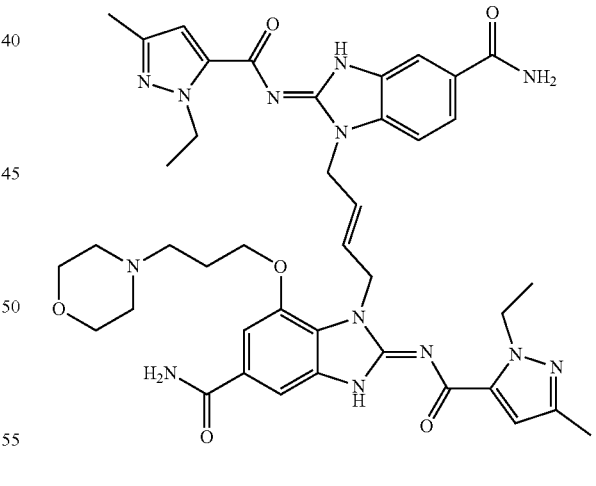

or (Z)-1-((E)-4-((Z)-5-carbamoyl-2-((1-ethyl-3-methyl-1H-pyrazole-5-carbonyl)imino)-2,3-dihydro-1H-benzo[d]imidazol-1-yl)but-2-en-1-yl)-2-((1-ethyl-3-methyl-1H-pyrazole-5-carbonyl)imino)-7-(3-morpholinopropoxy)-2,3-dihydro-1H-benzo[d]imidazole-5-carboxamide 73
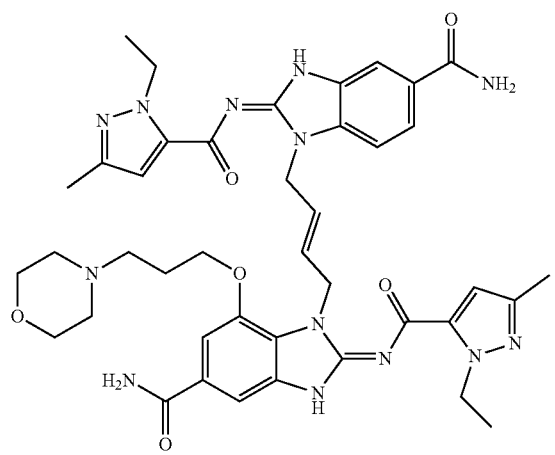 [SMILES: CCn1nc(C)cc1C(=O)/N=c1/[nH]c2cc(C(N)=O)ccc2n1C/C=C/Cn1/c(=N\C(=O)c2cc(C)nn2CC)[nH]c2cc(C(N)=O)cc(OCCCN3CCOCC3)c21]
Example 4
(E)-1-(4-(5-Carbamoyl-2-(1-ethyl-3-methyl-1H-pyrazole-5-carboxamido)-7-(3-morpholinopropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide tris hydrochloride
Compound 1
74
-continued
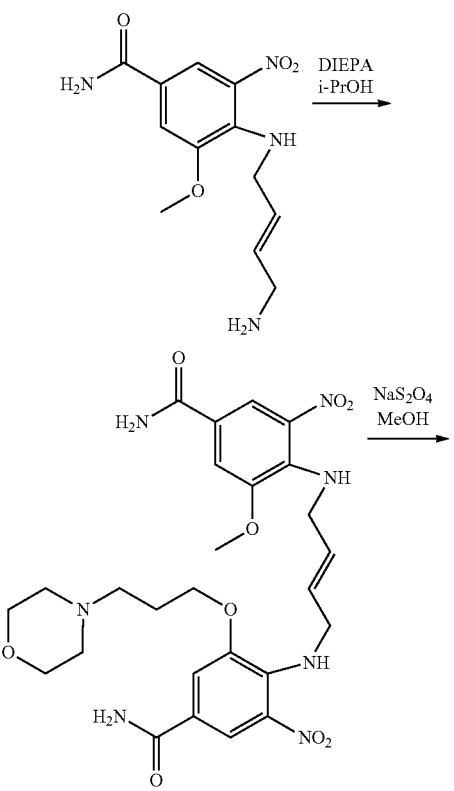
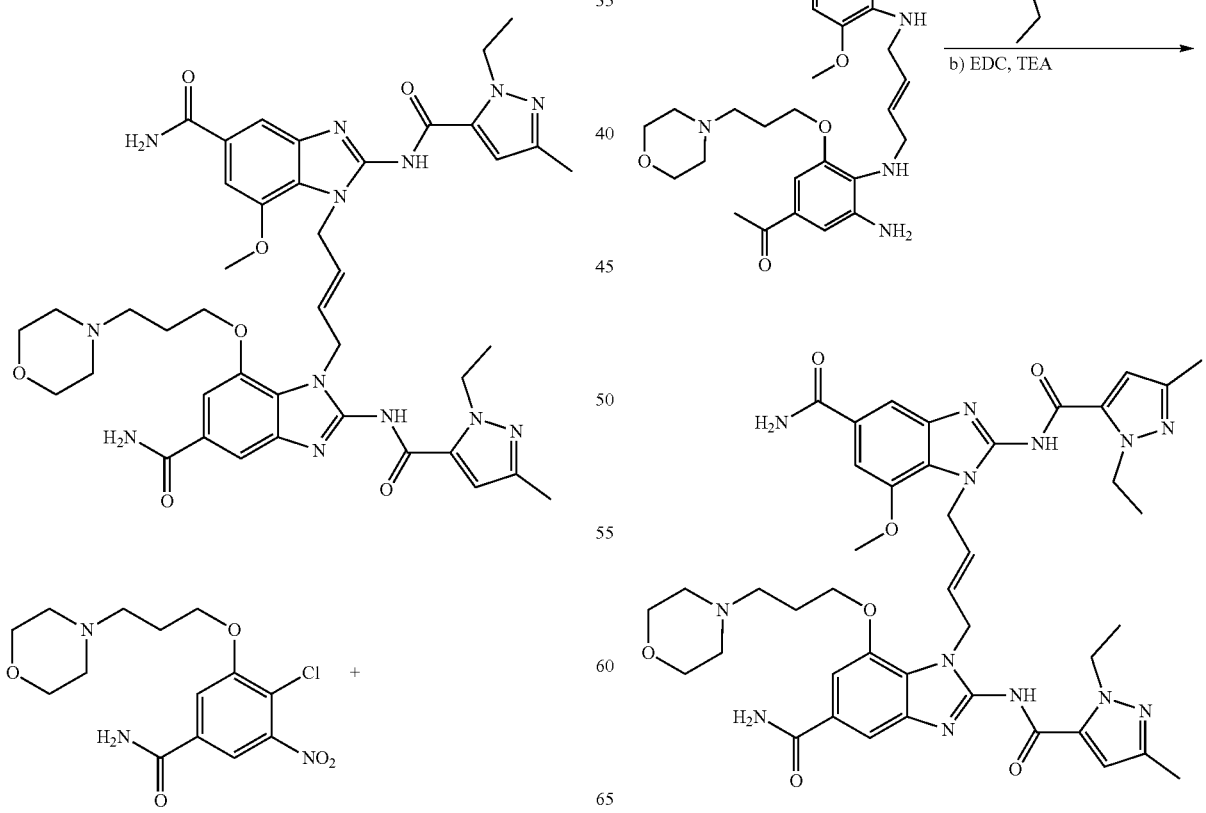

Step 1: (E)-4-((4-((4-Carbamoyl-2-(3-morpholino-propoxy)-6-nitrophenyl)amino)but-2-en-1-yl)amino)-3-methoxy-5-nitrobenzamide

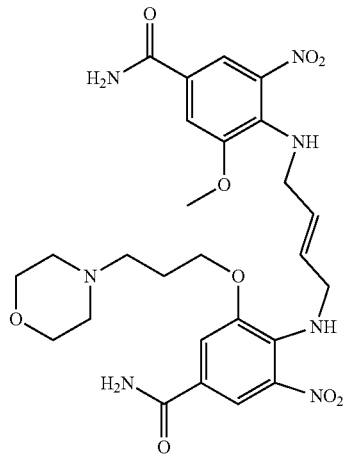

(E)-4-((4-aminobut-2-en-1-yl)amino)-3-methoxy-5-nitrobenzamide, hydrochloride (1.7 g, 5.37 mmol), 4-chloro-3-(3-morpholinopropoxy)-5-nitrobenzamide (1.655 g, 4.81 mmol) i-PrOH (15 ml) and DIPEA (2.94 ml, 16.85 mmol) were divided into two 24 mL vials, then the vials were capped heated to 120° C. for 42 hrs. The solid was isolated by filtration, rinsed with i-PrOH (2×3 mL) to afford (E)-4-((4-((4-carbamoyl-2-(3-morpholinopropoxy)-6-nitrophenyl)amino)but-2-en-1-yl)amino)-3-methoxy-5-nitrobenzamide (1.95 g, 2.79 mmol, 51.9% yield) as a brick red solid. LCMS (LCMS Method K): Rt=0.60 min, [M+H]+=588.2

Step 2: (E)-3-Amino-4-((4-((2-amino-4-carbamoyl-6-(3-morpholinopropoxy)phenyl)amino)but-2-en-1-yl)amino)-5-methoxybenzamide

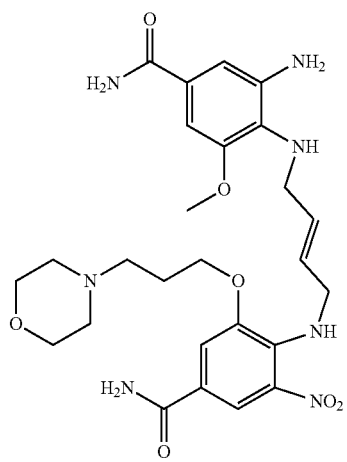 [SMILES: COc1cc(C(N)=O)cc([N+](=O)[O-])c1NC/C=C/CNc1c(OCCCN2CCOCC2)cc(C(N)=O)cc1[N+](=O)[O-]]

To (E)-4-((4-((4-carbamoyl-2-(3-morpholinopropoxy)-6-nitrophenyl)amino)but-2-en-1-yl)amino)-3-methoxy-5-nitrobenzamide (4.6 g, 6.65 mmol) in MeOH (83.0 mL) at RT was added sodium hydrosulfite (19.08 g, 93.0 mmol) in water (70 mL). After 15 min, solid sodium bicarbonate (24 grams) was added. After 10 min., the reaction was filtered, and the solid was rinsed with MeOH (4×20 mL). The combined filtrates were concentrated onto Celite, and the was purified by dry-loading onto silica gel (80 g Gold column), eluting with 2-40% (10:1 MeOH: aq NH4OH) in DCM to afford the title compound (1.81 g, 3.26 mmol, 49% yield) as a dark yellow film. $^1$H NMR (400 MHz, DMSO-d$_6$) δ ppm 7.64 (br. s., 2H), 6.99 (br. s., 2H), 6.85 (dd, J=5.07, 1.77 Hz, 2H), 6.78 (dd, J=4.31, 1.77 Hz, 2H), 5.63-5.72 (m, 2H), 4.66 (d, J=8.11 Hz, 4H), 3.96 (t, J=6.21 Hz, 2H), 3.74 (s, 3H), 3.51-3.60 (m, 6H), 3.17 (br. s., 4H), 2.43 (t, J=7.10 Hz, 2H), 2.35 (br. s., 4H), 1.87 (t, J=6.72 Hz, 2H); LCMS (LCMS Method K): Rt=0.37 min, [M+H]+=528.4

Step 3: (E)-1-(4-(5-Carbamoyl-2-(1-ethyl-3-methyl-1H-pyrazole-5-carboxamido)-7-(3-morpholino-propoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide tris hydrochloride

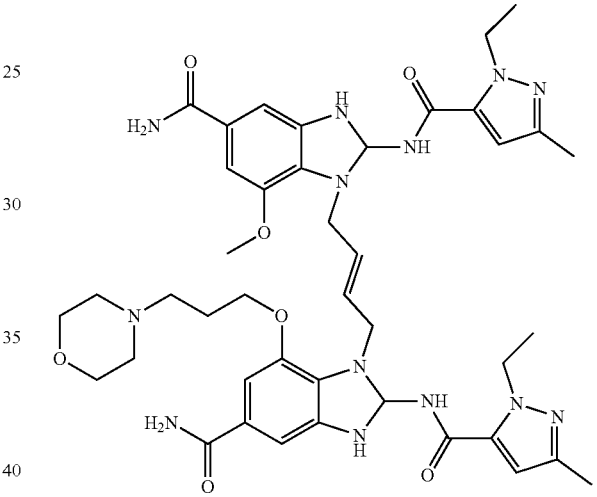

To (E)-3-amino-4-((4-((2-amino-4-carbamoyl-6-(3-morpholinopropoxy)phenyl)amino)-but-2-en-1-yl)amino)-5-methoxybenzamide (368 mg, 0.697 mmol) in DMF (6.97 mL) at 0° C. was added 0.4 M 1-ethyl-3-methyl-H-pyrazole-5-carbonyl isothiocyanate in dioxane (2.0 mL, 0.80 mmol). After 10 min, another portion of 0.4 M 1-ethyl-3-methyl-1H-pyrazole-5-carbonyl isothiocyanate in dioxane (0.5 mL, 0.20 mmol) was added, followed 15 min later by a final portion (0.5 mL, 0.20 mmol). After 35 min total reaction time, EDC (334 mg, 1.74 mmol) was added followed by triethylamine (0.486 mL, 3.49 mmol). The mixture was allowed to warm to RT and stirred overnight (14 hours). The reaction was quenched with 3:1 water: saturated aqueous NH4Cl solution (40 mL) and extracted with 3:1 chloroform: ethanol (2×40 mL). The combined organic phases were washed with water (20 mL), dried over MgSO4 and concentrated. The resulting residue was purified over silica gel (40 g Gold column), eluting with 2-40% (10:1 MeOH: aq NH4OH) in DCM to give pure material as the free base. This product was partially dissolved in MeOH and treated with 4M HCl in dioxane (0.35 mL, 1.40 mmol), then concentrated. The residue was taken up in MeCN-water and lyophilized to yield the title compound (403.6 mg, 0.421 mmol, 60% yield) as an off-white solid. $^1$H NMR (400 MHz, methanol-d$_4$) δ 7.70 (dd, J=2.66, 1.14 Hz, 2H), 7.42 (d, J=1.27 Hz, 2H), 6.72 (d, J=3.04 Hz, 2H), 5.79-6.12 (m, 2H), 5.19 (dd, J=11.03, 5.45 Hz, 4H), 4.61-4.81 (m, 4H), 4.00-4.25 (m, 4H), 3.79-3.96 (m, 5H), 3.45 (d, J=12.42 Hz, 2H), 3.28-3.36 (m, 2H), 3.14 (td, J=12.23, 3.68 Hz, 2H), 2.28 (s, 6H), 2.07-2.25 (m, 2H), 1.46 (td, J=7.10, 3.80 Hz, 6H); LCMS (LCMS Method K): Rt=0.68 min, [M+H]⁺=850.6. The compound prepared by the above process may exist in a tautomeric or an isomeric form, e.g., as (E)-1-((E)-4-((E)-5-carbamoyl-2-((1-ethyl-3-methyl-1H-pyrazole-5-carbonyl)imino)-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide tris hydrochloride

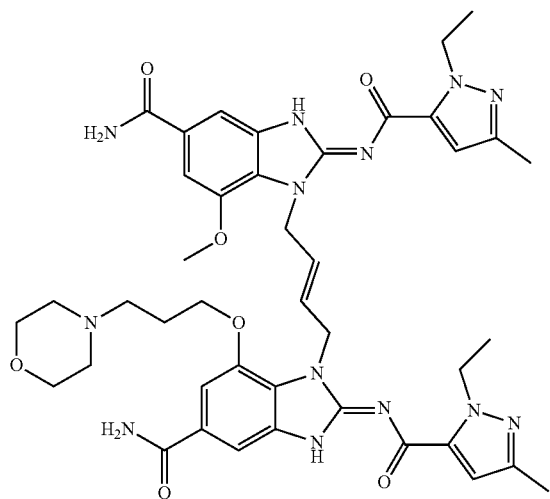 [SMILES: CCn1nc(C)cc1C(=O)/N=c1\[nH]c2cc(C(N)=O)cc(OC)c2n1C/C=C/Cn1/c(=N/C(=O)c2cc(C)nn2CC)[nH]c2cc(C(N)=O)cc(OCCCN3CCOCC3)c21]

or (Z)-1-((E)-4-((Z)-5-carbamoyl-2-((1-ethyl-3-methyl-1H-pyrazole-5-carbonyl)imino)-7-(3-morpholinopropoxy)-2,3-dihydro-1H-benzo[d]imidazol-1-yl)but-2-en-1-yl)-2-((1-ethyl-3-methyl-1H-pyrazole-5-carbonyl)imino)-7-methoxy-2,3-dihydro-1H-benzo[d]imidazole-5-carboxamide tris hydrochloride

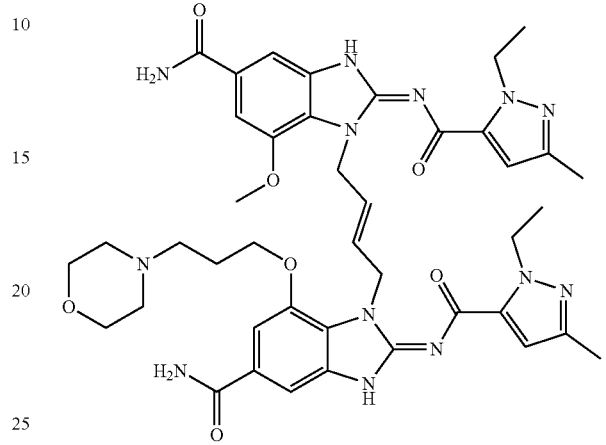

Example 5

Di-tert-butyl(3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyl)phosphate

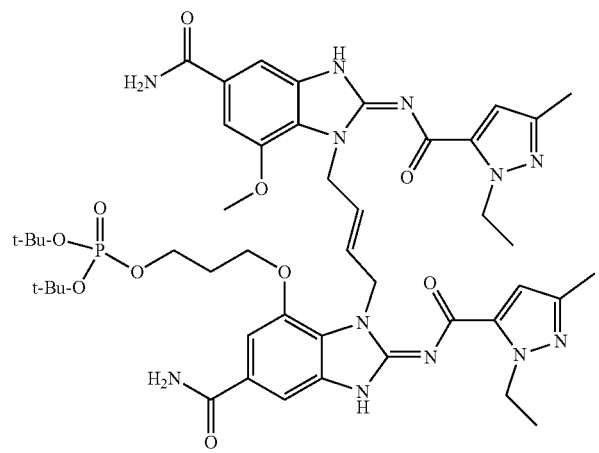

-continued
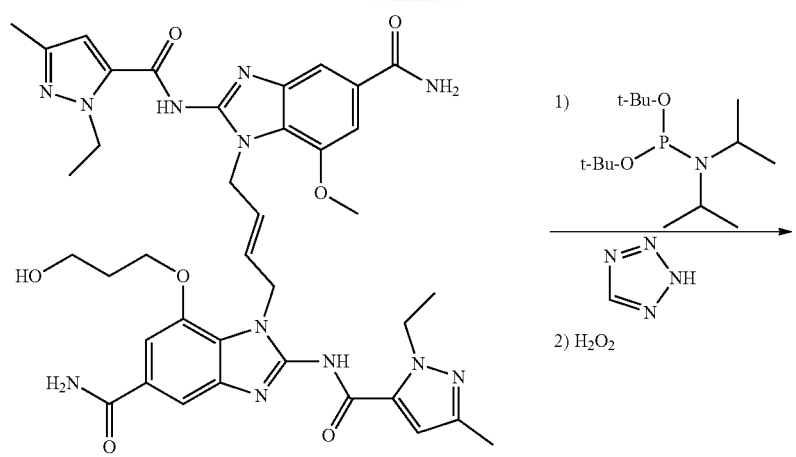
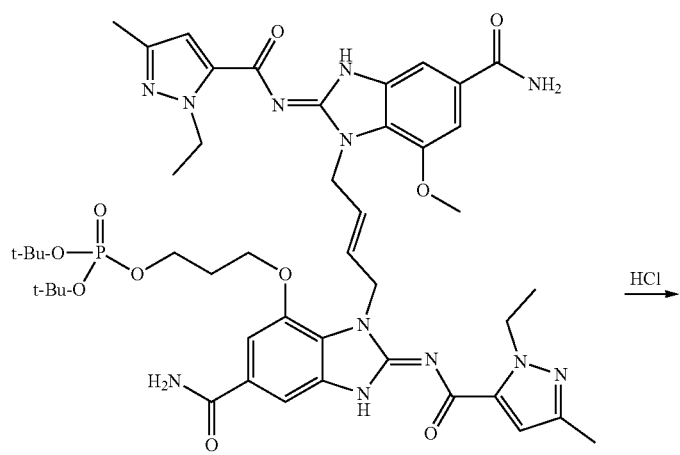
Example 18
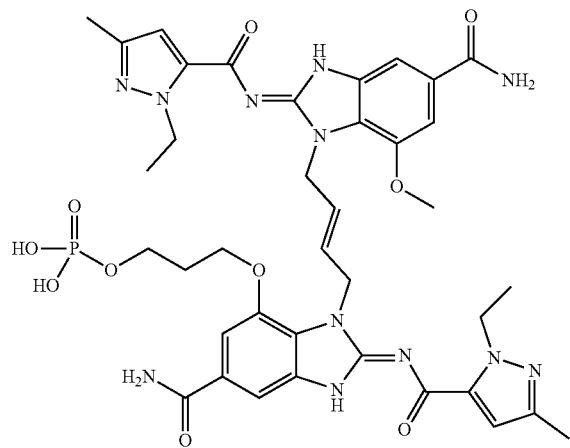
Example 19

Di-tert-butyl (3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyl) phosphate

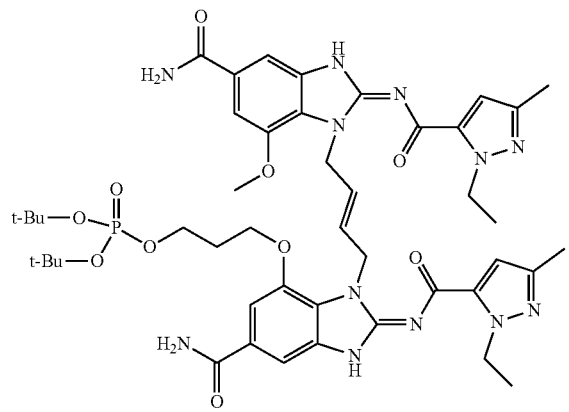 [SMILES: CCn1nc(C)cc1C(=O)/N=c1/[nH]c2cc(C(N)=O)cc(OC)c2n1C/C=C/Cn1/c(=N\C(=O)c2cc(C)nn2CC)[nH]c2cc(C(N)=O)cc(OCCCOP(=O)(OC(C)(C)C)OC(C)(C)C)c21]

A suspension of (E)-1-(4-(5-carbamoyl-2-(1-ethyl-3-methyl-H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide (1.00 g, 1.28 mmol) and 0.45 M 2H-tetrazole in acetonitrile (14.2 mL, 6.40 mmol) in DMF (5 mL) was concentrated on a rotary evaporator to remove acetonitrile. The resulting heterogeneous mixture in DMF was cooled to 0° C. then a solution of di-tert-butyl diisopropylphosphoramidite (1.617 mL, 5.12 mmol) in 5 mL DMF was added. Soon after addition, the solution becomes homogeneous but again becomes heterogeneous as the reaction is stirred at RT for 2 additional hours. The temperature was lowered to 0° C. and $H_2O_2$ (30% Wt in water, 2.62 mL, 25.6 mmol) was added. After stirring for 20 min, an additional 10 eq of $H_2O_2$ was added and the reaction stirred until homogeneous (30 min). A 2 mL portion of aqueous $NaHCO_3$ and $Na_2S_2O_3$ (0.4M in $NaHCO_3$, 2M in $Na_2S_2O_3$) was added to 200 mL water. When the reaction mixture was poured into this solution, a precipitate was formed. The precipitate was then collected on a filter, dissolved in 200 mL THF, dried with $MgSO_4$ and concentrated to provide the title compound as an off-white solid (1.1 g, 1.13 mmol, 88% yield). $^1$H NMR (400 MHz, DMSO-$d_6$) δ ppm 12.8 (s, 2H), 10.2 (s, 1H), 7.98 (m, 2H), 7.65 (d, J=2.5 Hz, 2H), 7.34 (m, 4H), 6.51 (d, J=2.5 Hz, 2H), 5.83 (m, 2H), 4.91 (m, 4H), 4.52 (m, 4H), 4.09 (m, 2H), 3.93 (m, 2H), 3.74 (s, 3H), 3.60 (m, 2H), 2.11 (s, 6H), 1.90 (m, 2H), 1.76 (m, 2H), 1.4-1.3 (m, 18H, 1.27 (m, 6H); LCMS (LCMS Method I): Rt=1.09 min, [M+H]$^+$=973.3.

Example 6

3-(((Z)-6-Carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyl dihydrogen phosphate

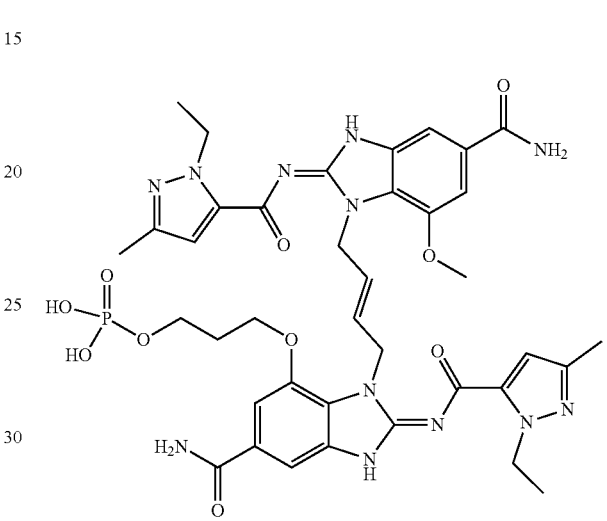

To di-tert-butyl(3-(((Z)-6-carbamoyl-3-((E)-4-((Z)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)-propyl) phosphate (18 mg, 0.018 mmol) suspended in dioxane (1 mL) at RT was added 4N HCl in dioxane (0.028 mL, 0.11 mmol). Some precipitate formed immediately. The reaction was stirred for 2 hr and additional 4N HCl in dioxane (0.028 mL, 0.11 mmol) was added. After 2 hr, the reaction was placed in freezer, and after 16 hr, the reaction was diluted with diethyl ether. The mixture was adjusted to pH of 23 with conc. ammonium hydroxide. The precipitate was collected by filtration and washed with ether to yield the title compound (15 mg, 0.017 mmol, 92% yield) as a white solid. $^1$H NMR (600 MHz, DMSO-$d_6$) δ ppm 12.85 (br s, 1H), 8.02 (br, d, J=6.6 Hz, 2H), 7.65 (d, J=5.7 Hz, 2H), 7.35-7.41 (m, 2H), 7.34 (br. d, J=10.6 Hz, 2H), 6.51 (d, J=12.8 Hz, 2H), 5.74-5.89 (m, 2H), 4.92 (br. dd, J=12.0, 4.9 Hz, 4H), 4.50 (quin, J=7.0 Hz, 4H), 4.10 (br. t, J=6.1 Hz, 2H), 3.91-3.94 (m, 2H), 3.75 (s, 3H), 2.10 (d, J=3.1 Hz, 6H), 1.84-1.93 (m, 2H), 1.22-1.28 (m, 6H); LCMS (LCMS Method I): Rt=0.68 min, [M+H]$^+$=861.2

The compound prepared by the above process may exist in a tautomeric or an isomeric form, e.g., as (E)-3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl dihydrogen phosphate

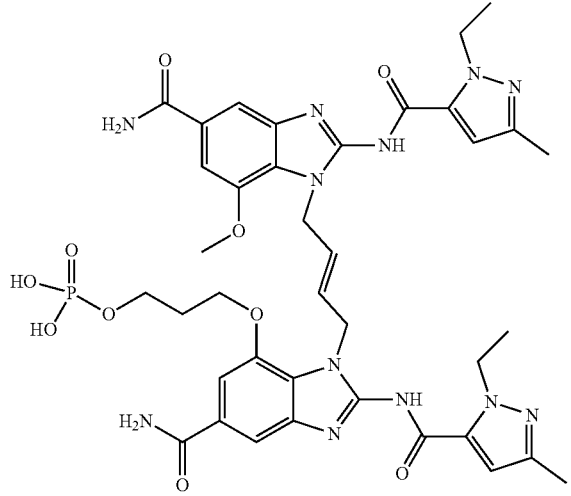 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCOP(=O)(O)O)c21]

or 3-(((E)-6-carbamoyl-3-((E)-4-((E)-5-carbamoyl-2-((1-ethyl-3-methyl-1H-pyrazole-5-carbonyl)imino)-7-methoxy-2,3-dihydro-1H-benzo[d]imidazol-1-yl)but-2-en-1-yl)-2-((1-ethyl-3-methyl-1H-pyrazole-5-carbonyl)imino)-2,3-dihydro-1H-benzo[d]imidazol-4-yl)oxy)propyl dihydrogen phosphate

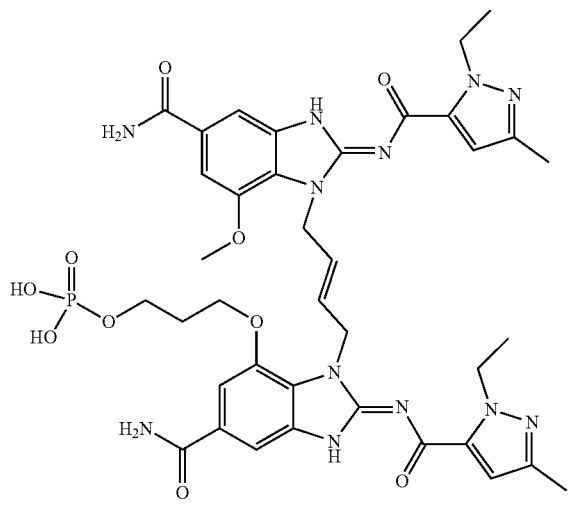 [SMILES: CCn1nc(C)cc1C(=O)/N=c1\[nH]c2cc(C(N)=O)cc(OC)c2n1C/C=C/Cn1/c(=N/C(=O)c2cc(C)nn2CC)[nH]c2cc(C(N)=O)cc(OCCCOP(=O)(O)O)c21]

Example 7

(E)-3-(5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)propanoic acid

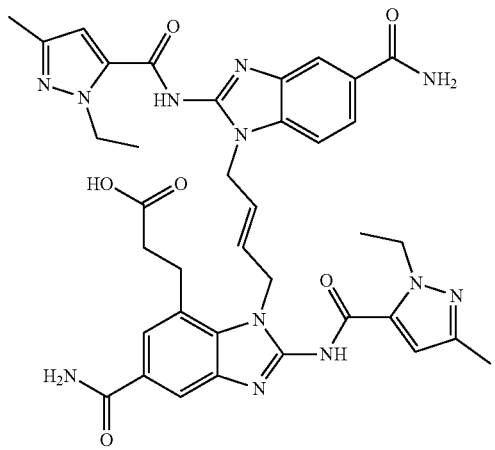

Step 1: ethyl 3-(5-carbamoyl-2-fluoro-3-nitrophenyl)propanoate

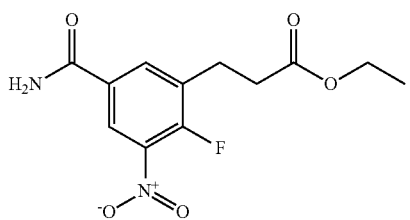

To 3-bromo-4-fluoro-5-nitrobenzamide (1 g, 3.65 mmol) in DMF (12.17 ml) were added tetra-n-butylammonium chloride (1.035 g, 3.65 mmol), Pd(OAc)$_2$ (0.084 g, 0.365 mmol). After flushing with nitrogen for 10 min, 3,3-diethoxyprop-1-ene (1.739 ml, 10.95 mmol), and tributylamine (1.766 mL, 7.30 mmol) were added. The 20-mL microwave vessel was sealed and heated at 125° C. for 6 h. The reaction products were partitioned between EtOAc (50 mL) and a mix of saturated NH$_4$Cl/brine (50 mL). The aqueous layer was twice extracted with EtOAc (20 mL). The combined EtOAc layer was dried over magnesium sulfate, filtered, and concentrated. The residue was then purified by silica gel chromatography (Isco Combiflash Lumen, 12 g column, gradient of 45-100% EtOAc/hexanes) to yield ethyl 3-(5-carbamoyl-2-fluoro-3-nitrophenyl)propanoate (360 mg, 1.267 mmol, 34.7% yield). LCMS (m/z): 285.1 [M+H]+.

Step 2: ethyl (E)-3-(5-carbamoyl-2-((4-((4-carbamoyl-2-nitrophenyl)amino)but-2-en-1-yl)amino)-3-nitrophenyl)propanoate

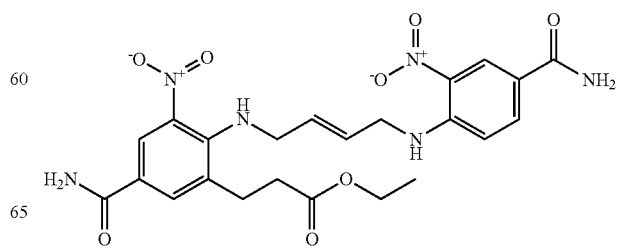

To (E)-4-((4-aminobut-2-en-1-yl)amino)-3-nitrobenzamide, 2Hydrochloride (for example prepared as Intermediate 6) (0.317 g, 0.960 mmol) in DMF (3 mL) was added triethylamine (0.402 mL, 2.88 mmol) and a solution of ethyl 3-(5-carbamoyl-2-fluoro-3-nitrophenyl)propanoate (0.350 g, 0.960 mmol) in DMF (1 ml). The reaction was stirred at room temperature for 6 h then 50° C. for 48 h. The reaction products were partitioned between EtOAc (40 mL) and aqueous $NH_4C_1$ solution. The aqueous phase was extracted once with EtOAc then the combined organic phase was washed with brine, dried over magnesium sulfate, filtered, and concentrated. The resulting orange oil was purified by silica gel chromatography (Isco Combiflash, 40 g column, gradient of 40-100% 3:1 EtOAc:EtOH/hexanes) to give ethyl (E)-3-(5-carbamoyl-2-((4-((4-carbamoyl-2-nitrophenyl)amino)but-2-en-1-yl)amino)-3-nitrophenyl)propanoate (358 mg, 0.696 mmol, 72.4% yield). LCMS (m/z): 515.2 [M+H]+.

Step 3: ethyl (E)-3-(3-amino-2-((4-((2-amino-4-carbamoylphenyl)amino)but-2-en-1-yl)amino)-5-carbamoylphenyl)propanoate

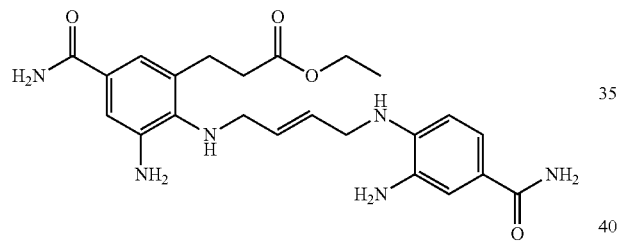

Ethyl (E)-3-(5-carbamoyl-2-((4-((4-carbamoyl-2-nitrophenyl)amino)but-2-en-1-yl)amino)-3-nitrophenyl)propanoate (330 mg, 0.641 mmol) was suspended in MeOH (9.33 mL) and 28% ammonium hydroxide solution (2.18 mL, 16.04 mmol) was added and stirred for 5 min. Sodium hydrosulfite (788 mg, 3.85 mmol) in water (2.33 mL) was added and stirred for 10 min. Owing to incomplete reduction, more sodium hydrosulfite (788 mg, 3.85 mmol) in water (2.33 mL) then MeOH (3 mL) were added. The color of the suspension changed from orange to light yellow and the mixture was stirred at room temperature for an additional 60 min. To the mixture was added EtOAc (50 mL) and water (50 mL). The organic phase was separated, dried with sodium sulfate, filtered, and concentrated to provide crude product as a yellow solid. The crude material was purified via silica gel chromatography (Isco CombiFlash Rf, 24 g column, gradient 30-100% 3:1 EtOAc:EtOH/hexanes). Pure fractions were collected and concentrated in vacuo to provide the title compound (79 mg, 0.174 mmol, 27% yield) as a white solid. LCMS (m/z): 455.2 [M+H]+.

Step 4: ethyl (E)-3-(5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)propanoate

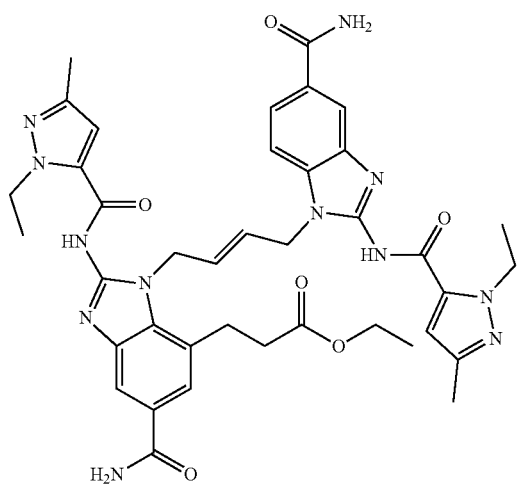 [SMILES: CCOC(=O)CCc1cc(C(N)=O)cc2nc(NC(=O)c3cc(C)nn3CC)n(C/C=C/Cn3c(NC(=O)c4cc(C)nn4CC)nc4cc(C(N)=O)ccc43)c12]

To a solution of ethyl (E)-3-(3-amino-2-((4-((2-amino-4-carbamoylphenyl)amino)but-2-en-1-yl)amino)-5-carbamoylphenyl)propanoate (79 mg, 0.174 mmol) in DMF (1738 µL) at 0° C. was added in 2 portions 1-ethyl-3-methyl-H-pyrazole-5-carbonyl isothiocyanate (for example as prepared in Intermediate 11) (869 µL, 0.348 mmol, 0.4 M in dioxane). The reaction was stirred for 1 h before EDC (100 mg, 0.521 mmol) and TEA (121 µL, 0.869 mmol) were added. The reaction was stirred at 50° C. for 18 h. When cool, the reaction was poured into 10% $NH_4C_1$ solution. The resulting precipitate was collected on a filter and washed with water to provide the title compound (85 mg, 0.109 mmol, 63% yield). LCMS (m/z): 777.5 [M+H]+.

Step 5: (E)-3-(5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)propanoic acid

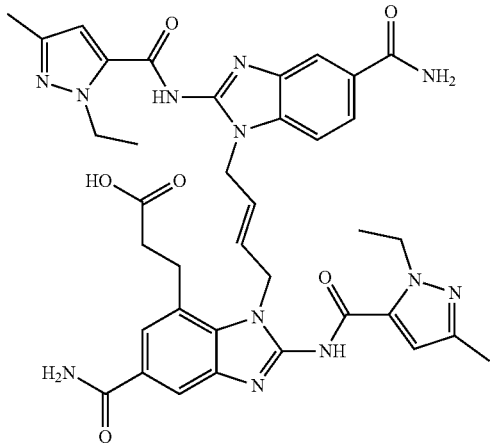

To a suspension of ethyl (E)-3-(5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)propanoate (80 mg, 0.103 mmol) in THF (1716 μL) and Water (1716 μL) was added LiOH (49.3 mg, 2.060 mmol) at 25° C. The mixture became homogeneous and was stirred for 60 min. THF was evaporated to provide a thick suspension. The suspension was acidified with 5 N HCl and filtered. The cake was washed 3× with water and dried in a vacuum oven for 2 h to give the title compound (56 mg, 0.075 mmol, 72.6% yield) as a light tan solid. $^1$H NMR (400 MHz, DMSO-$d_6$) δ ppm 12.05-13.83 (br. s., 1H), 7.94-8.00 (m, 2H), 7.88 (s, 1H), 7.73 (d, J=8.2 Hz, 1H), 7.59 (s, 1H), 7.43 (d, J=8.2 Hz, 1H), 7.35 (d, J=7.4 Hz, 1H), 6.55 (s, 1H), 6.51 (s, 1H), 5.95-6.04 (m, 1H), 5.51-5.60 (m, 1H), 5.02 (br. s., 2H), 4.84 (br. s., 2H), 4.46-4.59 (m, 4H), 3.90-4.35 (m, 4H), 3.10 (t, J=7.0 Hz, 2H), 2.64 (t, J=7.5 Hz, 2H), 2.11 (s, 6H), 1.26 (t, J=6.21 Hz, 6H). LCMS (m/z): 749.4 [M+H]+.

Example 8

(E)-4-((5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)oxy)butanoic acid

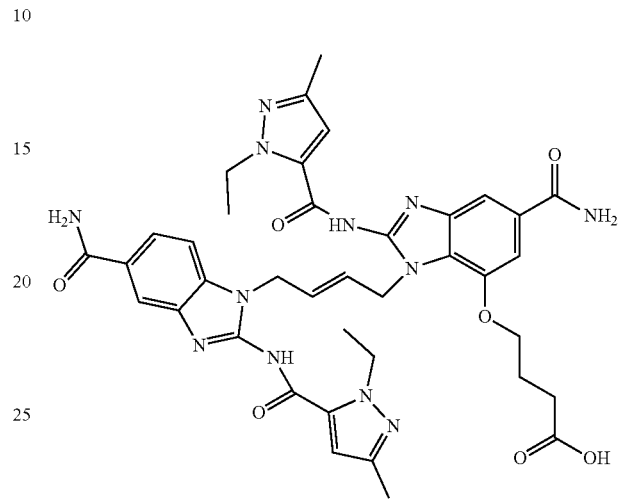

Example 8 can be prepared according to a combination of method 14 and 16 as described in PCT/IB2017/051945 (filed Apr. 5, 2017, herein incorporated in its entirety) with modifications known to one of ordinary skill in the art. The last step of the preparation is provided: Methyl (E)-4-((5-carbamoyl-1-(4-(5-carbamoyl-2-(1-ethyl-3-methyl-1H-pyrazole-5-carboxamido)-1H-benzo[d]imidazol-1-yl)but-2-en-1-yl)-2-(1-ethyl-3-methyl-1H-pyrazole-5-carboxamido)-1H-benzo[d]imidazol-7-yl)oxy)butanoate (40 mg, 0.050 mmol) was dissolved in MeOH and THF (1 mL each) and sodium hydroxide (101 μl, 0.505 mmol, 5N) was added, and the mixture stirred at 25° C. for 18 hr. The reaction was then partitioned between EtOAc and 10% aqueous potassium hydrogen sulfate. The resulting gummy gel mixture was evaporated to near dryness, dissolved in 2 mL MeOH with aqueous sodium hydroxide (5N) to dissolve. The residue was purified via basic reverse phase chromatography (10% to 55% in 0.1% NH$_4$OH in water to MeCN; 50×30 mm Phenomenex Gemini, 5 μM C18 110A column, 10 min gradient). The pure fractions were collected and the product isolated by concentration in vacuo then dried under high vacuum to give the title compound as a white solid. $^1$H NMR (400 MHz, Methanol-$d_4$) γppm 8.45-8.76 (m, 1H), 7.85-8.12 (m, 1H), 7.49-7.78 (m, 2H), 6.92-7.30 (m, 2H), 6.31-6.58 (m, 2H), 5.83-6.02 (m, 1H), 5.56-5.75 (m, 1H), 4.45-4.66 (m, 5H), 3.91-4.16 (m, 4H), 3.6 (q, J=6.3 Hz, 4H), 2.31 (m, 2H), 2.18 (s, 6H), 1.29 (q, J=6.1 Hz, 4H), 1.13 (t, J=6.1 Hz, 6H); LCMS Method K: Rt=0.75 min, [M+H]$^+$=779.4.

Example 9

| | | | |
|---|---|---|---|
| (E)-7-(aminomethyl)-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazole-5-carboxamide 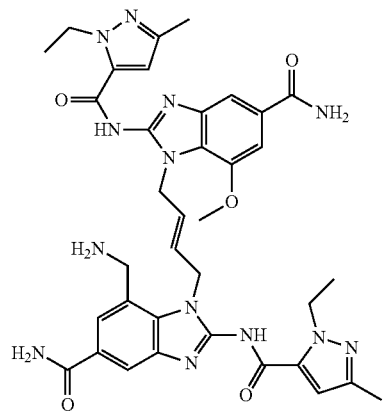 | Method 9 as described in WO 2017/175147 | $^1$H NMR (400 MHz, DMSO-$d_6$) δ ppm 8.15 (s, 1H), 7.95 (t, J = 14.8 Hz, 3H), 7.68 (d, J = 25.8 Hz, 2H), 7.35 (d, J = 18.1 Hz, 3H), 6.52 (d, J = 18.5 Hz, 2H), 5.76 (d, J = 15.9 Hz, 1H), 5.54 (d, J = 15.8 Hz, 1H), 5.08 (s, 2H), 4.88 (s, 2H), 4.51 (d, J = 6.7 Hz, 4H), 3.95 (s, 2H), 3.76 (s, 3H), 2.10 (d, J = 1.8 Hz, 6H), 1.26 (td, J = 7.1, 4.5 Hz, 6H) | LCMS Method A: Rt = 1.205 min, [M + H]$^+$ = 735.8 |

Example 10

(E)-1-(4-(5-carbamoyl-2-(1-ethyl-3-methyl-1H-pyrazole-5-carboxamido)-7-(3-(piperazin-1-yl)propoxy)-1H-benzo[d]imidazol-1-yl)but-2-en-1-yl)-2-(1-ethyl-3-methyl-1Hpyrazole-5-carboxamido)-7-methoxy-1H-benzo[d]imidazole-5-carboxamide

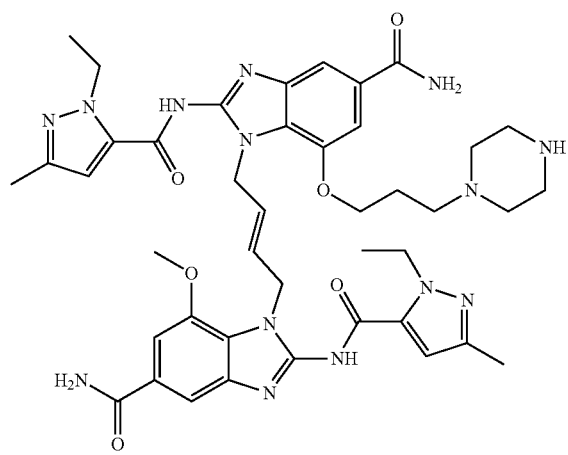

-continued
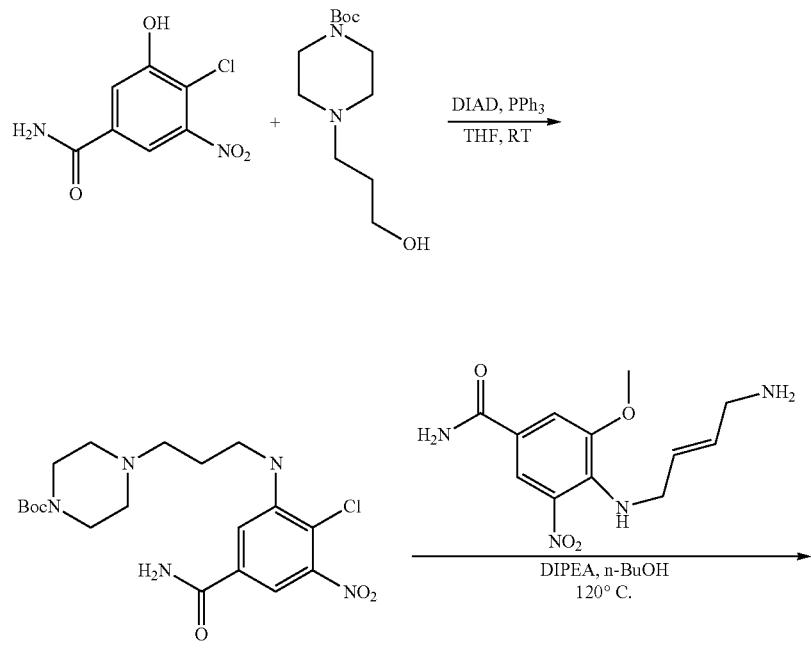
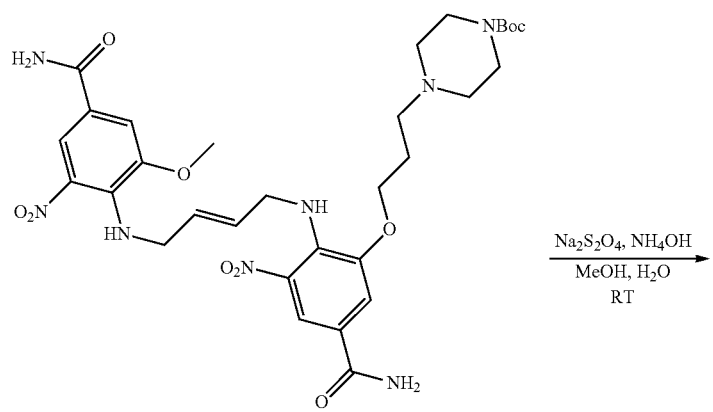
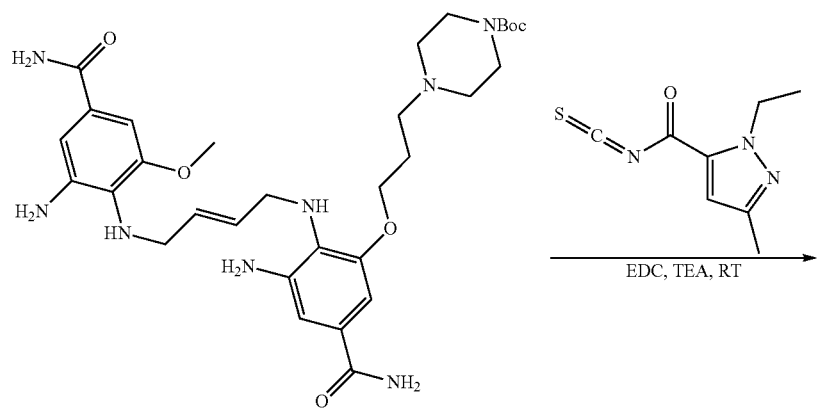

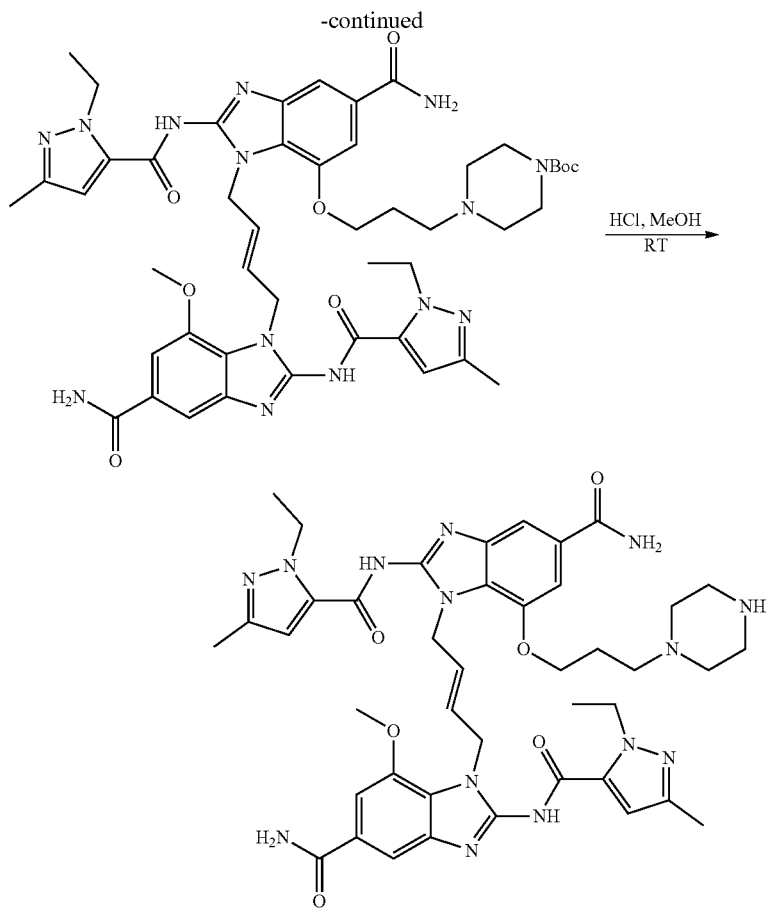

Step 1: tert-butyl 4-(3-(5-carbamoyl-2-chloro-3-nitrophenoxy)propyl)piperazine-1-carboxylate

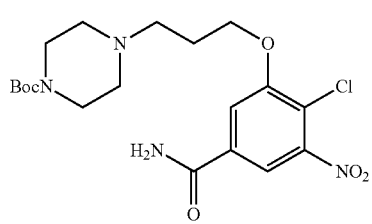 [SMILES: CC(C)(C)OC(=O)N1CCN(CCCOc2cc(C(N)=O)cc([N+](=O)[O-])c2Cl)CC1]

Triphenylphosphine (2.059 g, 7.85 mmol), tert-butyl 4-(3-hydroxypropyl)piperazine-1-carboxylate (1.692 g, 6.93 mmol) and diisopropyl (E)-diazene-1,2-dicarboxylate (1.587 g, 7.85 mmol) were mixed in THF (20 mL) at 0° C., and then 4-chloro-3-hydroxy-5-nitrobenzamide (1 g, 4.62 mmol) was added. The reaction solution was maintained at RT for 16 hrs then the brown reaction solution was partitioned between sat. NaHCO$_3$ (aq) and EtOAc. The organic layer was washed with brine, dried over MgSO$_4$, concentrated and purified on silica gel (20%-80% (3:1 EtOAc/EtOH)/Hexane, with 2% NH$_4$OH; 330 g RediSep column). Desired fractions were combined and concentrated to give the title compound as a white solid (970 mg, 47% yield). $^1$H NMR (400 MHz, DMSO-d$_6$) δ ppm 8.30 (s, 1H), 8.05 (d, J=1.77 Hz, 1H), 7.88 (d, J=1.77 Hz, 1H), 7.80 (s, 1H), 4.28 (t, J=6.21 Hz, 2H), 3.31 (br. s., 4H), 2.48 (t, J=7.10 Hz, 2H), 2.33 (t, J=4.94 Hz, 4H), 1.96 (t, J=6.59 Hz, 2H), 1.40 (s, 9H). LCMS (LCMS Method K): Rt=0.69 min, [M+H]$^+$=443.4.

Step 2: tert-butyl(E)-4-(3-(5-carbamoyl-2-((4-(5-carbamoyl-2-(1-ethyl-3-methyl-1H-pyrazole-5-carboxamido)-7-methoxy-1H-benzo[d]imidazol-1-yl)but-2-en-1-yl)amino)-3-nitrophenoxy)propyl)piperazine-1-carboxylate

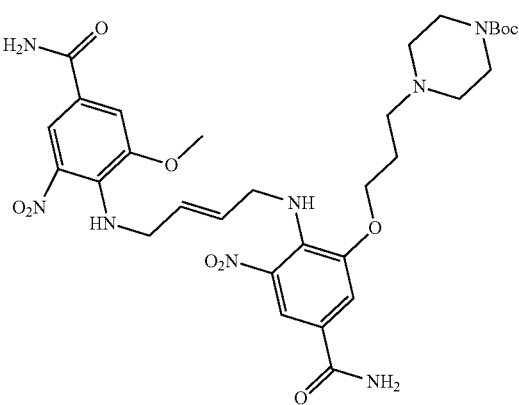 [SMILES: COc1cc(C(N)=O)cc([N+](=O)[O-])c1NC/C=C/CNc1c(OCCCN2CCN(C(=O)OC(C)(C)C)CC2)cc(C(N)=O)cc1[N+](=O)[O-]]

(E)-1-(4-aminobut-2-en-1-yl)-2-(1-ethyl-3-methyl-1H-pyrazole-5-carboxamido)-7-methoxy-1H-benzo[d]imidazole-5-carboxamide, 2Hydrochloride (242 mg, 0.499 mmol)

was dissolved in n-butanol (10 mL) at RT, and then DIPEA (0.476 mL, 2.72 mmol) was added, followed by tert-butyl 4-(3-(5-carbamoyl-2-chloro-3-nitrophenoxy)propyl)piperazine-1-carboxylate (201 mg, 0.454 mmol). The reaction mixture was maintained at 120° C. for 16 hrs. The reaction mixture was cooled to RT and the red solid was collected by filtration (296 mg, 73% yield). $^1$H NMR (400 MHz, DMSO-$d_6$) δ ppm 8.14 (d, J=1.77 Hz, 1H), 8.00 (br. s., 2H), 7.84 (t, J=6.46 Hz, 1H), 7.66 (s, 1H), 7.44 (s, 1H), 7.30-7.41 (m, 3H), 6.59 (s, 1H), 5.61-5.87 (m, 2H), 4.89 (d, J=5.58 Hz, 2H), 4.58 (q, J=7.35 Hz, 2H), 4.14 (br. s., 2H), 3.89 (t, J=6.34 Hz, 2H), 3.84 (s, 3H), 3.25 (br. s., 4H), 2.27 (t, J=6.72 Hz, 2H), 2.21 (br. s., 4H), 2.16 (s, 3H), 1.75 (d, J=6.08 Hz, 2H), 1.39 (s, 9H) 1.23-1.35 (m, 3H). LCMS (LCMS Method K): Rt=0.78 min, [M+H]$^+$=818.4.

Step 3: tert-butyl(E)-4-(3-(3-amino-5-carbamoyl-2-((4-(5-carbamoyl-2-(1-ethyl-3-methyl-1H-pyrazole-5-carboxamido)-7-methoxy-1H-benzo[d]imidazol-1-yl)but-2-en-1-yl)amino)phenoxy)propyl)piperazine-1-carboxylate

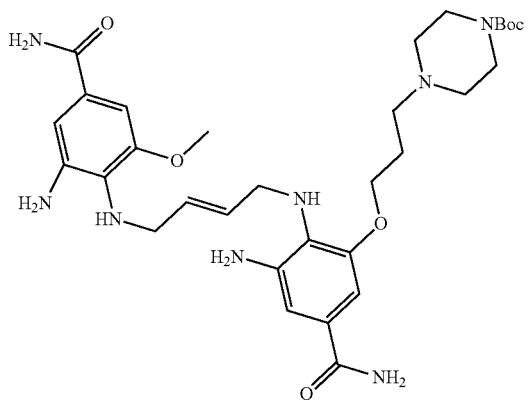 [SMILES: COc1cc(C(N)=O)cc(N)c1NC/C=C/CNc1c(N)cc(C(N)=O)cc1OCCCN1CCN(C(=O)OC(C)(C)C)CC1]

Sodium hydrosulfite (371 mg, 1.81 mmol) was dissolved in H$_2$O (2 mL) at RT, and then a solution of tert-butyl (E)-4-(3-(5-carbamoyl-2-((4-(5-carbamoyl-2-(1-ethyl-3-methyl-1H-pyrazole-5-carboxamido)-7-methoxy-1H-benzo[d]imidazol-1-yl)but-2-en-1-yl)amino)-3-nitrophenoxy)propyl)piperazine-1-carboxylate (296 mg, 0.362 mmol) and ammonium hydroxide (0.486 mL, 3.62 mmol) in 5 mL MeOH was added. The reaction mixture was maintained at room temperature for 2 hrs, then the reaction mixture was filtered and the filtrate was partially concentrated to remove MeOH. The resulting yellow aqueous mixture was then extracted with EtOAc 3 times, the organic extracts were combined and concentrated to provide the title compound as a yellow solid (114 mg, 40% yield). $^1$H NMR (400 MHz, METHANOL-$d_4$) δ ppm 7.60 (d, J=1.27 Hz, 1H), 7.31 (d, J=1.27 Hz, 1H), 6.81 (d, J=1.77 Hz, 1H), 6.67 (s, 1H), 6.59 (d, J=1.77 Hz, 1H), 5.74-5.84 (m, 1H), 5.53-5.65 (m, 1H), 4.12 (q, J=7.18 Hz, 2H), 3.84-3.91 (m, 3H), 3.61-3.71 (m, 4H), 3.38 (br. s., 4H), 2.31-2.36 (m, 6H), 2.26 (s, 3H), 2.03 (s, 2H), 1.68-1.78 (m, 2H), 1.47 (s, 9H), 1.42 (t, J=7.10 Hz, 3H). LCMS (LCMS Method K): Rt=0.65 min, [M+H]$^+$=788.5.

Step 4: tert-butyl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)piperazine-1-carboxylate

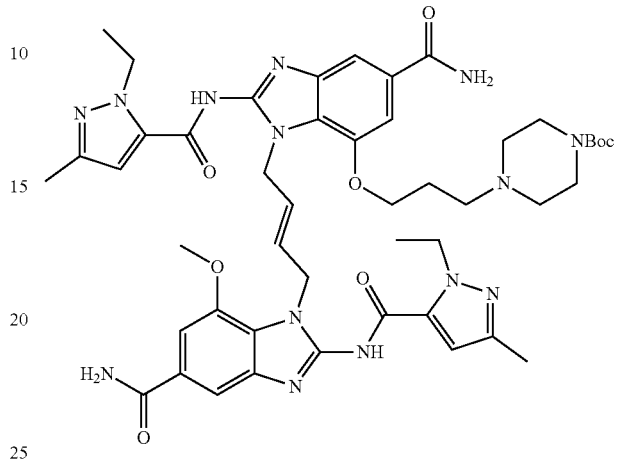

Tert-butyl (E)-4-(3-(3-amino-5-carbamoyl-2-((4-(5-carbamoyl-2-(1-ethyl-3-methyl-1H-pyrazole-5-carboxamido)-7-methoxy-1H-benzo[d]imidazol-1-yl)but-2-en-1-yl)amino)phenoxy)propyl) piperazine-1-carboxylate (114 mg, 0.145 mmol) was dissolved in DMF (10 mL) at 0° C., and then 1-ethyl-3-methyl-H-pyrazole-5-carbonyl isothiocyanate (0.362 mL, 0.145 mmol) was added. The reaction mixture was maintained at 0° C. for 15 min. then TEA (0.050 ml, 0.362 mmol) and EDC (33.3 mg, 0.174 mmol) were added to the reaction mixture. The reaction mixture was maintained at RT for 16 hrs. The reaction mixture was then added into a stirring solution of sat. NaHCO$_3$ (aq). The resulting white precipitate was collected by filtration to provide the title compound (103 mg, 75% yield). LCMS (LCMS Method K): Rt=0.82 min, [M+H]$^+$=950.5.

Example 10

(E)-1-(4-(5-carbamoyl-2-(1-ethyl-3-methyl-1H-pyrazole-5-carboxamido)-7-(3-(piperazin-1-yl)propoxy)-1H-benzo[d]imidazol-1-yl)but-2-en-1-yl)-2-(1-ethyl-3-methyl-1Hpyrazole-5-carboxamido)-7-methoxy-1H-benzo[d]imidazole-5-carboxamide

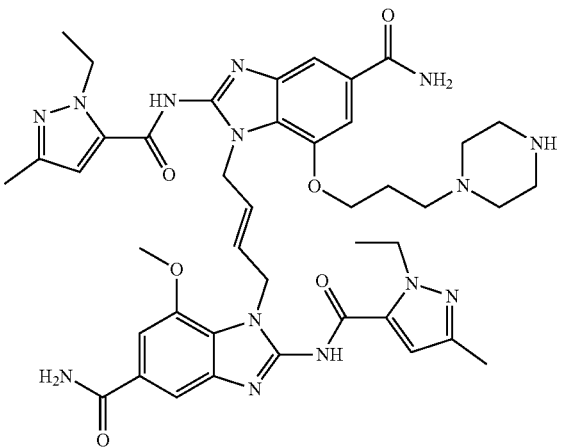 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCN3CCNCC3)c21]

Step 5: tert-butyl (E)-4-(3-((5-carbamoyl-1-(4-(5-carbamoyl-2-(1-ethyl-3-methyl-1H-pyrazole-5-carboxamido)-7-methoxy-1H-benzo[d]imidazol-1-yl)but-2-en-1-yl)-2-(1-ethyl-3-methyl-1H-pyrazole-5-carboxamido)-1H-benzo[d]imidazol-7-yl)oxy)propyl)piperazine-1-carboxylate (103 mg, 0.109 mmol) was dissolved in MeOH (2 mL) and DCM (2 mL), and then HCl (4N in 1,4-dioxane) (0.271 mL, 1.085 mmol) was added. The reaction mixture was maintained at RT for 16 hrs. DMSO (2 mL) was then added to the reaction mixture, and this mixture was filtered and the filtrate was concentrated and purified by HPLC (XSELECT CSH C18 column, 150 mm×30 mm, i.d. 5 um packing diameter, 30%-85% 10 mM ammonium bicarbonate in water with acetonitrile). The clean fractions after HPLC were combined and partially concentrated to yield the title compound as a white precipitate (25 mg, 27% yield). $^1$H NMR (400 MHz, METHANOL-$d_4$) δ ppm 7.57 (d, J=16.48 Hz, 2H), 7.14-7.30 (m, 2H), 6.50-6.70 (m, 2H), 5.81 (d, J=3.04 Hz, 2H), 4.99 (br. s., 4H) 4.50-4.69 (m, 4H) 3.86 (t, J=5.70 Hz, 2H) 3.69 (s, 3H) 2.81 (t, J=4.69 Hz, 4H) 2.32-2.36 (m, 6H) 2.20 (d, J=12.93 Hz, 6H), 1.70 (br. s., 2H), 1.25-1.45 (m, 6H). LCMS (LCMS Method K): Rt=0.67 min, [M+H]$^+$=849.8.

Example 11

(E)-1-(4-(5-carbamoyl-2-(1-ethyl-3-methyl-1H-pyrazole-5-carboxamido)-7-(3-morpholinopropoxy)-1H-benzo[d]imidazol-1-yl)but-2-en-1-yl)-7-ethoxy-2-(1-ethyl-3-methyl-1H-pyrazole-5-carboxamido)-1H-benzo[d]imidazole-5-carboxamide mg, 0.065 mmol) was dissolved in DMF (655 uL) at 0° C., and then 1-ethyl-3-methyl-1H-pyrazole-5-carbonyl isothiocyanate (196 μl, 0.079 mmol) was added. The reaction solution was maintained at 0° C. for 15 min., then EDC (15.06 mg, 0.079 mmol) and TEA (22.81 μl, 0.164 mmol) were added and the reaction solution was maintained at RT. After 16 hrs, the reaction was concentrated and the yellow residue was purified by HPLC (XSELECT CSH C18 column, 150 mm×30 mm, i.d. 5 um packing diameter, 15%-55% 10 mM ammonium bicarbonate in water with acetonitrile). The desired fractions were combined and concentrated to provide the title compound as a white solid (19.2 mg, 34% yield). $^1$H NMR (400 MHz, METHANOL-$d_4$) δ ppm 7.62 (d, J=1.27 Hz, 1H), 7.58 (d, J=1.27 Hz, 1H), 7.24 (d, J=1.27 Hz, 1H), 7.20 (d, J=1.27 Hz, 1H), 6.64 (s, 1H), 6.62 (s, 1H), 5.78 (d, J=3.30 Hz, 2H), 5.01 (d, J=2.79 Hz, 4H), 4.63 (q, J=7.10 Hz, 4H), 3.86-4.08 (m, 6H), 3.69-3.81 (m, 2H), 3.37 (br. s., 2H), 3.16-3.23 (m, 2H), 2.97-3.13 (m, 2H), 2.23 (s, 6H), 1.96-2.04 (m, 2H), 1.39 (t, J=7.10 Hz, 6H), 1.15 (t, J=6.97 Hz, 3H).
LCMS (LCMS Method K): Rt=0.76 min, [M+H]$^+$=864.5.

Example 12

(E)-1-(4-(5-carbamoyl-2-(1-ethyl-3-methyl-1H-pyrazole-5-carboxamido)-7-methoxy-1H-benzo[d]imidazol-1-yl)but-2-en-1-yl)-7-(3-(dimethylamino)propoxy)-2-(1-ethyl-3-methyl-1H-pyrazole-5-carboxamido)-1H-benzo[d]imidazole-5-carboxamide, 2Hydrochloride

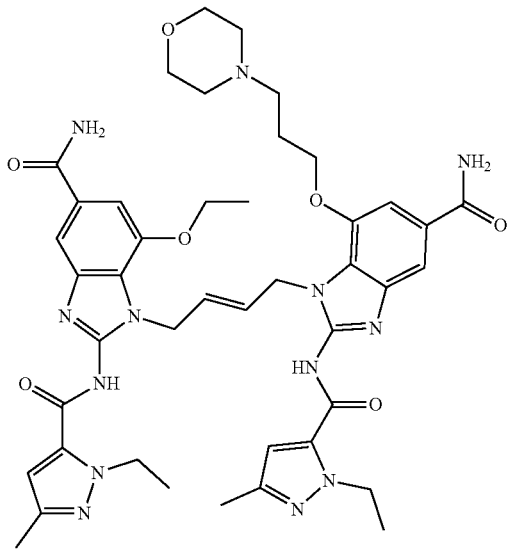 [SMILES: CCOc1cc(C(N)=O)cc2nc(NC(=O)c3cc(C)nn3CC)n(C/C=C/Cn3c(NC(=O)c4cc(C)nn4CC)nc4cc(C(N)=O)cc(OCCCN5CCOCC5)c43)c12]

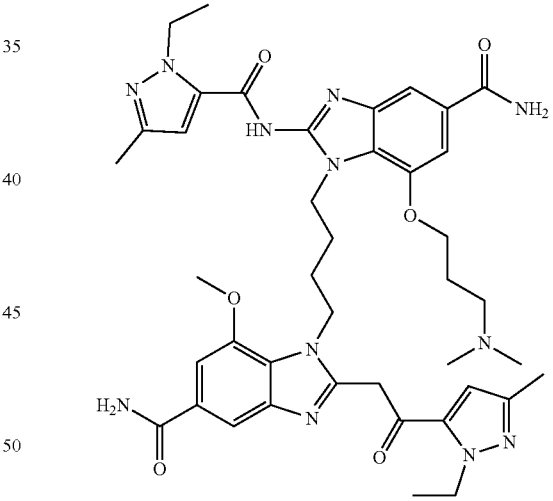

To a solution of (E)-1-(4-(5-carbamoyl-2-(1-ethyl-3-methyl-1H-pyrazole-5-carboxamido)-7-(3-hydroxypropoxy)-1H-benzo[d]imidazol-1-yl)but-2-en-1-yl)-2-(1-ethyl-3-methyl-1H-pyrazole-5-carboxamido)-7-methoxy-1H-benzo[d]imidazole-5-carboxamide, hydrochloride (150 mg, 0.184 mmol) in DMF (2 mL) was added TEA (0.20 mL, 1.435 mmol). The solution was cooled to 0° C. Methanesulfonyl chloride (42.0 mg, 0.367 mmol) was added at this temperature. The reaction mixture was stirred at this temperature for 1 hr then another 1 eq. of methanesulfonyl chloride (21.0 mg, 0.183 mmol) was then added, and the reaction was continued at 0° C. for 1 hr. K$_2$CO$_3$ (127 mg, 0.918 mmol) was then added to reaction mixture followed by 1 ml of dimethyl amine (2 M in THF, 2.0 mmol). The Example 38 can be prepared according to method 20 with modifications known to one of ordinary skill in the art. The last step of the preparation is provided: (E)-1-(4-(((2-amino-4-carbamoyl-6-(3-morpholinopropoxy)phenyl)amino)but-2-en-1-yl)-7-ethoxy-2-(1-ethyl-3-methyl-1H-pyrazole-5-carboxamido)-1H-benzo[d]imidazole-5-carboxamide (46 reaction mixture was stirred at 80° C. in a sealed tube for 2 hours then allowed to cool to room temperature, and the crude material was purified by mass directed HPLC. The HPLC analysis was conducted on an XSELECT SCH C18 column. Solvent condition: A=10 mM Ammonium Bicarbonate in $H_2O$ adjusted to pH 10 with Ammonia, B=MeCN B %: 15-55. Collected desired MW peaks. Solvent was removed and the residue was dissolved in 1 mL MeOH. 4N HCl in dioxane (1 mL) was added. The solution was stirred at room temperature for 10 min. Removed solvent and the solid washed with ethyl ether (5 ml×2) to provide the title compound (76 mg, 0.082 mmol, 44.7% yield). $^1H$ NMR (DMSO-$d_6$, 600 MHz): δ (ppm) 12.89 (br s, 2H), 10.18-10.41 (m, 1H), 7.96-8.04 (m, 2H), 7.66 (d, J=10.0 Hz, 2H), 7.35-7.41 (m, 2H), 7.28-7.35 (m, 2H), 6.53 (d, J=2.8 Hz, 2H), 5.82 (dt, J=15.5, 5.3 Hz, 1H), 5.71 (dt, J=15.4, 5.6 Hz, 1H), 4.85-4.98 (m, 4H), 4.52 (quin, J=6.5 Hz, 4H), 3.96-4.04 (m, 2H), 3.70 (s, 3H), 3.00-3.09 (m, 2H), 2.66 (d, J=4.8 Hz, 6H), 2.11 (d, J=4.4 Hz, 6H), 1.85-2.03 (m, 2H), 1.20-1.32 (m, 6H); LCMS Method K: Rt=0.67 min, $[M+H]^+$=808.5

Example 13

STING Agonist Formulations:
STING agonist was prepared in either a PEG/Saline formulation or a DMSO/PEG/Water formulation for the IV tumor regression and pK/pd experiments disclosed herein.
DMSO/PEG/Water formulation was prepared using the following methods:
1) STING agonist dissolved with DMSO first, then vortex to make sure the compound is in solution,
2) PEG added to the DMSO-compound in step 1, then vortex;
3) Saline or water added depending the water depending the formulation to make one of three formulations.
1% DMSO/30% PEG300/69% water
–5% DMSO/30% PEG300/65% water
–10% DMSO/30% PEG300/60% water
PEG/Saline formulation was prepared as follows:
1) STING agonist was dissolved in 100% PEG 400 or PEG-300, then sonicated in heated water bath for 30 min to ensure the compound was completely in solution,
2) Saline added and continue to sonicated in heated water bath to make sure the compound is uniformed mixed and stay in the solution to make one of two formulations.
–40% PEG400 or PEG-300/Saline
–40% PEG400 or PEG-300/Water
Materials
Sigma: 202398 PEG-400
Sigma: D1435: DMSO
Hospira: NDC0409-7984-36: 0.9% Saline
Baxter: 2F7114: Sterile Water.
Sigma: 202371: PEG-300.

Example 14

Compound 1 was assessed in a genetic STING knock-out (KO) mouse model using wild type (WT) animal as a control for off target activity. Both STING KO and WT animals (Jackson Laboratories) were dosed with Compound 1 at 2.5 mg/kg in PEG/Saline Vehicle (40% PEG-400 in normal saline) then sacrificed after 3.5 h. Serum cytokines were analyzed using PBL[@], and eBioscience[@] Elisa and MSD[@] mouse multiplex assay kits.
Compound 1 induced cytokine response only in WT mice with complete loss of IFN-β and other cytokines induction in the STING$^{-/-}$ mice showing that Compound 1 induces a STING-specific cytokine response. Compound 1 induced pro-inflammatory cytokines like IL-6 and TNF as well as a T cell specific response demonstrated by increase in IFN-γ in WT but not in STING KO mouse (FIG. 1).

Example 15

CT-26 Single Tumor Efficacy Upon IV Administration of Compound 1

Figure 6:
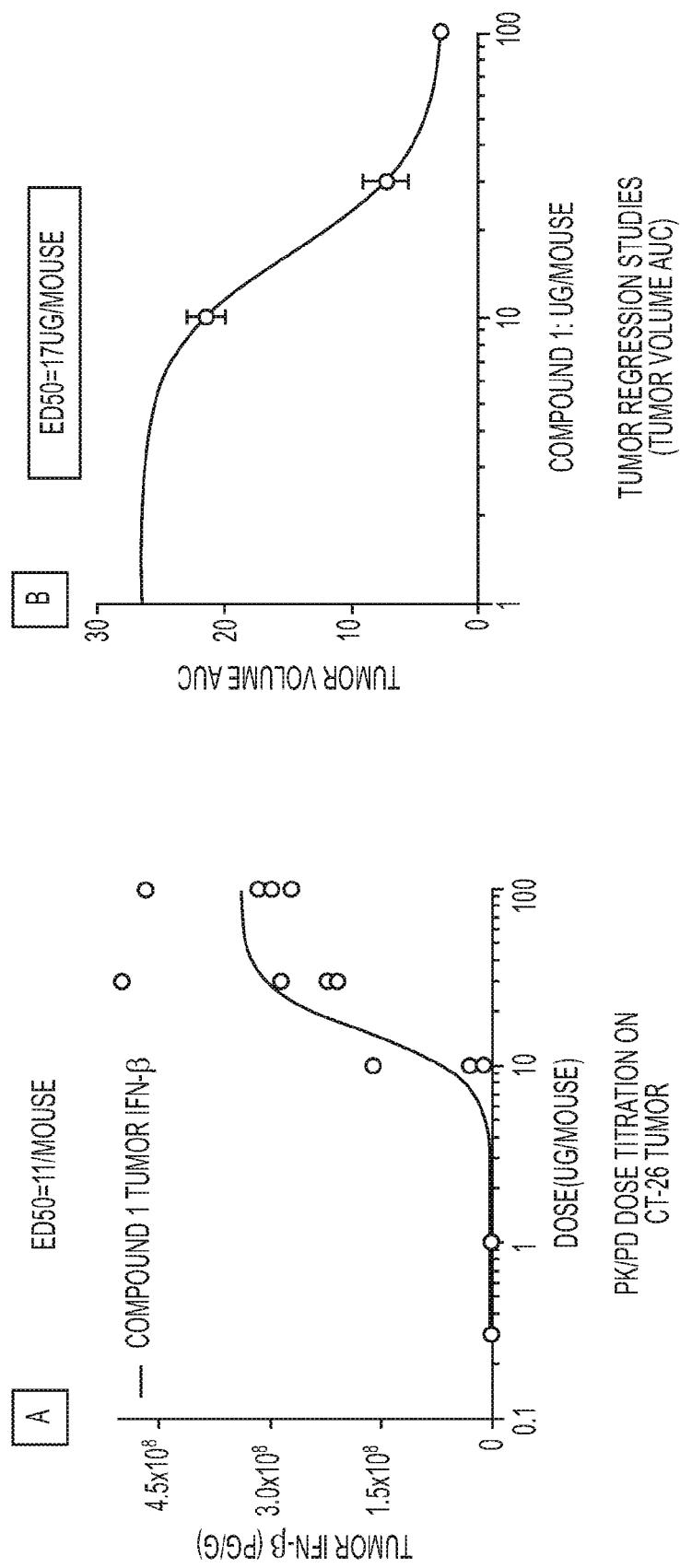
FIG. 6: IV pK/pD Correlation to Tumor Regression.
Figure 11:
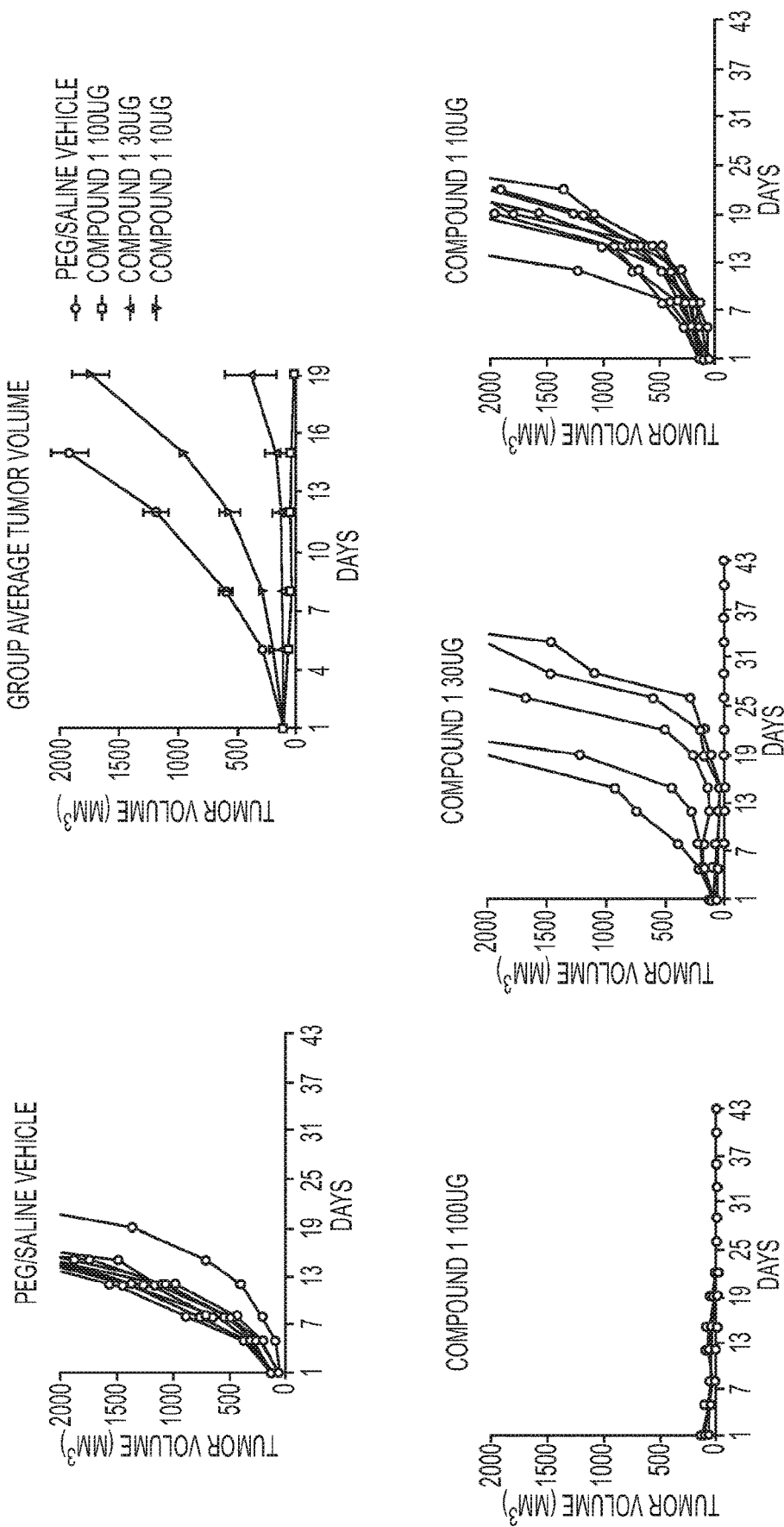
FIG. 11: Group average and individual mouse tumor volume—IV administration of Compound 1 in BALB/c mice bearing a single CT-26 tumor (n=10/group). The average tumor volume for mice in each group is shown along with individual mouse tumor volumes with the orange number in each panel representing the number of complete tumor regressions.

Compound 1 causes significant tumor growth inhibition in BALB/c mice containing CT-26 tumors following intravenous injection. Mice were grouped n=10 per dose (100 µg, 30 µg, or 10 µg of Compound 1) with a dosing regimen on days 0, 3 and 7. Tumors were measured twice weekly and mice were euthanized when tumor volume reached >2000 $mm^3$ or day 43, whichever came first. Compound 1 induced a significant dose dependent CT-26 tumor growth inhibition at all doses tested for treatment groups compared to vehicle control (100 µg p<0.0001; 30 µg p<0.0001; 10 µg p=0.0016). Treatment with 100 µg Compound 1 resulted in 9 complete tumor regressions. Treatment with 30 µg resulted in 5 complete tumor regressions and substantial tumor growth delay in the other 5 animals. There were no complete regressions with 10 µg treatment, however, there was significant tumor growth delay vs. vehicle control (FIG. 11).
The tumor volume from the regression studies above were used to generate the ED50 curves data analysis, using the tumor volume area under the curve (AUC) for the duration of animal survived from all 10 mice per group then using Graphpad software four parameter to generated the ED50 dose as illustrated in FIG. 6B.

Example 16: IV PK/PD Time Course of Compound 1 in BALB/c Bearing a CT-26 Tumor

Figure 2:
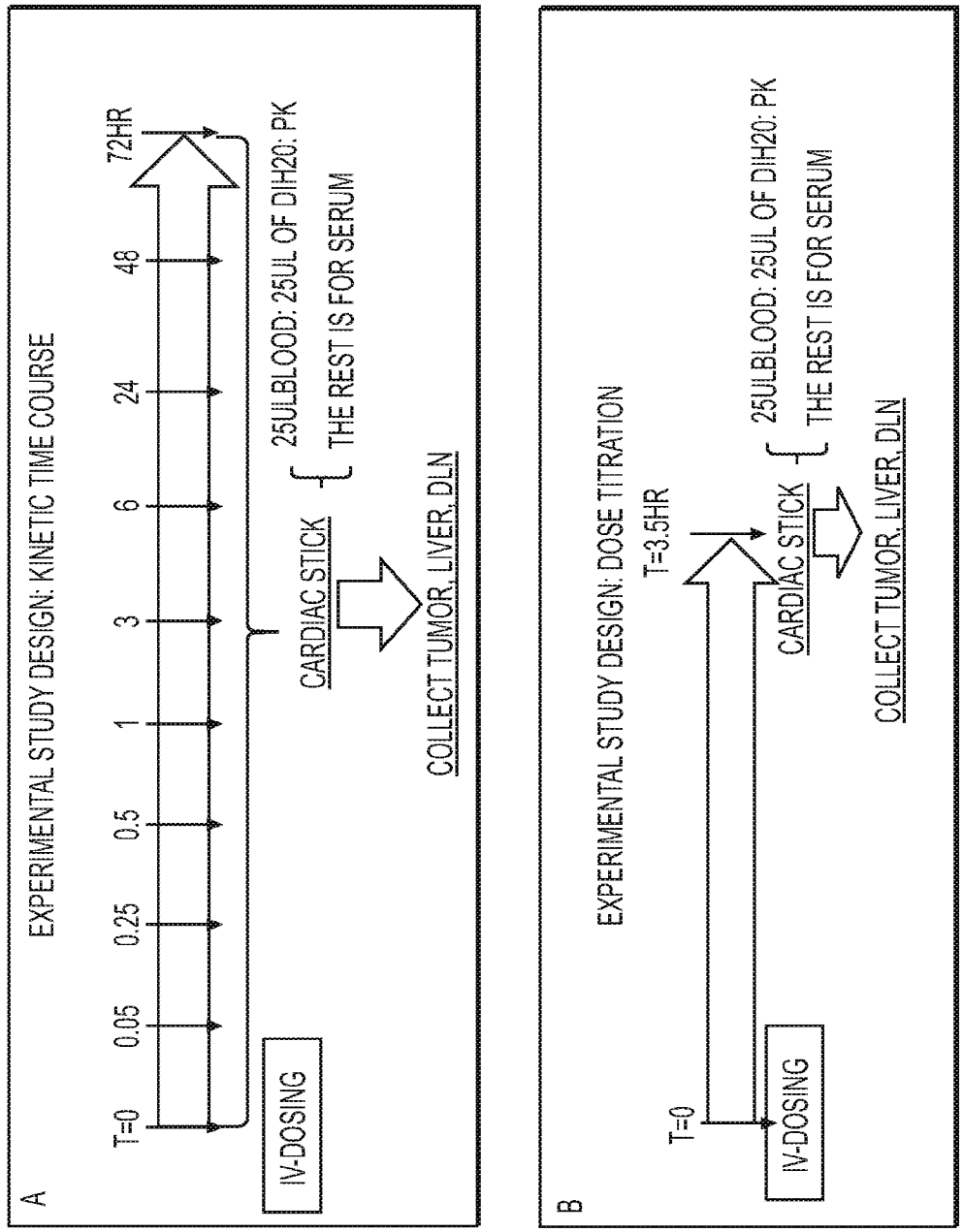
FIG. 2: Schematic depicting IV Administration of Compound 1 for kinetic timecourse study of pharmacokinetics and pharmacodynamics of Compound 1 FIG. 2 (A): Kinetic time course pk/pd study outline (30 μg/Mouse~1.5 mg/kg)
Figure 2:
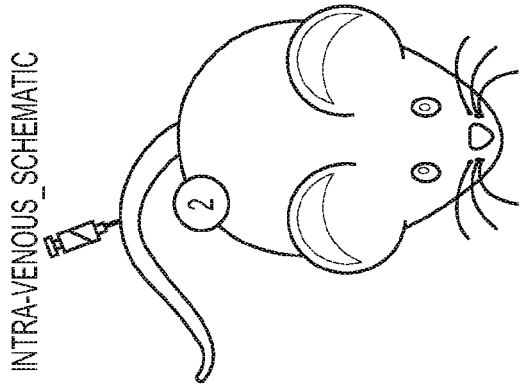
Figure 3:
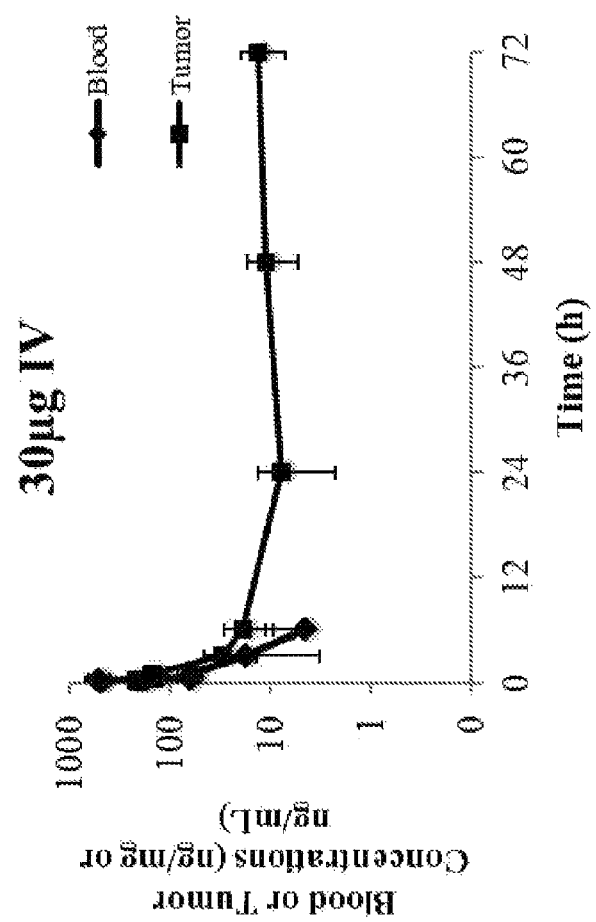
FIG. 3: Blood and tumor drug concentration-time profile following a single IV bolus dose 30 μg Compound 1. Each time point represents data collected from four repeat animals.
Figure 4:
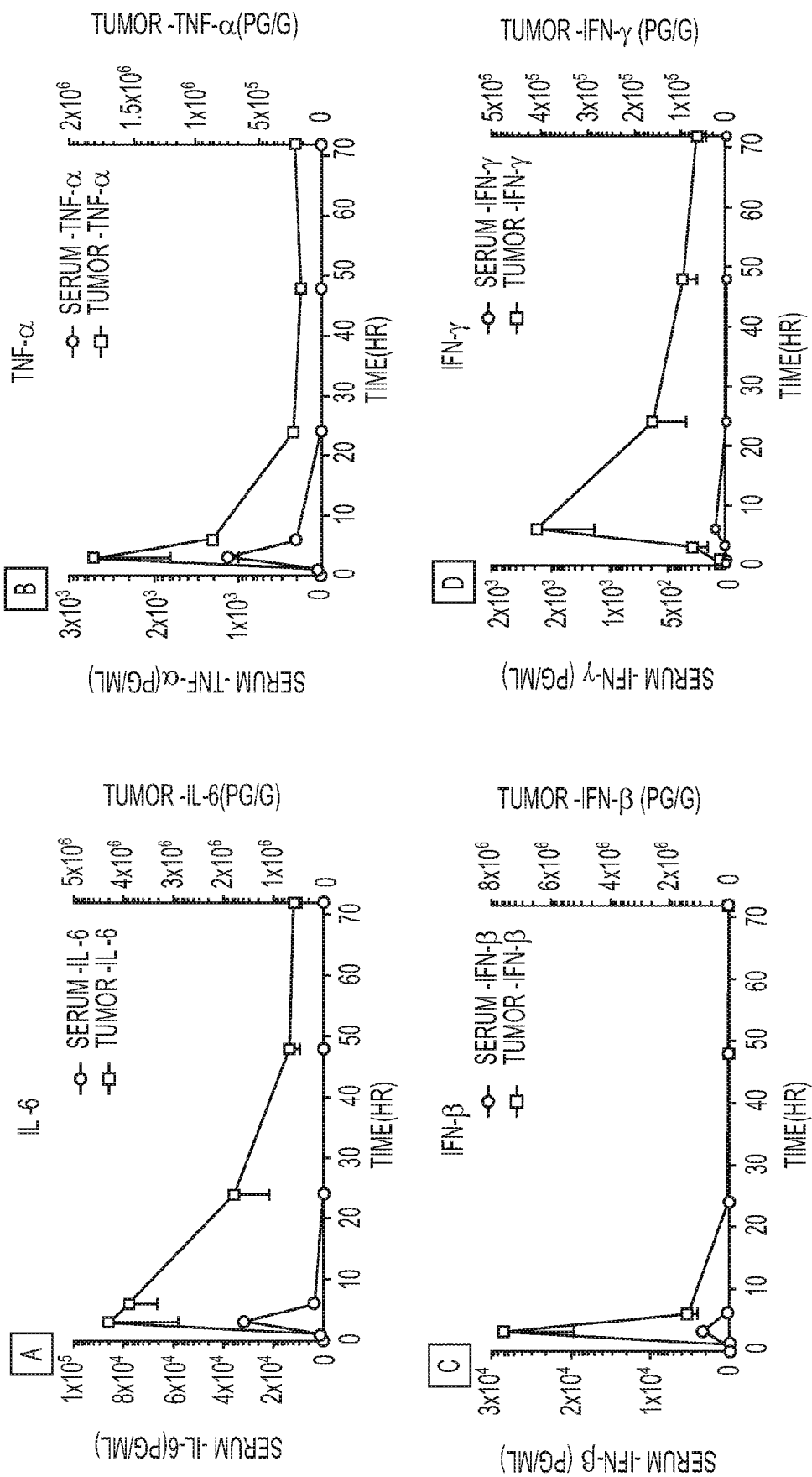
FIG. 4 (FIGS. 4A, 4B, 4C, and 4D): IV-Administration of Compound 1, kinetic time course of cytokine response BALB/c mice bearing a single CT-26 tumor (30 μg/Mouse~1.5 mg/kg). Representative of PD responses in single bolus IV administration of Compound-1 in time course PK/PD on CT-26 tumor in BALB/c Mouse FIG. 4(A) Serum and Tumor IL-6.

Compound 1 is enriched in tumors upon intravenous (IV) administration and generates significantly elevated tumor cytokine levels compared to serum cytokines. Here the key characteristic met by Compound 1 is that it generates high tumor cytokines that correlate with tumor efficacy while minimizing systemic cytokines typically associated with systemic toxicities of cytokine release.
Seven-week-old female BALB/c mice (Charles River) were inoculated with CT-26 (ATCC: CRL-2638) cells on the right hind flank. When average tumor volume was 100 $mm^3$, mice were randomized based on tumor volume into the study with randomization set as day 0. For pharmacokinetic/pharmacodynamic (pk/pd) studies, animals received an IV bolus of Compound 1 injection and sacrificed at the specified time point and dose. The tumors and blood were collected for each cohort (N=4) representing single time-point (0.05, 0.25, 0.5, 1, 3, 6, 24, 48, and 72 hours post-dose) and a 30 µg dose (see FIG. 2). A panel of cytokines were measured from blood and tumor tissue homogenate using MSD©-10 plex, and PBL©-IFNβ and eBioscience©-IFNα ELISA assay kits (IL-1b, IL-2, IL-6, IL-8, IL-10, IL12, IFN-α, IFN-β, IFN-γ, and TNF-α) on the tumor lysates and serum from each animal for each cohort in the pk/pd experiment. The drug concentration of Compound 1 from blood and tumor lysate from these pk/pd studies were analyzed by LC-MS/MS.
Compound 1 rapidly distributed into tumor with a long terminal half-life of about 25 hours in tumor. The ratio of tumor to blood AUC was around 1. Blood and tumor concentration-time profile is shown in (See FIG. 3).
The time-course cytokine response (select cytokines IL-6, TNF-α, IFN-β and IFN-γ depicted here) increased in both serum and tumors and reached a peak at approximately 3.5 hours in both serum and tumor homogenates following IV administration of Compound 1 (see FIG. 4). A key aspect of Compound 1 systemic activity is that there was significantly higher level of cytokines observed in tumors compared to serum with the tumor to serum ratio equivalent of 135, 1607, 4000 and 2200 folds for IL-6, TNF-α, IFN-γ, and IFN-β, respectively. Compound 1 demonstrates a key feature of a systemically delivered STING agonist that generates tumor cytokines while minimizing the systemic cytokines release typically associated with systemic toxicity. Compound 1 achieved these characteristics for tumor selectivity upon IV administration with good pk/pd correlation.

Figure 5:
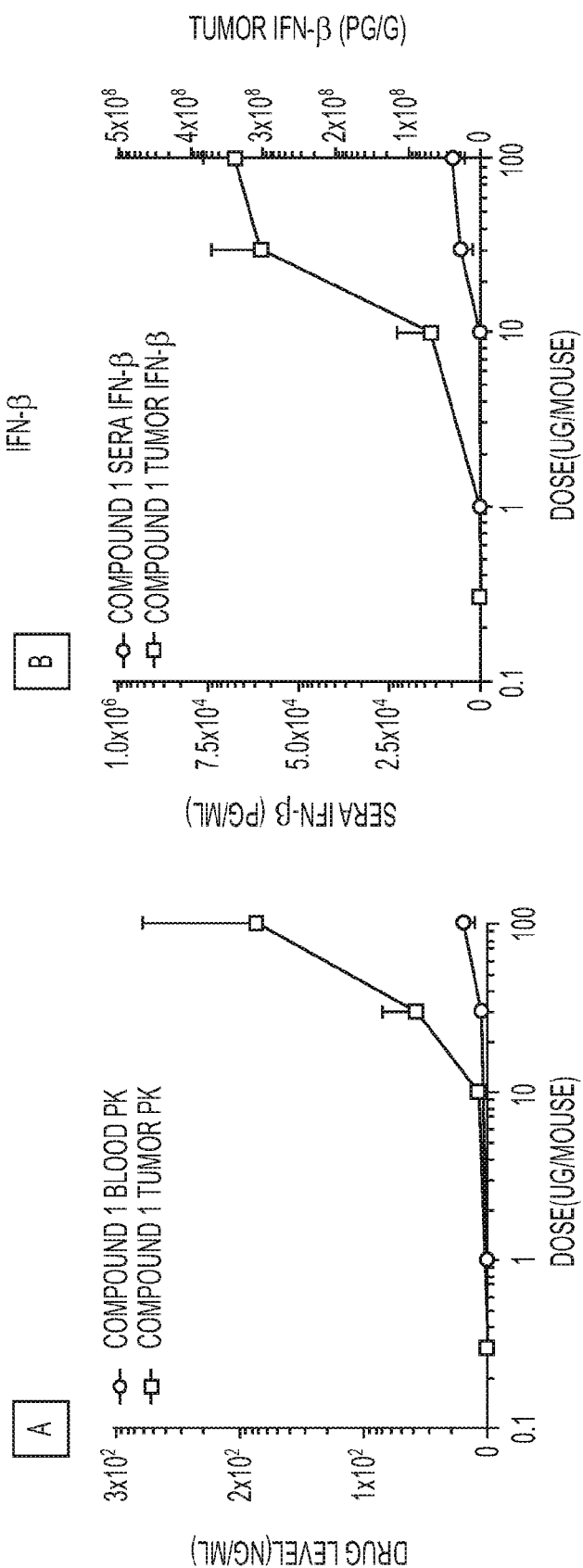
FIG. 5.

Example 17: IV PK/PD Dose Titration of Compound 1 in BALB/c Mice Bearing a CT-26 Tumor Blood and tumor concentrations of Compound 1 and the cytokine responses were measured in BALB/c mice bearing a single CT-26 tumor following escalating IV bolus doses of 0.001 to 100 μg per mouse. Blood and tumors were collected at peak cytokine response time of 3.5 hour post dose and analyzed for the cytokine response and concentration of the drug. The average concentrations of Compound 1 in blood and tumor are reported in Table 1. Despite the high variability of measured tumor drug concentrations, there is an approximate 10-fold higher level of Compound 1 in tumors as compared to blood upon IV injection (See FIG. 5).

TABLE 1

Blood and tumor concentrations in CT26 tumor bearing mice following escalating IV bolus doses (n = 4, composite)

| Compound 1 IV Bolus Dose (μg) | Blood | | Tumor | |
|---|---|---|---|---|
| | Avg. Concentration (ng/mL) | SD | Avg. Concentration (ng/g) | SD |
| 0.3 | 0.63 | 0.65 | <LLQ | NA |
| 1 | NS | NA | 0.66 | NA |
| 10 | 7.28 | 1.08 | 4.36 | 6.97 |
| 30 | 57.45 | 54.88 | 3.81 | 3.37 |
| 100 | 186.43 | 184.31 | 14.37 | 15.86 |

NS; no sample,
<LLQ; below the limit of quantitation.
NA; not applicable

Concentrations of IFNβ increased in tumors with increasing dose of Compound 1 (FIG. 5(B)). Similar to the high tumor-to-blood ratio of cytokines observed in the time-course study, the IFNβ response was significantly higher in tumors as compared to serum with increasing amount of Compound 1. The dose response of cytokines appears saturated at the highest IV doses studied (30-100 μg~1.2-4 mg/kg) and is about 450-fold higher in tumors compared to serum (3.4 μg/g~tumor versus 7.9 ng/mL). The IV dose that generates 50% maximum IFNβ response (ED5) was determined to be 11 μg/mouse or about 0.55 mg/kg (FIG. 6A—correlation pk/pd to tumor regression) and correlate with the IV dose titration efficacy $ED_{50}$ of 17 μg/mouse determined from the plot of tumor volume area under the curve (FIG. 6B). Overall, the analysis of tumor and blood compound and cytokine levels demonstrates excellent correlation between $ED_{50}$ determined from IV efficacy and tumor extracted IFNβ.

Figure 7:
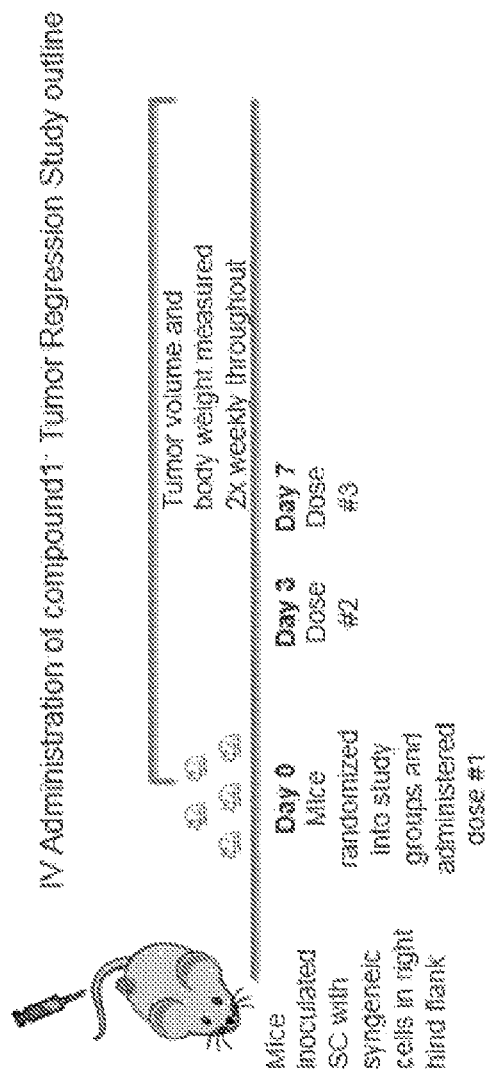
FIG. 7: Schematic of tumor regression study outline on IV administration dosing schedule and tumor monitoring.

Example 18—Efficacy of Compound 1 Upon IV Administration in a Variety of Murine Tumor Models Compound 1 demonstrated tumor growth inhibition on different murine tumors (FIG. 8) upon IV administration. Each murine tumor model was progressed in a similar method by subcutaneous inoculation of specified tumor cells (CT-26 (colon), EMT-6 (breast), H22 (liver), Pan02 (pancreas), RM1 (prostate), B16BL6 and B16F10 (melanoma). Tumors were grown to 100 $mm^3$ followed by randomization and three repeat IV doses of 30 μg or 10 μg (depending on the murine tumor model) on days 1, 4, and 8. Body weight and tumor volumes were measured for 30 days following the first IV dose or when the tumors reached 2000 $mm^3$ (FIG. 7).

Figure 8:
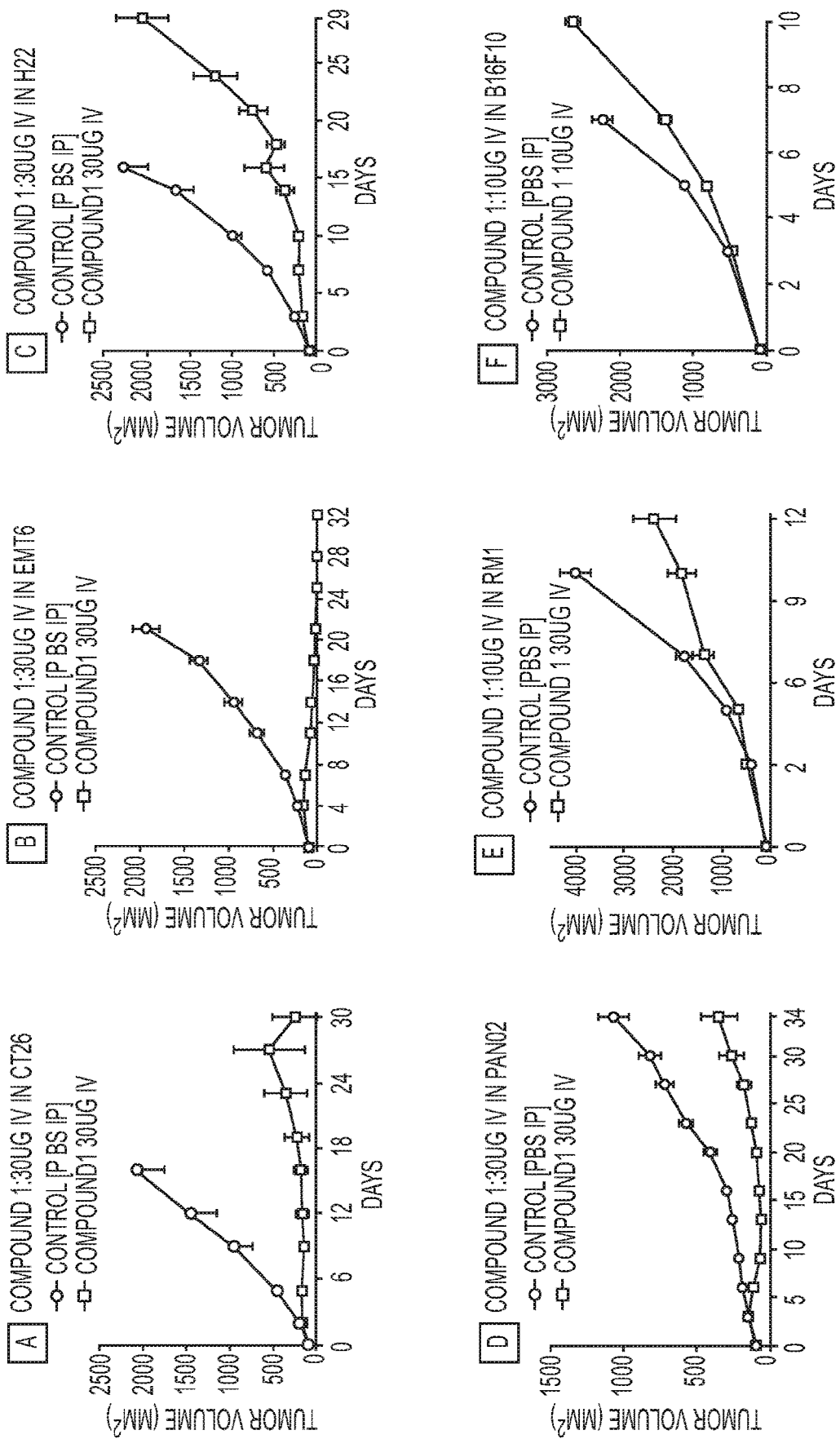
FIG. 8: IV administration effect of Compound 1 on different tumors mouse models (A)CT-26: Colon; (B)EMT6: Breast; (C)H22: Liver; (D)Pan02: Panreas; (E)RM1: Prostate; (F) B16F10: melanoma.

As depicted in FIG. 8, Compound 1 demonstrated tumor growth inhibition in multiple tumor models upon IV delivery with varying degrees of tumor volume efficacy.

Example 19—Activating STING with Compound 1 Engaged CD-8 T Cells for Long Term Immunity Activating STING with Compound 1 induced CD8 T cells that ultimately led to induced long-term immunity. Compound 1 engaged CD8 T-cells in CT-26 tumor regression study. A CD-8 neutralizing antibody was administered with Compound 1 in a CT-26 tumor model.

Six to eight week old female BALB/c mice (Envigo) were inoculated subcutaneously with CT-26 cells on the right hind flank. When average tumor volume was ~100 $mm^3$, mice were randomized based on tumor volume into study groups with 10 mice per group. Compound 1 was dosed at 30 μg and 10 μg/mouse groups. In a separate group, mice were treated with a CD8 depleting antibody to deplete CD 8 T-cells or an IgG control followed by three repeat doses of 30 μg Compound 1.

On day 0, mice were administered a 300 g intraperitoneal (IP) dose of anti-CD8 antibodies in 100 μl saline vehicle. T-cell depletion doses were given on days 1, 4, and 8 while compound 1 was injected intravenously in the formulation of 40% PEG-400 in saline vehicle.

Figure 10:
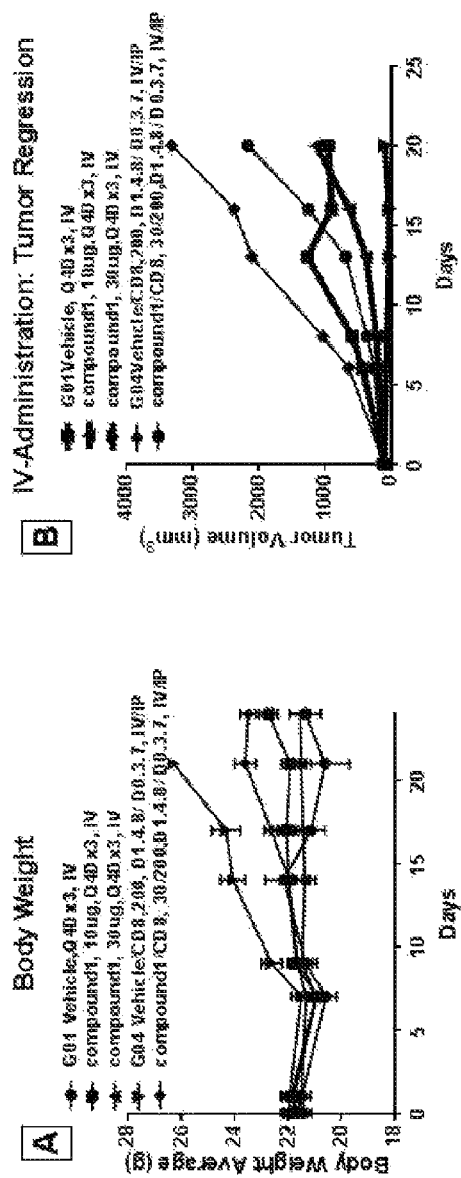
FIG. 10: IV administration of Compound 1 on CD8 T cells engagement induces tumor regression on CT-26 tumor mouse model.

There was a significant tumor growth inhibition with a 30 μg dose of Compound 1 compared to vehicle control as illustrated in (FIG. 10). Depletion of CD8 T-cells prior to IV administration of 30 μg Compound 1 of 30 μg/mouse abrogated tumor growth inhibition.

In the absence of CD8 T-cells, the immune system lost the function that mediates tumor growth inhibition as indicated by diamond-shaped points (FIG. 10) as compared to the intact system in square shaped data points in the control cohorts. Furthermore, Compound 1 lost efficacy in the absence of CD8-T cells as indicated by circle-shaped data points (neutralizing CD-8 antibody included) as compared to intact system with Compound 1 treatment in upside down triangle graph. These results indicate that Compound 1 engaged induces a tumor specific CD8+ T-cell response. Thus, Compound 1 appears to induce adaptive immunity.

The effect of Compound 1 on tumor and draining lymph node on immune cells in the CT-26 tumor model was tested using the dosing schedule used in the tumor regression studies. Briefly, 200-250 $mm^3$ CT-26 syngeneic tumors were established in 7 week old, female BALB/c mice followed by IV dose injection of 30 μg/mouse with Compound 1 or vehicle (40% PEG/Saline). Eight mice treated with Compound 1 and vehicle treated mice were sacrificed 24 hrs following the first IV dose (Day 1). A similar repeat dose cohort was generated on day 5 approximately 24 hours after a second dose. At both time points, the tumor and draining, inguinal lymph nodes (dLN) were harvested and analyzed by flow cytometry as experimental outline in FIG. 9.

Figure 9:
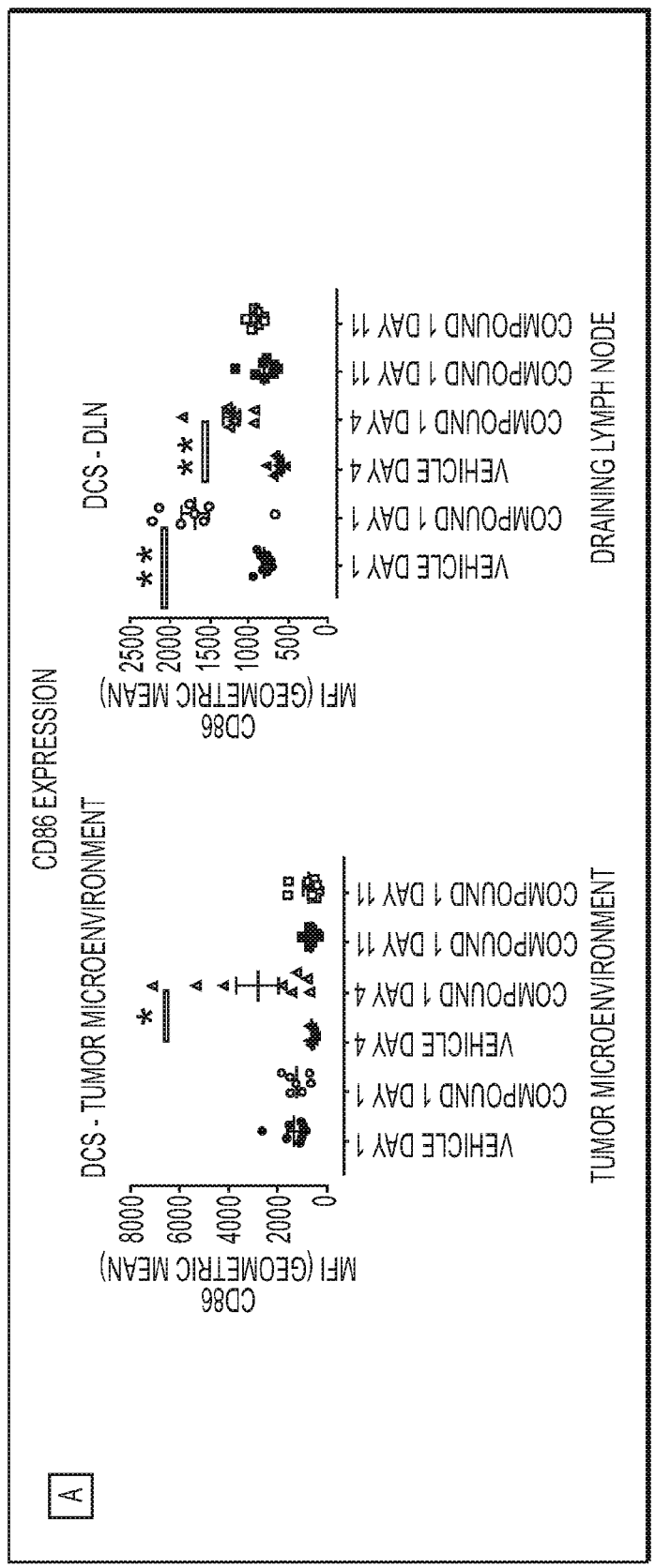
FIG. 9: IV administration of Compound 1 engaged tumor, draining lymph node and systemic Immune Cells.
Figure 9:
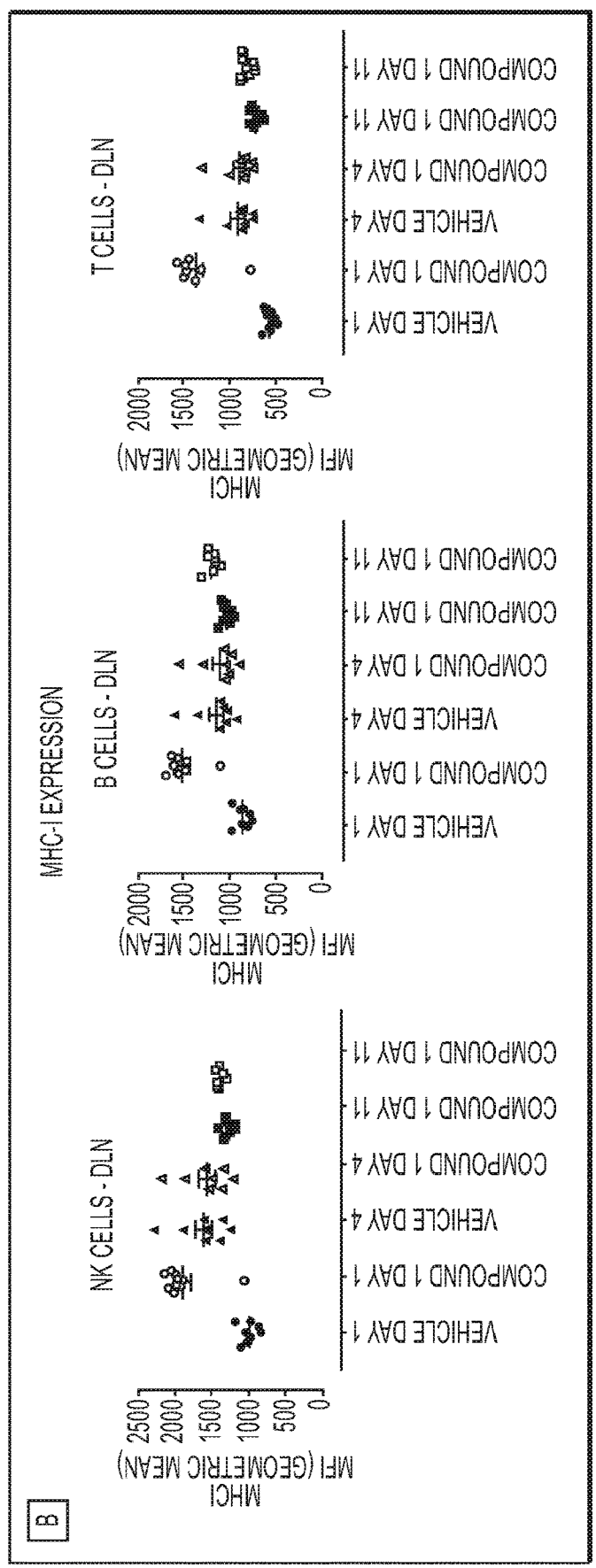

There was an increase in dendritic cells in the tumor microenvironment and draining lymph node following IV administration of Compound 1 (see FIG. 9). There was increased MHC-1 expression in NK, B and T cells in the draining lymph nodes. These findings further support that Compound 1 activates STING in immune cells to elicit tumor growth inhibition and induce long term immunity through enhance antigen presentation and T cell education.

Example 20—Injectable Parenteral Composition

An injectable form for administering the present invention is produced by stirring 1.7% by weight of Compound 1 in 10% by volume propylene glycol in water.

While the preferred embodiments of the invention are illustrated by the above, it is to be understood that the invention is not limited to the precise instructions herein disclosed and that the right to all modifications coming within the scope of the following claims is reserved.

The invention claimed is:

1. A method of treating cancer in a human comprising systemically administering an effective amount of a STING agonist to said human, wherein the STING agonist induces a higher concentration of at least one cytokine in a tumor microenvironment of said human compared with the concentration of said cytokine in the blood, serum, and/or plasma of said human, wherein the STING agonist is a compound of formula

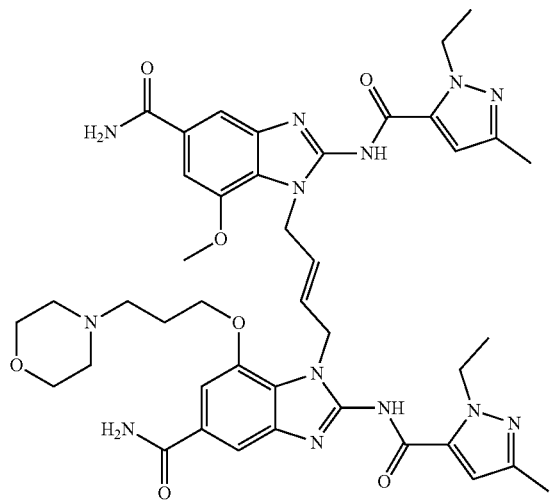 [SMILES: CCn1nc(C)cc1C(=O)Nc1nc2cc(C(N)=O)cc(OC)c2n1C/C=C/Cn1c(NC(=O)c2cc(C)nn2CC)nc2cc(C(N)=O)cc(OCCCN3CCOCC3)c21]

and tautomers thereof, or a pharmaceutically acceptable salt thereof, and wherein the cancer is selected from non-small cell lung cancer (NSCLC), microsatellite stable (MSS) colorectal cancer, gastroesophageal adenocarcinoma (GEC), squamous cell carcinoma of the head and neck (SCCHN), colon, breast, liver, pancreas, prostate, melanoma, acute myeloid leukemia (AML), and myelodysplastic syndrome (MDS).

2. The method of claim 1 wherein the cytokine is selected from IL-6, TNFα, IFNβ, and IFNγ.

3. The method of claim 1 wherein the STING agonist increases the concentration of IL-6 at least three times as much in the tumor microenvironment in said human compared with the concentration of IL-6 levels in the blood, serum, and/or plasma of said human.

4. The method of claim 1 wherein the STING agonist increases the concentration of TNFα at least three times as much in the tumor microenvironment in said human compared with the concentration of TNFα levels in the blood, serum, and/or plasma of said human.

5. The method of claim 1 wherein the STING agonist increases the concentration of IFNγ at least three times as much in the tumor microenvironment in said human compared with the concentration of IFNγ levels in the blood, serum, and/or plasma of said human.

6. The method of claim 1 wherein the STING agonist increases the concentration of IFNγ at least three times as much in the tumor microenvironment in said human compared with the concentration of IFNγ levels in the blood, serum, and/or plasma of said human.

7. The methods of claim 1 wherein the STING agonist has an IC50 of less than about 10 μM.

8. The methods of claim 1 wherein the STING agonist has an IC50 of less than about 1 μM.

9. The methods of claim 1 wherein the STING agonist has an IC50 of less than about 0.1 μM.

10. The methods of claim 1 wherein the STING agonist provides an AUC (0-24) of about 850-1060 ng·hr/ml when administered systemically to said human.

11. The method of claim 1 wherein the STING agonist provides a mean Cmax of about 1900-3800 ng/ml of said STING agonist when administered to said human.

12. The method of claim 1 wherein the STING agonist has a significantly higher Cmax concentration in the tumor microenvironement of said human compared with blood, serum and/or plasma of said human.

13. The method of claim 1 wherein the half-life of said STING agonist is significantly longer in the tumor microenvironment of said human compared with the blood, serum and/or plasma of said human.

14. The method of claim 1 wherein the STING agonist is administered to said human via an administration route selected from intravenous, subcutaneous, oral, and transdermal.

15. The method of claim 1 wherein the STING agonist is administered to said human intravenously.

16. The method of claim 1 wherein said cancer is a solid tumor.

17. A method of administering a STING agonist to a human in need thereof comprising systemically administering said STING agonist to said human, wherein the STING agonist is a compound of formula

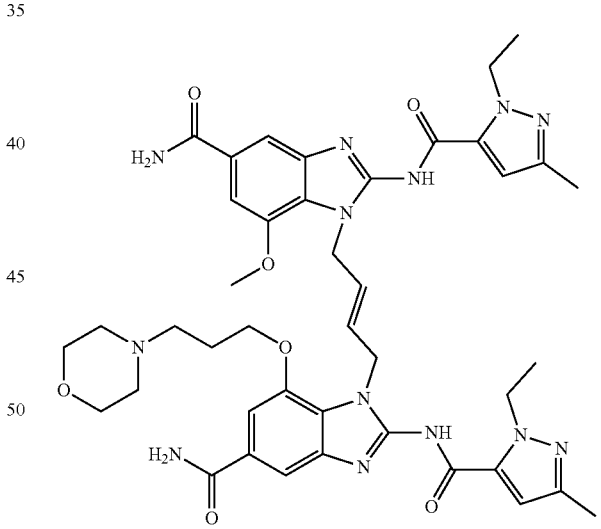

and tautomers thereof, or a pharmaceutically acceptable salt thereof.

18. The method of claim 17 wherein the STING agonist increases the concentration of at least one cytokine in the blood of said human to a concentration effective to stimulate Tcells in said human.

19. The method of claim 17 wherein the STING agonist does not increase cytokine levels in the blood of said human to a concentration high enough to cause dose limiting toxicity.

20. The method of claim 17 wherein the human has at least one disease selected from: inflammation, allergic and autoimmune diseases, infectious diseases, hepatitis C virus (HCV), hepatitis B virus (HBV), influenza, skin warts, multiple sclerosis, human immunodeficiency virus (HIV) infection, AIDS, cancer, and pre-cancerous syndromes.

21. The method of claim 17 wherein the STING agonist increases the concentration of at least one pro-inflammatory cytokine in disease tissue in said human at least three times higher than the concentration of said at least one pro-inflammatory cytokine in the blood, plasma or serum of said human.

22. The method of claim 1 wherein the concentration of the, at least one cytokine, not in the tumor microenvironment is measured in the blood.

23. The method of claim 1 wherein the concentration of the, at least one cytokine, not in the tumor microenvironment is measured in the serum.

24. The method of claim 1 wherein the concentration of the, at least one cytokine, not in the tumor microenvironment is measured in the plasma.

* * * * *